US008227616B2

(12) United States Patent
Blackwell et al.

(10) Patent No.: US 8,227,616 B2
(45) Date of Patent: *Jul. 24, 2012

(54) CYANOPYRIDINE ANTIBACTERIAL AGENTS AND METHODS OF USE THEREOF

(75) Inventors: Helen E. Blackwell, Middleton, WI (US); Matthew D. Bowman, Vernon, CT (US); Jennifer C. O'Neill, Madison, WI (US); Joseph R. Stringer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/815,250

(22) Filed: Jun. 14, 2010

(65) Prior Publication Data

US 2010/0261763 A1 Oct. 14, 2010

Related U.S. Application Data

(63) Continuation of application No. 11/749,573, filed on May 16, 2007, now Pat. No. 7,737,164.

(60) Provisional application No. 60/747,628, filed on May 18, 2006.

(51) Int. Cl.
*C07D 211/78* (2006.01)
*A61K 31/44* (2006.01)

(52) U.S. Cl. ........................................ 546/286; 514/344

(58) Field of Classification Search .................. 546/286; 514/344

See application file for complete search history.

(56) References Cited

U.S. PATENT DOCUMENTS

| | | | |
|---|---|---|---|
| 7,361,774 | B2 | 4/2008 | Ohnogi |
| 7,714,025 | B2 | 5/2010 | Rose |
| 7,737,164 | B2 | 6/2010 | Blackwell et al. |
| 2007/0128658 | A1 | 6/2007 | Blackwell et al. |
| 2009/0270423 | A1 | 10/2009 | Blackwell et al. |

FOREIGN PATENT DOCUMENTS

| | | |
|---|---|---|
| JP | 4-279568 | 10/1992 |
| WO | WO 98/15532 | 4/1998 |
| WO | WO 2006/084056 | 8/2006 |
| WO | WO 2008/016738 | 2/2008 |

OTHER PUBLICATIONS

Hafez et al Journal of Chemical Technology and Biotechnology 1992, 55, 333-338.*
Ettmayer et al J Med Chem 2004, 47, 2393-2404.*
Andrews, J.M. (2001) "Determination of Miniumum Inhibitory Concentrations," *J. Antimicrob. Chemother.* 48(Supp. 1):5-16.
Barnick et al. (1979) "A Convenient Direct Method for the Preparation of β-Keto-Acids," *Synthesis* 79:787-788.
Bassler et al. (2006) "Bacterially Speaking," *Cell* 125:237-246.
Bassler et al. (1995) "Intracellular Communication in Marine *Vibrio* Species: Density-Dependent Regulation of the Expression of Bioluminescence," In; *Two Component Signal Transduction*, Hoch et al. Eds., Am. Soc. Microbiol., Washington D.C., pp. 431-435.
Bassler et al. (1993) "Intercellular Signalling in *Vibrio harveyi*: Sequence and Function of Genes Regulating Expression of Luminescence," *Mol. Microbiol.* 9(4):773-786.
Bassler et al. (1994) "Multiple Signaling Systems Controlling Expression of Luminescence in *Vibrio harvey* Sequenceand Function of Genes Encoding a Second Sensory Pathway," *Mol. Micobiol.* 13(2):273-286.
Bauer et al. (1966) *Tech Bull. Reg. Med. Technologists* 36:49-52.
Behrendt et al. (1999) "Phootomodulation of the Conformation of Cyclic Peptides with Azobenzene Moieties in the Peptide Backbone," *Angew. Chem. Int. Ed. Engl.* 38:2771-2774.
Blackwell, H.E. (2006) "Hitting the SPOT: Small Molecule Macroarrays Advance Combinatorial Synthesis," *Curr. Opin. Chem. Biol.* 10:203-212.
Blackwell et al. (2003) "Out of the Oil Bath and into the Oven—Microwave-Assisted Combinatorial Chemistry Heats Up," *Org. Biomol. Chem.* 1:1251-1555.
Bowden et al. (1990) "Structure-Activity Relations. Part 5. Antibacterial Activity of a Series of Substituted (E)-3-(4-Phenylbenzoyl)acrylic Acids, -Chalcones, -2-Hydroxychalcones and -α-Bromochalcones; Addition of Cyteine to Substitutes 3-Benzoylacrylic Acids and Related Compounds," J. Chem. Res. (S) 377.
Bowden et al. (1990) "Structure-Activity Relations. Part 5. Antibacterial Activity of a Series of Substituted (E)-3-(4-Phenylbenzoyl)acrylic Acids, -Chalcones, -2-Hydroxychalcones and -α-Bromochalcones; Addition of Cyteine to Substitutes 3-Benzoylacrylic Acids and Related Compounds," J. Chem. Res. (M) 2801-2830.
Bowden et al. (1979) "Structure-Activity Relations. Part 4. Reactivity and Anti-Bacterial Activity of 3-Aroylacrylic Acids and Their Methyl Esters," J. Chem. Res. (S) 8.
Bowman et al. (Apr. 2007) "Rapid Identification of Antibacterial Agents Effective Against *Staphylococcus aureus* Using Small-Molecule Macroarrays," *Chem. Biol.* 14:351-357.
Bowman et al. (2006) "Efficient Synthesis of Small Molecule Macroarrays: Optimization of the Macroarray Synthesis Platform and Examination of Microwave and Conventional Heating Methods," *Tetrahedron* 62:4715-4727.

(Continued)

*Primary Examiner* — Janet Andres
*Assistant Examiner* — John Mabry
(74) *Attorney, Agent, or Firm* — Greenlee Sullivan P.C.

(57) ABSTRACT

The present invention relates generally to compounds providing antibacterial therapeutic agents and preparations, and related methods of using and making antibacterial compounds. Antibacterial compounds of the present invention include chalcone, alkylpyrimidine, aminopyrimidine and cyanopyridine compounds and derivatives thereof exhibiting minimum inhibitory concentrations (MIC) similar to or less than conventional antibacterial compounds in wide use. For example, the present invention provides chalcone and cyanopyridine compounds, and derivatives thereof, exhibiting high antibacterial activities having multiple electron withdrawing group substituents, such as halogens and fluorinated alky groups, and optionally having hydroxyl and/or alkoxyl groups substituents.

20 Claims, 49 Drawing Sheets

OTHER PUBLICATIONS

Bowman et al. (2006) "Discovery of Fluorescent Cyanopyridine and Deazalumazine Dyes Using Small Molecule Macroarrays," *Org. Lett.* 8:1645-1648.

Bowman et al. (2004) "Microwave-Accelerated SPOT-Synthesis on Cellulose Supports," *Org. Lett.* 6(12):2019-2022.

Carpino et al. (1972) "The 9-Fluorenylmethoxycarbonyl Amino-Protecting Group," *J. Org. Chem.* 37(22):3404-3409.

Dobaria, A. V. et al. (2002) "Synthesis and antimicrobial screening of cyanopyridines," J. Indian Chem. Soc. 79:772-773.

Eberhard et al. (1986) "Analogs of the Autoinducer of Bioluminescence in *Vibrio fischeri*," *Arch. Microbiol.* 146:35-40.

Eberhard et al. (2000) "Chemical Synthesis of Bacterial Autoinducers and Analogs," *Methods Enzymol.* 305:301-315.

Fleming et al. (Nov. 13, 1995) "Chemical Reagents in Photoaffinity Labeling," *Tetrahedron* 51(46):12479-12520.

Fray et al. (1999) "Plants Genetically Modified to Prodice N-acylhomoserine Lactones Communicate with Bacteria," *Nat. Biotechnol.* 17:1017-1020.

Frezza et al. (2006) "Synthesis and Biological Evaluatioon of Homoserine Lactone Derived Ureas as Antafonists of Bacterial Quorum Sensing," *Bioorg. Med. Chem.* 14:4781-4791.

Fuqua et al. (2002) "Listening in on Bacteria: Acyl-Homoserine Lactone Signaling," *Nat. Rev. Mol. Cell Biol.* 3:685-695.

Fuqua et al. (2001) "Regulation of Gene Expression by Cell-to-Cell Communication: Acyl-Homoserine Lactone Quorum Sensing," *Ann. Rev. Genet.* 35:439-468.

Ghani et al. (1990) "Nitriles in Heterocyclic Synthesis: A Novel Route for the Synthesis of Naphthodipyrans, Pyridines 2H- and 2H-Pyrans" Coll. Czech. Commun. 35:524-534.

International Search Report and Written Opinion PCT/US2007/069069.

International Preliminary Report on Patentability PCT/US2007/069069.

Kappe, C.O. (2004) "Controlled Microwave Heating in Modern Organic Synthesis," *Angew Chem. Int. Ed.* 43:6250-6284.

Kappel et al. (2005) "A Convenient Orthogonally Cleavable Methionine Handle for Anchoring Amines to Polymeric Supports," *J. Comb. Chem.* 7:78-84.

Koch et al. (2005) "The LuxR Receptor: The Sites of Interaction with Quorum-Sensing Signals and Inhibitors," *Microbiology* 151:3589-3602.

Krohnke, F. (1976) "The Specific Synthesis of Pyridines and Oligopyridines," *Synthesis* :1-24.

Lee et al. (2006) "Activity of Purified QscR, a *Pseudomonas aeruginosa* Orphan Quorum-Sensing Transcription Factor," *Mol. Microbiol.* 59:602-609.

Ley et al. (Aug. 2002) "New Tools and Concepts for Modern Organic Synthesis," *Nat. Rev. Drug. Discov.* 1(8):573-586.

Lin et al. (2006) "Rapid Synthesis of Diketopiperazine Macroarrays via Ugi Four-Component Reactions on Planar Solid Supports," *Chem. Commun.* :2884-2886.

Lin et al. (20055) "Small Molecule Macroarray Construction via Ugi Four-Component Reactions," *Org. Lett.* 7:4455-4458.

Marzinzik et al. (1998) "Key Intermediates in Combinatorial Chemistry: Access to Various Heterocycles from α,β-Unsaturated Ketones on the Solid Phase," *J. Org. Chem.* 63:723-727.

Matsui et al. (1992) *J. Chem. Soc. Perk. Trans.* 2:201-206.

Misra et al. (1971) Studies in Potential Germicides: Part VII, Syntheses of Napthalene and Phenanthrene Analogues of Chalcones 34:260-264.

Ni et al. (2004) "Recent Advances in Therapeutic Chalcones," *Exp. Opin. Ther. Patents* 14:1669-1691.

Nielsen et al. (2005) "Cationic Chalcone Antibiotics. Design, Synthesis, and Mechanism of Action," *J. Med. Chem.* 48:2667-2677.

Nielson et al. (2004) "Antibacterial Chalcones—Bioisosteric Replacement of the 4'-hydroxy Group," *Bioorg. Med. Chem.* 12:3047-3054.

Nogrady (1985) "Pro-Drugs and Soft Drugs," In; *Medicinal Chemistry A Biochemical Approach*, Oxford Press, New York, pp. 388-392.

Powers et al. (1998) "Automated Parallel Synthesis of Chalcone-Based Screening Libraries," *Tetrahedron* 54:4085-4096.

Rajvaidya et al. (2004) "Synthesis and Microbiological Activities of Some Pyrazoles and Cyanopyridines," *Indian J. Chem.* 43B:906-908.

Rathke et al (Oct. 1985) "Synthesis of β-Keto Acids and Methyls Ketones Using *Bis* (trimethylsily) Malonate and Triethylamine in the Presence of Lithium or Magnesium Halides," *Synth. Commun.* 15(12):1039-1049.

Schultz et al. (2003) "Mechanism and Dynamics of Azobenzene Photoisomerization," *J. Am. Chem. Soc.* 125(27):8098-8099.

Stringer et al. (Jan. 29, 2007) "Rapid Identification of Antibacterial Agents Effective Against *Staphylococcus aureus* Using Small-Molecule Macroarrays," Abstract for Poster Presentation at the American Chemical Society Meeting held in Chicago IL (USA) Mar. 2007.

Stringer et al. (Mar. 28, 2007) "Rapid Identification of Antibacterial Agents Effective Against *Staphylococcus aureus* Using Small-Molecule Macroarrays," Poster Presentation at the American Chemical Society Meeting held in Chicago IL (USA) Mar. 25-Mar. 29, 2007.

Tsiodras et al. (Jul. 2001) "Linezolid Resistance in a Clinical Isolate of *Staphylococcus aureus*," Lancet 358:207-208.

Tu et al. (2005) "An Efficient Improve for the Kröhnke Reaction: One-Pot Synthesis of 2,4,6-Triarylpyridines Using Raw Materials Under Microwave Irradiation," *Chem. Lett.* 34:732-733.

Yamaguchi et al. (1998) "A New Expedient Route to 2,6-Diaryl-3-cyano-4-(trifluoromethyl)pyridines" J. Het. Chem. 35:805-810.

* cited by examiner

A

B

4At: $R^1$ = 4-OH, $R^2$ = 2,4-Cl
4Be: $R^1$ = 3-OH, $R^2$ = 3-Br
4Bl: $R^1$ = 3-OH, $R^2$, 2,3-Cl
4Bo: $R^1$ = 3-OH, $R^2$ = 2,3,6-Cl
4Bv: $R^1$ = 3-OH, $R^2$ = 3,5-CF$_3$
4Cf: $R^1$ = 3-OMe, 4-OH; $R^2$ = 4-Br

6Al: $R^1$ = 4-OH, $R^2$ = 2,3-Cl
6Ao: $R^1$ = 4-OH, $R^2$ = 2,3,6-Cl
6Bt: $R^1$ = 3-OH, $R^2$ = 2,4-Cl

9Cf: $R^1$ = 3-OMe, 4-OH, $R^2$ = 4-Br

C

D

E

F

E

F

G

H

M

N

O

P

A

B

G

H

D

E

F

A

B

C

D

E

F

H

J

K

L

M

N

CYANOPYRIDINE ANTIBACTERIAL AGENTS AND METHODS OF USE THEREOF

CROSS-REFERENCE TO RELATED APPLICATIONS

This application is a division of U.S. application Ser. No. 11/749,573, filed May 16, 2007 which claims priority under 35 U.S.C. 119(e) to U.S. provisional Patent Application 60/747,628, filed May 18, 2006, each of which applications is hereby incorporated by reference in its entirety.

STATEMENT REGARDING FEDERALLY SPONSORED RESEARCH OR DEVELOPMENT

This invention was made with government support awarded by the following agencies: National Science Foundation Grant CHE-0449959. The United States government has certain rights in the invention.

BACKGROUND OF INVENTION

The emergence of resistant bacterial strains without the increased development of new antibiotic structure classes constitutes a serious medical crisis. Brown, E. D.; Wright, G. D. *Chem. Rev.* 2005, 105, 759-774; Coates, A.; Hu, Y.; Bax, R.; Page, C. *Nat. Rev. Drug Discovery* 2002, 1, 895-910. Infection with the common pathogen *Staphylococcus aureus* has been estimated to double the cost, length of stay, and the even death rate in New York City hospitals. Rubin, R. J.; Harrington, C. A.; Poon, A.; Dietrich, K.; Greene, J. A.; Moiduddin, A. *Emerging Infectious Diseases* 1999, 5, 9-17. Furthermore, resistance in *S. aureus* to linezolid, the first example in the latest approved class of antimicrobials, has already been reported only one year after the drug's approval and emphasizes the need for increased discovery and additional research tools for developing new antibiotic structure classes. Tsiodras, S., Gold, H. S.; Sakoulas, G.; Eliopoulos, G. M.; Wennersten, C.; Venkataraman, L.; Moellering, R. C. *Lancet* 2001, 207-208.

In view of the foregoing, the significant need exists for new methods, molecules and technologies to work towards eliminating these limitations of commercially available anti-bacterial compounds.

SUMMARY OF THE INVENTION

The present invention relates generally to compounds providing antibacterial therapeutic agents and preparations, and related methods of using and making antibacterial compounds. Antibacterial compounds of the present invention include chalcone, alkylpyrimidine, aminopyrimidine and cyanopyridine compounds and derivatives thereof exhibiting minimum inhibitory concentrations (MIC) similar to or less than conventional antibacterial compounds in wide use. For example, the present invention provides chalcone and cyanopyridine compounds, and derivatives thereof, exhibiting high antibacterial activities having multiple electron withdrawing group substituents, such as halogens and fluorinated alky groups, and optionally having hydroxyl and/or alkoxyl groups substituents. The present invention provides compounds exhibiting useful in vitro antibacterial activities against a variety of bacteria strains, including drug resistant bacterial strains, thereby providing antibacterial therapeutic agents and preparations useful for a range of important clinical applications.

The present invention also provides versatile methods for screening compounds for antimicrobial activity, including antibacterial activity. The present methods are based on using combinatorial synthetic methods to generate arrays (e.g., macroarrays) comprising a large number of candidate molecules, identifying compounds of the array exhibiting antimicrobial activity and quantifying MICs of select compounds in the array. Structurally distinct candidate molecules are synthesized and bonded to distinct known locations (e.g., spots or regions) on a surface of a unitary substrate via linkers (i.e., linking groups attaching the candidates to the substrate). Candidate molecules are subsequently liberated from the substrate by cleaving the linkers and assayed for antibacterial activity by bringing the array into contact with a microbial culture, such as a bacterial culture or fungal culture. An advantage provided by the macroarray platform of the present screening methods is that qualitative and/or quantitative characterization of the antibacterial properties of large numbers of candidate compounds can be achieved on a relatively short time scale (i.e. days) using a single overlay visualization and/or quantification assay step.

In an aspect, the present invention provides a composition of matter comprising a chalcone compound or derivative thereof having a formula:

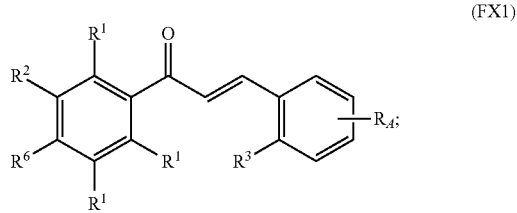

(FX1)

wherein

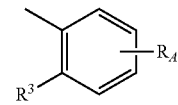

is selected from the group consisting of:

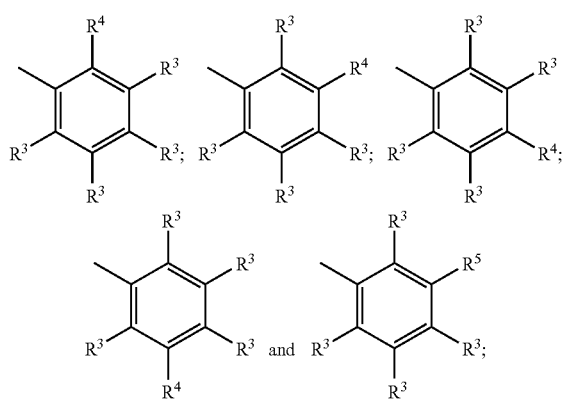

or a pharmaceutically acceptable salt or ester thereof;

wherein each $R^1$, independent of other $R^1$, is independently selected from the group consisting of a hydrogen, a methyl group, a halogen, an amine group, a substituted or unsubstituted $C_1$-$C_8$ alkyl group, a substituted or unsubstituted $C_1$-$C_8$ alkenyl group, a substituted or unsubstituted $C_1$-$C_8$ alkynyl group, a substituted or unsubstituted $C_1$-$C_8$ alkoxyl group, a hydroxyl group, a —CN group, an azide group, and a —$NO_2$ group;

wherein $R^2$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$;

wherein $R^6$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$ and wherein at least one of $R^2$ and $R^6$ is —OH, —$OCH_3$, —$OCH_2CH_3$, —$OCH_2CH_2CH_3$, —$OCH_2CH_2CH_2CH_3$ or —$OCH_2CH_2CH_2CH_2CH_3$;

wherein each $R^3$, independent of other $R^3$, is independently selected from the group consisting of a hydrogen, a methyl group, a halogen, an amine group, a substituted or unsubstituted $C_1$-$C_8$ alkyl group, a substituted or unsubstituted $C_1$-$C_8$ alkenyl group, a substituted or unsubstituted $C_1$-$C_8$ alkynyl group, a substituted or unsubstituted $C_1$-$C_8$ alkoxyl group, a hydroxyl group, a —CN group, an azide group, and a —$NO_2$ group.

wherein $R^4$ is selected from the group consisting of —F, —Cl, —Br, and —I; and wherein $R^5$ is selected from the group consisting of —$CF_3$, —$CF_2CF_3$, —$CF_2CF_2CF_3$, —$CF_2CF_2CF_2CF_3$, and —$CF_2CF_2CF_2CF_2CF_2CF_3$.

Chalcone compositions, and derivatives thereof, of this aspect of the present invention include compounds exhibiting significant antibacterial activity including antibacterial agents for therapeutic applications and generally for inhibiting the growth of bacteria. The present chalcone compositions and derivatives thereof include broad-spectrum antibacterial compounds exhibiting significant antibacterial activities for a range of bacteria species and strains, antibacterial compounds exhibiting species selective activities, and antibacterial compounds exhibiting significant activities for drug resistant bacteria strains.

In an embodiment of this aspect, a chalcone compound or derivative thereof of the present invention has a formula selected from the group consisting of:

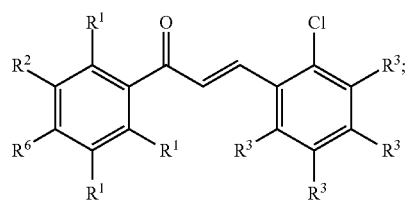
(FX2)

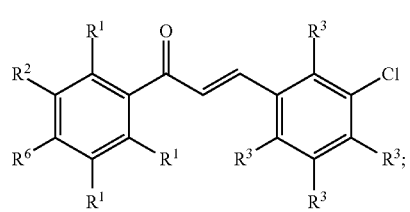
(FX3)

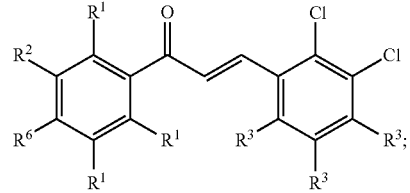
(FX4)

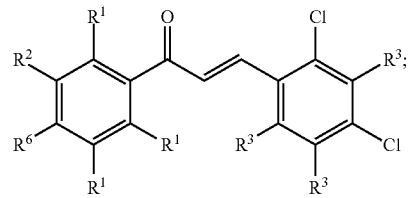
(FX5)

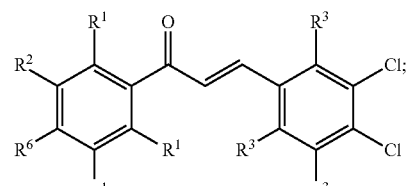
(FX6)

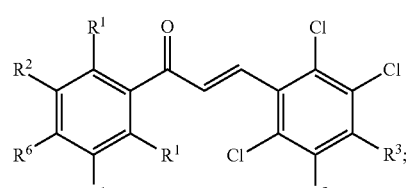
(FX7)

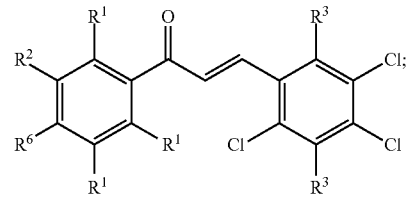
(FX8)

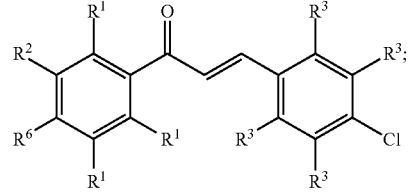
(FX9)

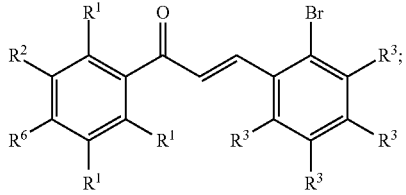
(FX10)

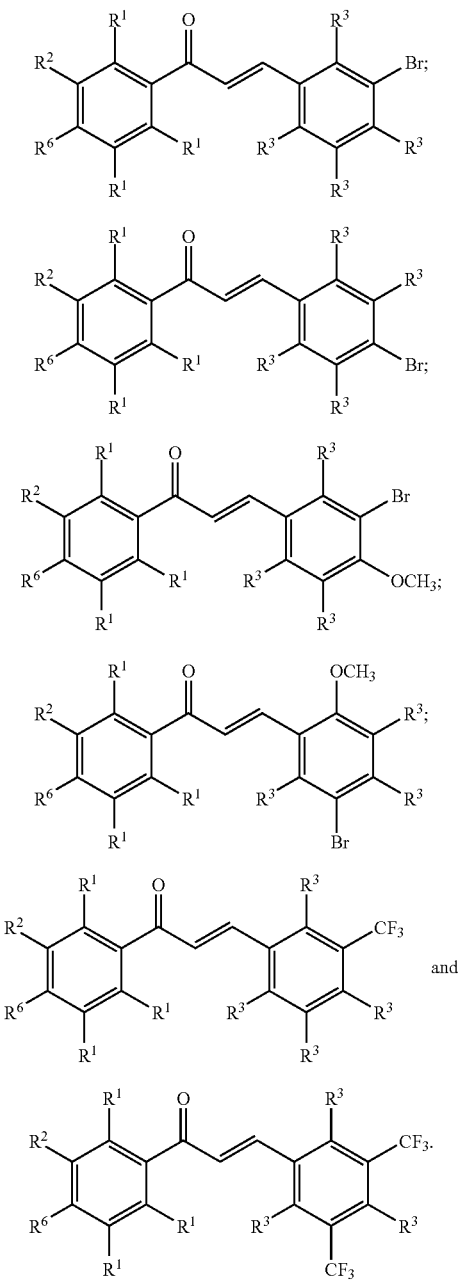

wherein $R^2$ is —OH and $R^6$ is —H; or optionally wherein $R^2$ is —H and $R^6$ is —OH; or optionally wherein $R^2$ is O—H and $R^6$ is —OCH$_3$; or optionally wherein $R^2$ is —OCH$_3$ and $R^6$ is —OH. In a specific embodiment, for example, a composition of the present invention has one the above formulas (FX1-FX16), wherein $R^1$ is —H, wherein $R^2$ is —OH, wherein $R^6$ is —H, and wherein each $R^3$, independent of other $R^3$, is independently selected from the group consisting of —H, —CH$_3$, —F, —Cl, —Br, and —I.

In specific embodiments of this aspect, the present invention provides chalcone compositions and derivatives thereof having one of the above formulas (FX1-FX16), optionally wherein $R^1$ is H, wherein $R^2$ is —OH, —OCH$_3$, or —H, $R^6$ is —OH, —OCH$_3$, or —H; $R^3$ is H and wherein $R^4$ is selected from the group consisting of —F, —Cl, —Br, and —I. In specific embodiments of this aspect, the present invention provides chalcone compositions and derivatives thereof having one of the above formulas (FX1-FX16), optionally wherein $R^1$ is —H, wherein $R^2$ is —OH, —OCH$_3$, or —H, $R^6$ is —OH, —OCH$_3$, or —H; $R^3$ is —H and wherein $R^5$ is —CF$_3$.

In specific embodiments of this aspect, the present invention provides chalcone compositions and derivatives thereof having one of the above formulas (FX2-FX16), optionally wherein $R^1$ is —H; wherein $R^2$ is —OH, —OCH$_3$, or —H; $R^6$ is —OH, —OCH$_3$, or —H; $R^3$ is —H, —F, —Cl, —Br, or —CH$_3$; wherein $R^4$ is —Cl or —Br; and $R^5$ is —CF$_3$.

In specific embodiments of this aspect, the present invention provides chalcone compositions and derivatives thereof having a formula selected from the group consisting of:

In specific embodiments of this aspect, the present invention optionally provides chalcone compositions and derivatives thereof having one of the above formulas (FX1-FX16) wherein each $R^1$, independent of other $R^1$, is independently selected from the group consisting of —H, —CN, —CH$_3$, —CH$_2$CH$_3$, —CH$_2$CH$_2$CH$_3$—CH$_2$CH$_2$CH$_2$CH$_3$, —OCH$_3$, —OCH$_2$CH$_3$ and —OCH$_2$CH$_2$CH$_2$CH$_3$; and wherein each $R^3$, independent of other $R^3$, is selected from the group consisting of H, F, Cl, Br, I, —CN, —CF$_3$, —CF$_2$CF$_3$, —CF$_2$CF$_2$CF$_3$, —CH$_3$, —CH$_2$CH$_3$, —CH$_2$CH$_2$CH$_3$, —CH$_2$CH$_2$CH$_2$CH$_3$, —OH, —OCH$_3$, —OCH$_2$CH$_3$ and —OCH$_2$CH$_2$CH$_2$CH$_3$.

In specific embodiments of this aspect, the present invention provides chalcone compositions and derivatives thereof having one of the above formulas (FX1-FX16), optionally

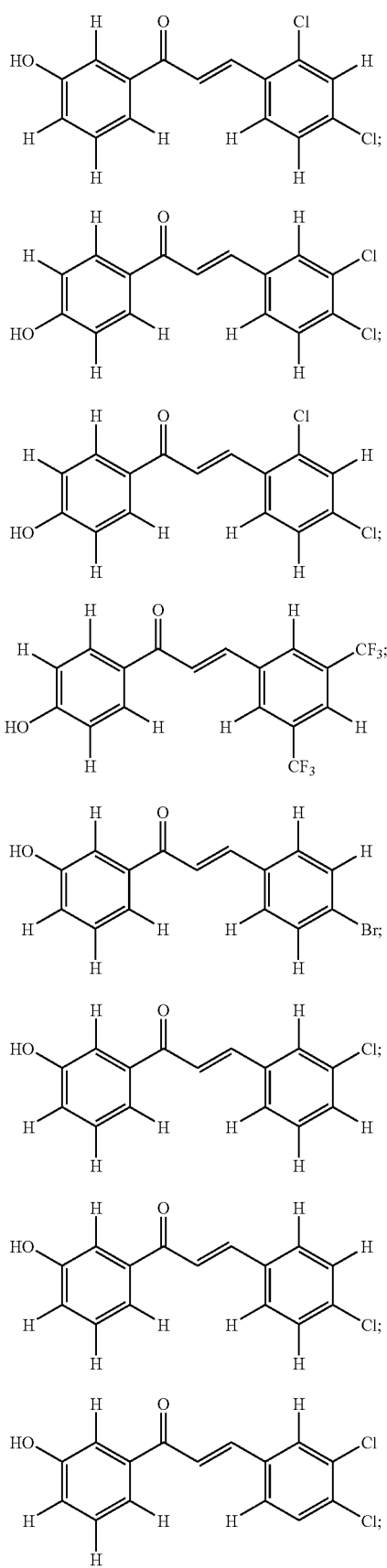
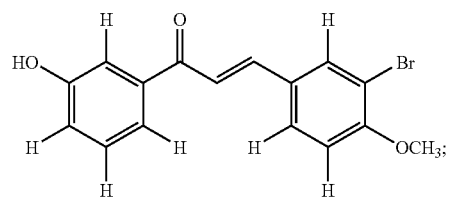
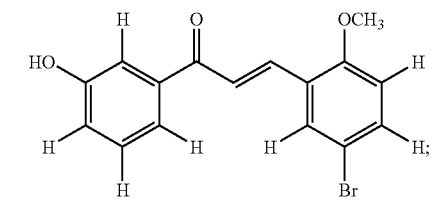
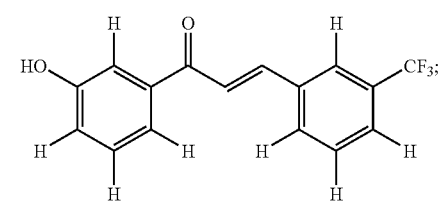
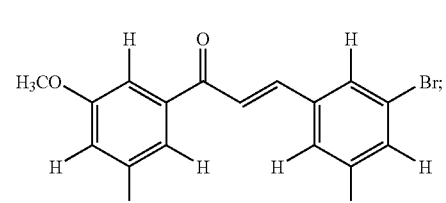
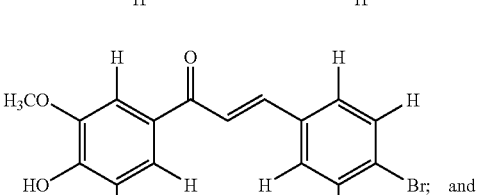
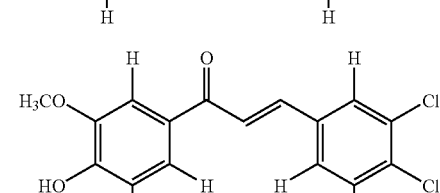
In an aspect, the present invention provides a composition of matter comprising a cyanopyridine compound or derivative thereof having the formula:
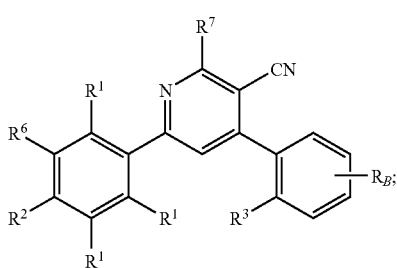

wherein

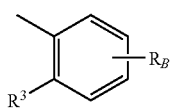

is selected from the group consisting of:

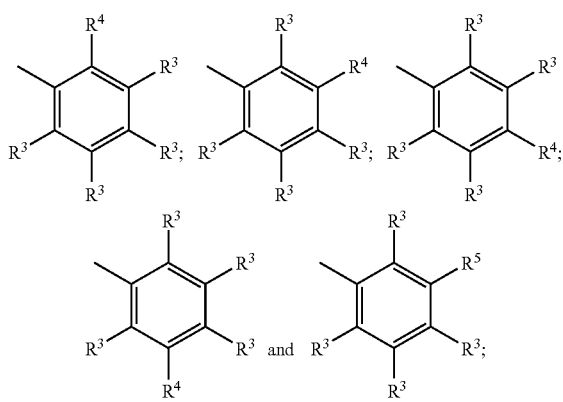

or a pharmaceutically acceptable salt or ester thereof;
wherein each $R^1$, independent of other $R^1$, is independently selected from the group consisting of a hydrogen, a methyl group, a halogen, an amine group, a substituted or unsubstituted $C_1$-$C_8$ alkyl group, a substituted or unsubstituted $C_1$-$C_8$ alkenyl group, a substituted or unsubstituted $C_1$-$C_8$ alkynyl group, a substituted or unsubstituted $C_1$-$C_8$ alkoxyl group, a hydroxyl group, a —CN group, an azide group, and a —$NO_2$ group;
wherein $R^2$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$;
wherein $R^6$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$;
and wherein at least one of $R^2$ and $R^6$ is —OH, —$OCH_3$, —$OCH_2CH_3$, —$OCH_2CH_2CH_3$, —$OCH_2CH_2CH_2CH_3$ or —$OCH_2CH_2CH_2CH_2CH_3$;
wherein each $R^3$, independent of other $R^3$, is independently selected from the group consisting of a hydrogen, a methyl group, a halogen, an amine group, a substituted or unsubstituted $C_1$-$C_8$ alkyl group, a substituted or unsubstituted $C_1$-$C_8$ alkenyl group, a substituted or unsubstituted $C_1$-$C_8$ alkynyl group, a substituted or unsubstituted $C_1$-$C_8$ alkoxyl group, a hydroxyl group, a —CN group, an azide group, and a —$NO_2$ group;
wherein $R^4$ is selected from the group consisting of —F, —Cl, —Br, and —I;
wherein $R^5$ is selected from the group consisting of —$CF_3$, —$CF_2CF_3$, —$CF_2CF_2CF_3$, —$CF_2CF_2CF_2CF_3$, and —$CF_2CF_2CF_2CF_2CF_2CF_3$; and
wherein $R^7$ is selected from the group consisting of hydrogen, a methyl group, a substituted or unsubstituted $C_1$-$C_8$ alkyl group, a substituted or unsubstituted $C_1$-$C_8$ alkenyl group, and a substituted or unsubstituted $C_1$-$C_8$ alkynyl group.

Cyanopyridine compounds or derivatives thereof of this aspect of the present invention include compounds exhibiting significant antibacterial activity including antibacterial agents for therapeutic applications and generally for inhibiting the growth of bacteria. The present cyanopyridine compounds or derivatives thereof include broad-spectrum antibacterial compounds exhibiting significant antibacterial activities for a range of bacteria species and strains, antibacterial compounds exhibiting species selective activities, and antibacterial compounds exhibiting significant activities for drug resistant bacteria strains.

In an embodiment of this aspect, a cyanopyridine compound or derivative thereof of the present invention has a formula selected from the group consisting of:

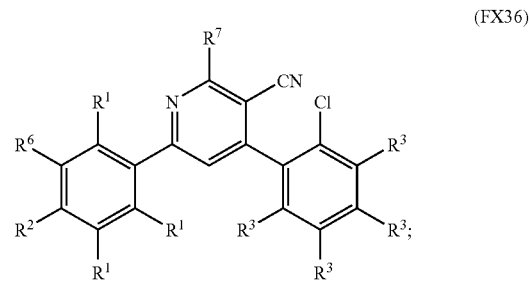
(FX36)

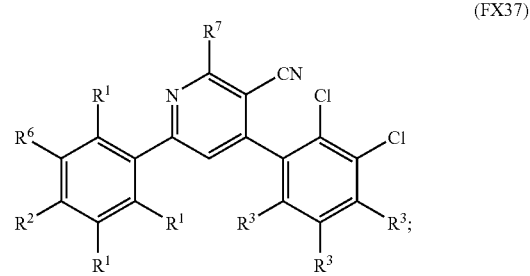
(FX37)

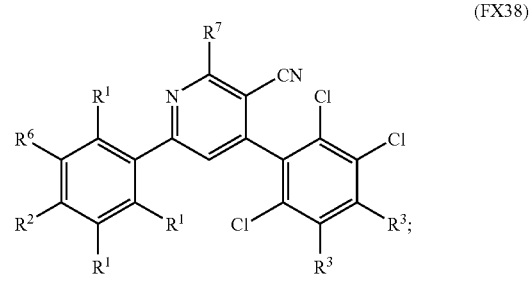
(FX38)

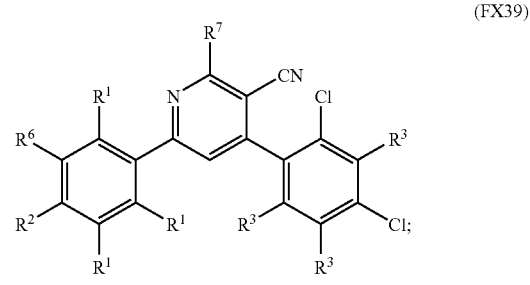
(FX39)

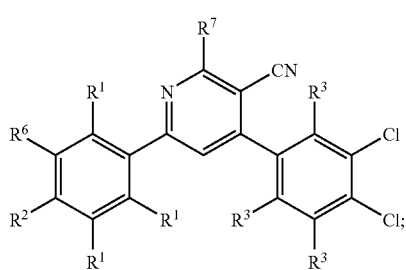
(FX40)

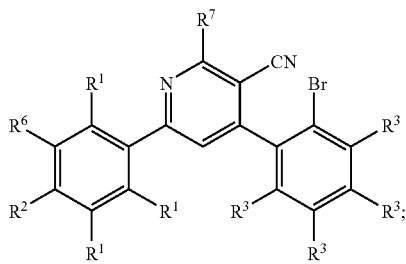
(FX41)

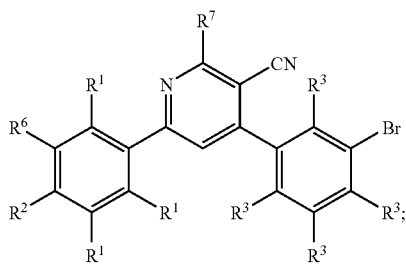
(FX42)

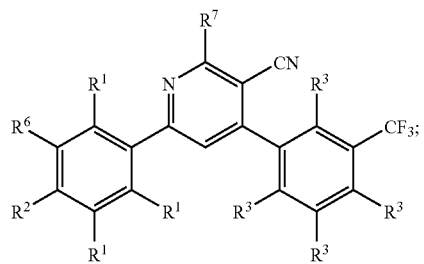
(FX43)

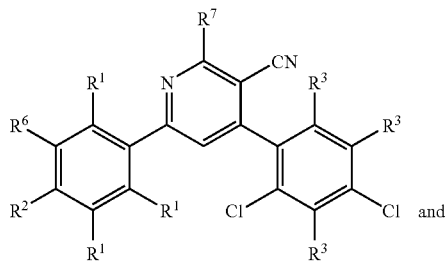
(FX44)

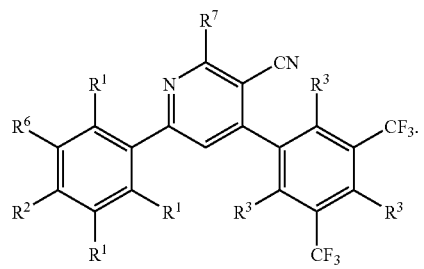
(FX45)

In specific embodiments of this aspect, the present invention optionally provides cyanopyridine compounds and/or derivatives thereof having one of the above formulas (FX35-FX45) wherein each $R^1$, independent of other $R^1$, is independently selected from the group consisting of —H, —CH$_3$, —CH$_2$CH$_3$, —CH$_2$CH$_2$CH$_3$ and —CH$_2$CH$_2$CH$_2$CH$_3$; wherein each $R^3$, independent of other $R^3$, is independently selected from the group consisting of —H, —F, —Cl, —Br, —I, —CF$_3$, —CF$_2$CF$_3$, —CF$_2$CF$_2$CF$_3$, —CH$_3$, —CH$_2$CH$_3$, —CH$_2$CH$_2$CH$_3$, —CH$_2$CH$_2$CH$_2$CH$_3$, —OH, —OCH$_3$, —OCH$_2$CH$_3$ and —OCH$_2$CH$_2$CH$_2$CH$_3$; and wherein $R^7$ is selected from the group consisting of H, —CH$_3$, —CH$_2$CH$_3$, —CH$_2$CH$_2$CH$_3$, and —CH$_2$CH$_2$CH$_2$CH$_3$.

In specific embodiments of this aspect, the present invention provides cyanopyridine compounds and/or derivatives thereof having one of the above formulas (FX35-FX45), wherein optionally $R^7$ is —CH$_3$ or —CH$_2$CH$_3$. In specific embodiments of this aspect, the present invention provides cyanopyridine compounds and/or derivatives thereof having one of the above formulas (FX35-FX45), wherein optionally $R^2$ is —OH and $R^6$ is —H, or wherein $R^2$ is H and $R^6$ is —OH. In specific embodiments of this aspect, the present invention provides cyanopyridine compounds and/or derivatives thereof having one of the above formulas (FX35-FX45) wherein $R^1$ is —H, wherein $R^2$ is —OH, wherein $R^6$ is —H, and wherein each $R^3$ independent of other $R^3$ is selected from the group consisting of —H, —F, —Cl, —Br, and —I. In specific embodiments of this aspect, the present invention provides cyanopyridine compounds and/or derivatives thereof having one of the above formulas (FX35-FX45) wherein optionally $R^2$ is —H and $R^6$ is —OH, or optionally $R^2$ is —OH and $R^6$ is H, or optionally $R^2$ is OH and $R^6$ is —OCH$_3$, or optionally $R^2$ is —OCH$_3$ and $R^6$ is —OH.

In specific embodiments of this aspect, the present invention provides chalcone compositions and derivatives thereof having one of the above formulas (FX36-FX45), optionally wherein $R^1$ is —H; wherein $R^2$ is —OH, —OCH$_3$, or —H; $R^6$ is —OH, —OCH$_3$, or —H; $R^3$ is —H, —F, —Cl, —Br, —CF$_3$ or —CH$_3$; $R^7$ is —CH$_3$ or —CH$_2$CH$_3$.

In specific embodiments of this aspect, the present invention provides cyanopyridine compounds and/or derivatives thereof having a formula selected from the group consisting of:

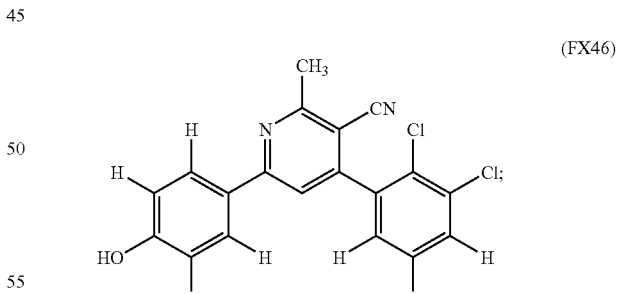
(FX46)

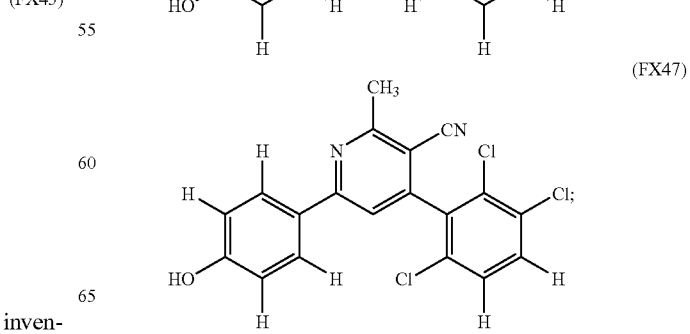
(FX47)

(FX48)
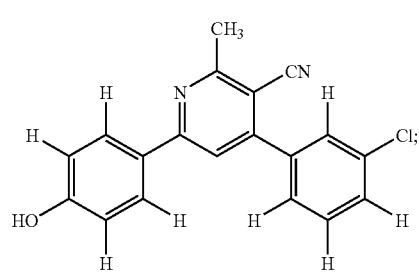
(FX49)
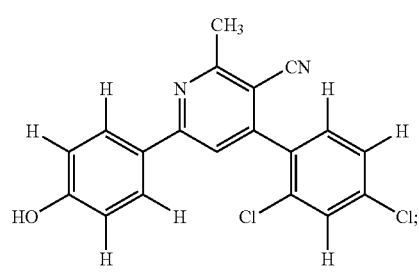
(FX50)
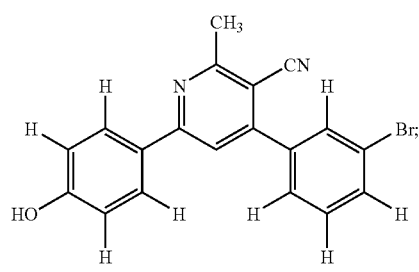
(FX51)
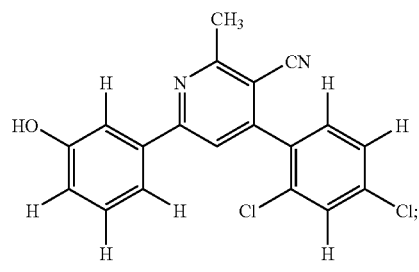
(FX52)
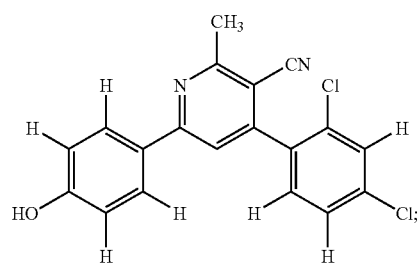
(FX53)
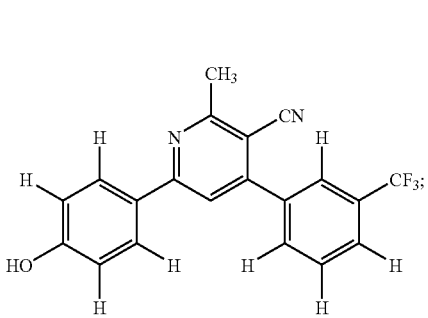
(FX54)
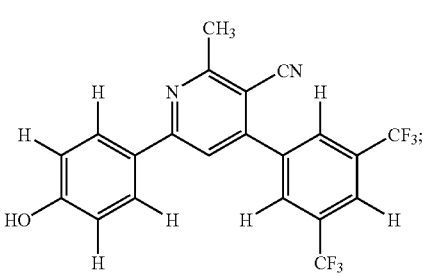
(FX55)
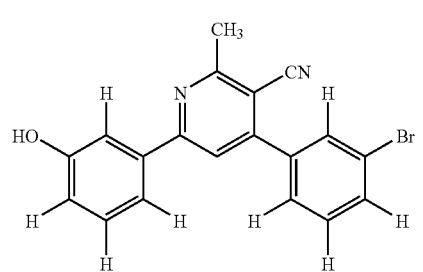
(FX56)
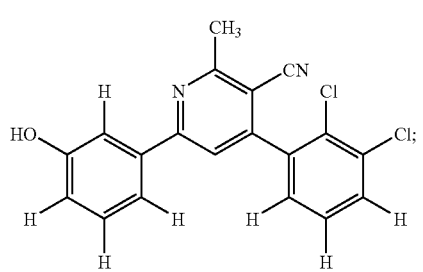
(FX57)
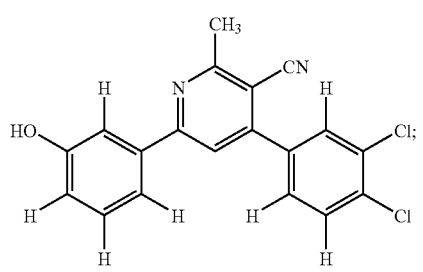
(FX58)
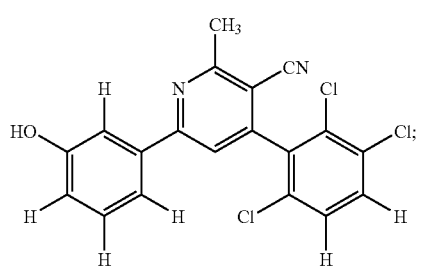
(FX59)
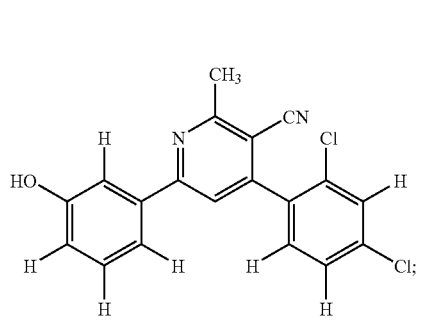

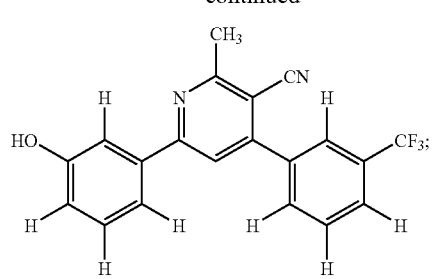
(FX60)

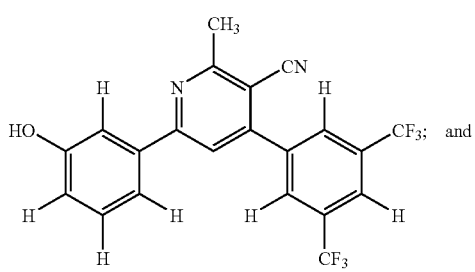
(FX61)

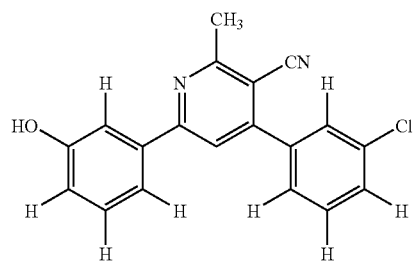
(FX62)

In another aspect, the present invention provides combinatorial libraries of compounds, including candidate compounds for screening microbial activity including antibacterial activity. In an embodiment of this aspect of the present invention, the present invention provides one or more combinatorial libraries of chalcone compounds and/or derivative thereof having any one of the formulas (FX1-FX34). In an embodiment of this aspect of the present invention, the present invention provides one or more combinatorial libraries of cyanopyridine compounds and/or derivatives thereof having any one of the formulas (FX35-FX62).

In another aspect, the present invention provides pharmaceutical and therapeutic preparations comprising one or more compounds of the present invention. Compounds of this invention and compounds useful in the methods of this invention include those of the above formulas FX1-FX62 and pharmaceutically-acceptable salts and esters of those compounds. In an embodiment, pharmaceutical and therapeutic preparations of the present invention comprising one or more chalcone or chalcone derivative compounds having the formula FX1, preferably for some applications compounds having any one of the formula FX2-FX16, and more preferably for some applications compounds having any one of the formula FX17-FX34. In an embodiment, pharmaceutical and therapeutic preparations of the present invention comprising one or more cyanopyridine or cyanopyridine derivative compounds having the formula FX35, preferably for some applications compounds having any one of the formula FX36-FX45, and more preferably for some applications compounds having any one of the formula FX46-FX62. Salts include any salts derived from the acids of the formulas herein which are acceptable for use in human or veterinary applications. The term esters refer to hydrolyzable esters of chalcone compounds, cyanopyridine compounds and/or derivatives of these of the present invention. Salts and esters of the compounds of the formulas herein are those which have the same or similar pharmaceutical or therapeutic (human or veterinary) properties as the chalcone compounds, cyanopyridine compounds and/or derivatives of these of the present invention. Therapeutic and pharmaceutical preparations of the present invention comprise one or more of the compounds of the present invention in an amount or in a combined amount effective for obtaining the desired therapeutic benefit. Therapeutic and pharmaceutical preparations of the invention optionally further comprise a pharmaceutically acceptable carrier as know in the art.

In another aspect, the present invention provides a method of treating an infectious disease comprising administering to a patient in need a composition comprising a compound of the present invention. In an embodiment, the infectious disease relates to an infectious agent comprising a bacterium. In an embodiment, the bacteria are Gram-positive bacteria. In a specific embodiment, the bacteria include one or more of *Bacillus, Listeria, Staphylococcus, Streptococcus, Enterococcus, Corynebacterium, Propionibacterium* and *Clostridium*. In a specific embodiment, the bacteria are one or more selected from the group consisting of *S. aureus, S. epidermidis* and *B. subtilis*. In a specific embodiment, the bacteria are one or more drug resistant bacteria. In an embodiment of this aspect, a method of the present invention comprises the step of administering a therapeutically effective amount of a chalcone compound or derivative thereof having the formula (FX1-FX34) or a pharmaceutical formulation thereof to the patient in need, preferably for some applications one or more compounds having any one of the formulas FX2-FX16, and more preferably for some applications one or more compounds having any one of the formulas FX17-FX34. In an embodiment of this aspect, a method of the present invention comprises the step of administering a therapeutically effective amount of a cyanopyridine compound or derivative thereof having the formula (FX35) or a pharmaceutical formulation thereof to the patient in need, preferably for some applications one or more compounds having any one of the formulas FX36-FX45, and more preferably for some applications one or more compounds having any one of the formulas FX46-FX62.

In another aspect, the present invention provides methods of inhibiting growth of bacteria. In a specific embodiment of this aspect, a method of the present invention comprises the step of contacting the bacteria with a effective amount of one or more chalcone or chalcone derivative compounds having the formula FX1, preferably for some applications one or more compounds having any one of the formulas FX2-FX16, and more preferably for some applications one or more compounds having any one of the formulas FX17-FX34. In a specific embodiment of this aspect, a method of the present invention comprises the step of contacting the bacteria with a effective amount of one or more cyanopyridine or cyanopyridine derivative compounds having the formula FX35, preferably for some applications one or more compounds having any one of the formulas FX36-FX45, and more preferably for some applications one or more compounds having any one of the formulas FX46-FX62. In an embodiment, the bacteria are Gram-positive bacteria. In a specific embodiment, the bacteria include one or more of *Bacillus, Listeria, Staphylococcus, Streptococcus, Enterococcus, Corynebacterium, Propionibacterium* and *Clostridium*. In a specific embodiment, the bacteria are one or more selected from the group consisting of *S. aureus, S. epidermidis* and *B. subtilis*. In a specific embodiment, the bacteria are one or more drug resistant bacteria.

Methods of inhibiting bacteria of the present invention include methods useful for treatment of a subject (human or veterinary) and also include methods useful for inhibiting bacteria outside of a subject, such as use for sterilization and disinfection.

In an other aspect the present invention provides methods of synthesizing the compounds of the present invention, including methods of synthesizing chalcones and derivatives thereof, cyanopyridines and derivatives thereof, alkylpyrimidines and derivatives thereof, and aminopyrimidines and derivatives thereof. In an embodiment, for example, the present invention includes methods of synthesizing compounds using scheme 1 and the scheme provided in FIG. 1A.

In another aspect, the present invention provides methods of screening compounds, classes of compounds and combinatorial libraries of compounds for antimicrobial activity, including antibacterial activity. In an embodiment of this aspect, a method for screening a plurality of candidate compounds for antimicrobial activity of the present invention comprises the steps of: (i) providing a spatially-addressed array of the candidate compounds supported by a first unitary substrate, wherein the candidate compounds are individually addressed to selected positions of the substrate via linkers; (ii) contacting a microbial culture with the array or with a portion of the array transferred to a second unitary substrate in a manner retaining the relative positions of candidate compounds in the array, whereby candidate compounds having antimicrobial activity exhibit a zone of inhibition in the microbial culture; and (iii) identifying one or more positions in the array or transferred portion of the array corresponding to one or more candidate compounds exhibiting zones of inhibition. Optionally, methods of this aspect of the present invention further comprise the step of transferring the portion of the array to a second unitary substrate in a manner retaining the relative positions of candidate compounds in the array. In some embodiments, this transfer step is carried out multiple times so as to generate a plurality of array samples for screening. In a specific embodiment, the invention provides a method of screening the plurality of candidate compounds for antibacterial activity wherein the microbial culture is a bacterial culture. Alternatively, the invention provides a method of screening the plurality of candidate compounds for antifungal activity wherein the microbial culture is a fungal culture. Useful arrays in the present methods include macroarrays and microarrays of candidate compounds.

The present invention includes methods using overlay assaying techniques wherein a microbial culture is provided in contact with the entire array or a portion thereof to provide effective, nearly simultaneous readout of the activities of a large number of candidate compounds. Overlay assaying techniques useful in these methods include, but are not limited to, techniques wherein an agar medium inoculated with bacteria is provided in contact with the array to provide screening of the antibacterial activities of candidate compounds of the array.

In some embodiments the methods of the present invention further comprises the step of cleaving the linkers prior to the step of contacting the bacterial culture with the array or transferred portion of the array. This additional step facilitates achieving effective and biologically significant contact between compounds of the array and the microbial culture. Preferably, the step of cleaving the linkers connecting compounds of the array and the substrate is carried out in a way that does not substantially disrupt the position of individual compounds of the array on the substrate. In some embodiments, the screening methods further comprises the step of transferring the portion of the array to a second unitary substrate in a manner retaining the relative positions of candidate compounds in the array. Exemplary means of transferring a portion of the array in these embodiments include, but are not limited to, overlay transfer methods, such as positioning cleaved arrays between a solvent saturated surface and one or more dry cellulose sheets. An advantage of this embodiment of the present invention is that a single array may be used to generate a plurality of "copies" (i.e., transferred portions of the array which retain the spatially address nature of the compounds in the array) that can be screened to provide replicated assays.

Screening methods of the present invention may further comprise a number of optionally steps. In an embodiment, for example, the method further comprises incubating the microbial culture, such as a bacteria culture, in contact with the array or transferred portion of the array. In an embodiment, for example, the method further comprises the step of measuring a zone of inhibition parameter exhibited by one or more candidate compounds of the array. Useful zone of inhibition parameters for the present methods include, but are not limited to, a diameter of inhibition, a radius of inhibition, and an area of inhibition. In an embodiment, for example, the method further comprises the step of contacting the bacterial culture with a visualization agent, whereby the visualization agent is capable of differentiating between zones of inhibition and zones of no activity. Useful visualization agents include, but are not limited to, redox indicators such as triphenyl tetrazolium chloride capable of providing clear and reproducible visualization of areas of live and dead bacteria for the measuring one or more zone of inhibition parameters.

Preferably for many applications, candidate compounds are linked to the substrate in a manner such that they can be non-destructively cleaved from the first unitary substrate. The choice of linker and mechanism of cleavage from the substrate many affect the composition of candidate compounds released from the substrate via cleavage reactions. In some instances, for example, cleavage of linkers results in candidate compounds having one or more functional groups, such as OH and alkoxyl groups, introduced by the linking chemistry. In some embodiments, linkers connecting the candidate compounds to the substrate are acid cleavable, base cleavable, nucleophile cleavable; electrophile cleavable, oxidant cleavable, reductant cleavable, or photocleavable.

Substrates useful in the present methods include planar (2D) substrates and three-dimensional substrates. Three-dimensional substrates include beaded materials, such as beaded cellulose, and other useful materials such as tissue engineering scaffolds. A range of substrate compositions are useful in the present invention including, but not limited to, cellulose substrate, nylon substrate, polypropylene substrate, polycarbonate substrate, glass substrate, gold substrate, silicone substrate or amorphous carbon substrate. In some embodiments, the unitary substrate supporting the arrays of this invention is a planar substrate.

In some methods candidate compounds are synthesized in an array bound to a surface. The candidate compounds are typically linked to the surface by a linker group, preferably for many screening applications a cleavable linker group. Linker groups include those that are cleavable, e.g., chemically or photochemically, such that candidate compounds can be non-destructively removed (e.g., cleaved) from the substrate surface. The methods of this invention are particularly useful when practiced with macroarrays. However, the methods can be practiced employing microarrays.

In some screening methods of this aspect of the present invention, candidate compounds are chalcone or chalcone derivative compounds having any one of the formulae FX1, preferably for some applications having formulas FX2-FX16, and more preferably for some applications having formulas FX17-FX34. In some screening methods of this aspect of the present invention candidate compounds are cyanopyridine or cyanopyridine derivative compounds having the formula FX35, preferably for some applications compounds having any one of the formulas FX36-FX45, and more preferably for some applications compounds having any one of the formulas FX46-FX62.

(B) Building blocks. Hydroxyacetophenones (A-C, top) and benzaldehydes (a-w, bottom) used in the construction of chalcone (3), 2-amino-3-cyanopyridine (5), and pyrimidine (7, 8) macroarrays.

Figure 2:
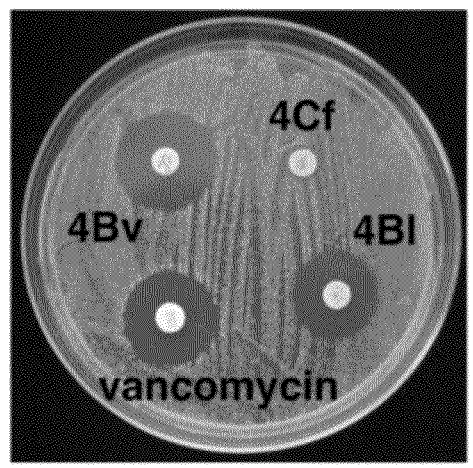
Figure 2:
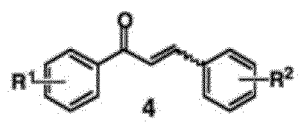
Figure 2:
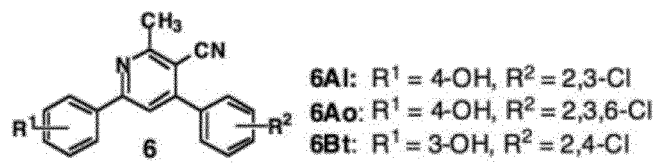
Figure 2:
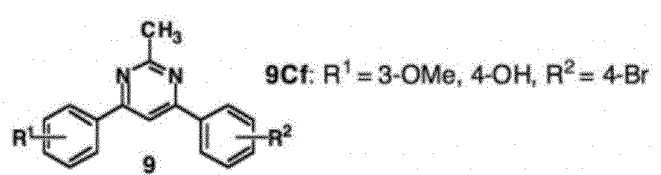
Figure 2:
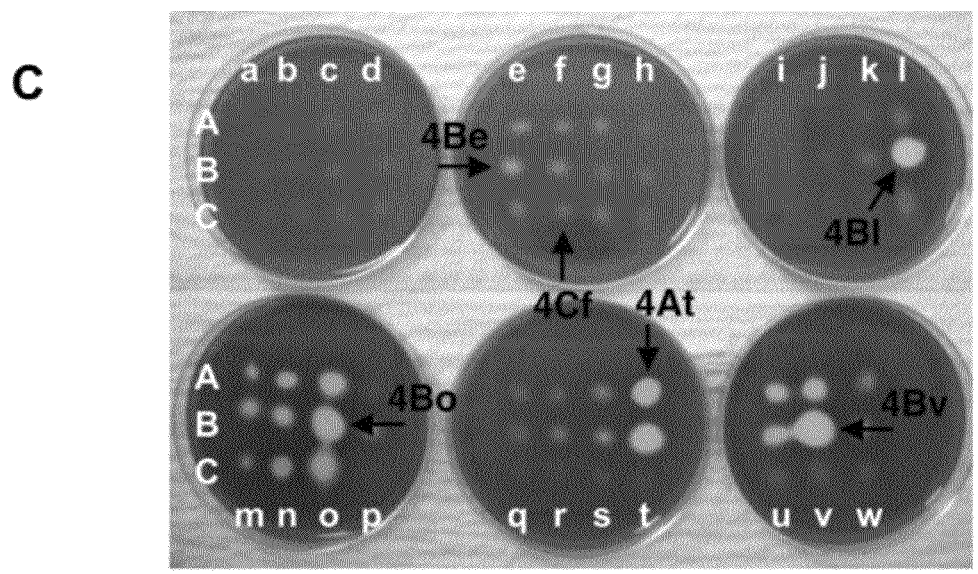
Figure 2:
Figure 2:
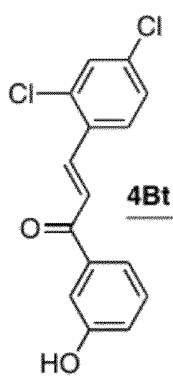
Figure 2:
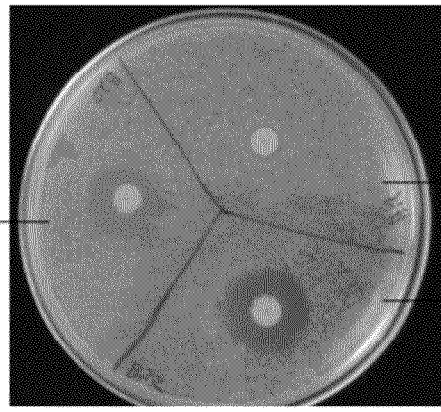
Figure 2:
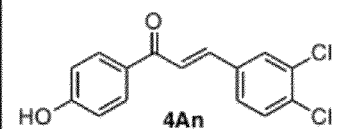
Figure 2:
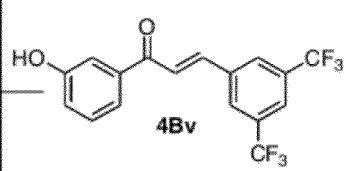
Figure 2:
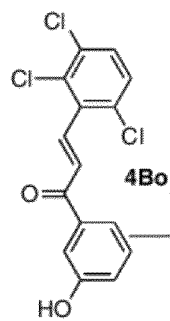
Figure 2:
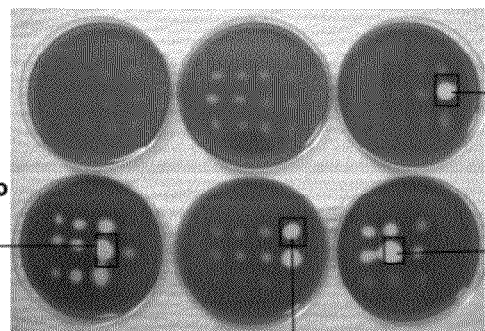
Figure 2:
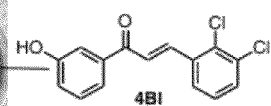
Figure 2:
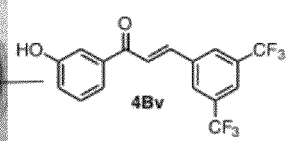
Figure 2:
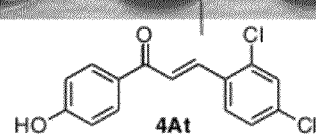

FIG. 2. Representative Antibacterial Assays Performed on Macroarrays and Active Compounds Identified. Strain: *S. aureus* ATCC 10390. Scale: Petri dish diameter=9 cm.

(A) Disk diffusion assay performed on compound spots punched out from a cleaved chalcone macroarray (3) and vancomycin standard (loadings=30 µg/spot). Zones of inhibition (in mm): 4Bl=19; 4Bv=22; 4Cf=<1; vancomycin=20.

(B) Antibacterial compounds identified in assays conducted on macroarrays.

(C) Agar overlay TTC assay of a cleaved 69-member chalcone macroarray (3) divided into six sub-arrays. The array building block grid and compounds displaying a range of activities are indicated.

(D) Agar overlay TTC assay of compound 6Ao applied to planar cellulose in the shape of The University of Wisconsin—Madison "Motion W" insignia. depicts representative bacterial agar overlay assay performed on a 69-member chalcone macroarray divided into six 12-member arrays. Areas of bacterial growth are colored; areas of no growth remain white.

(E) provides Kirby-Bauer disk diffusion assay for certain compounds of this invention.

(F) depicts representative bacterial agar overlay assay performed on a 69-member chalcone macroarray divided into six 12-member arrays. Areas of bacterial growth are colored; areas of no growth remain white.

Figure 3:
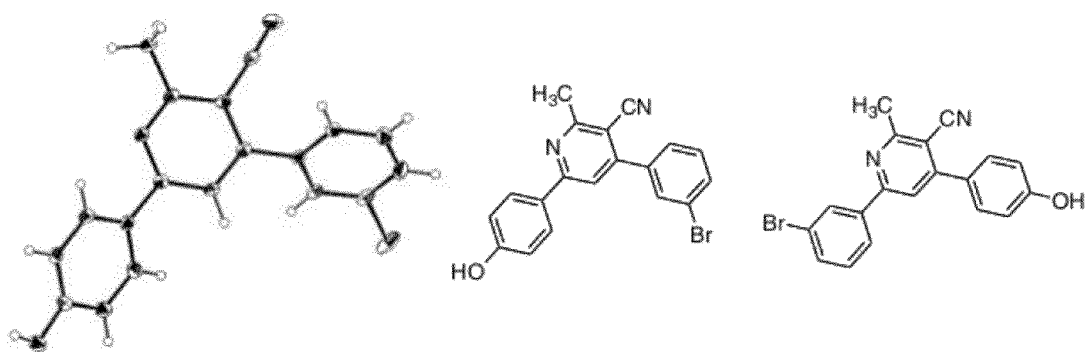

FIG. 3. Left: ORTEP diagram of solid-state structure of 6Ae. Selected crystallographic data: a=13.0350 Å, b=7.7420 Å, c=19.2670 Å, α=90.0°, β=93.511°, γ=90.0°, space group=P$_{2(1)/n}$, calculated density=1.449 g/cm$^3$, volume=1940.70 Å$^3$, R(F)=0.033, R(F$^2$)=0.043, R$_w$(F$^2$)=0.094, goodness of fit=1.006. Center: structure of 6Ae displayed in the same orientation. Right: structure of alternate regioisomer of 6Ae.

Figure 4:
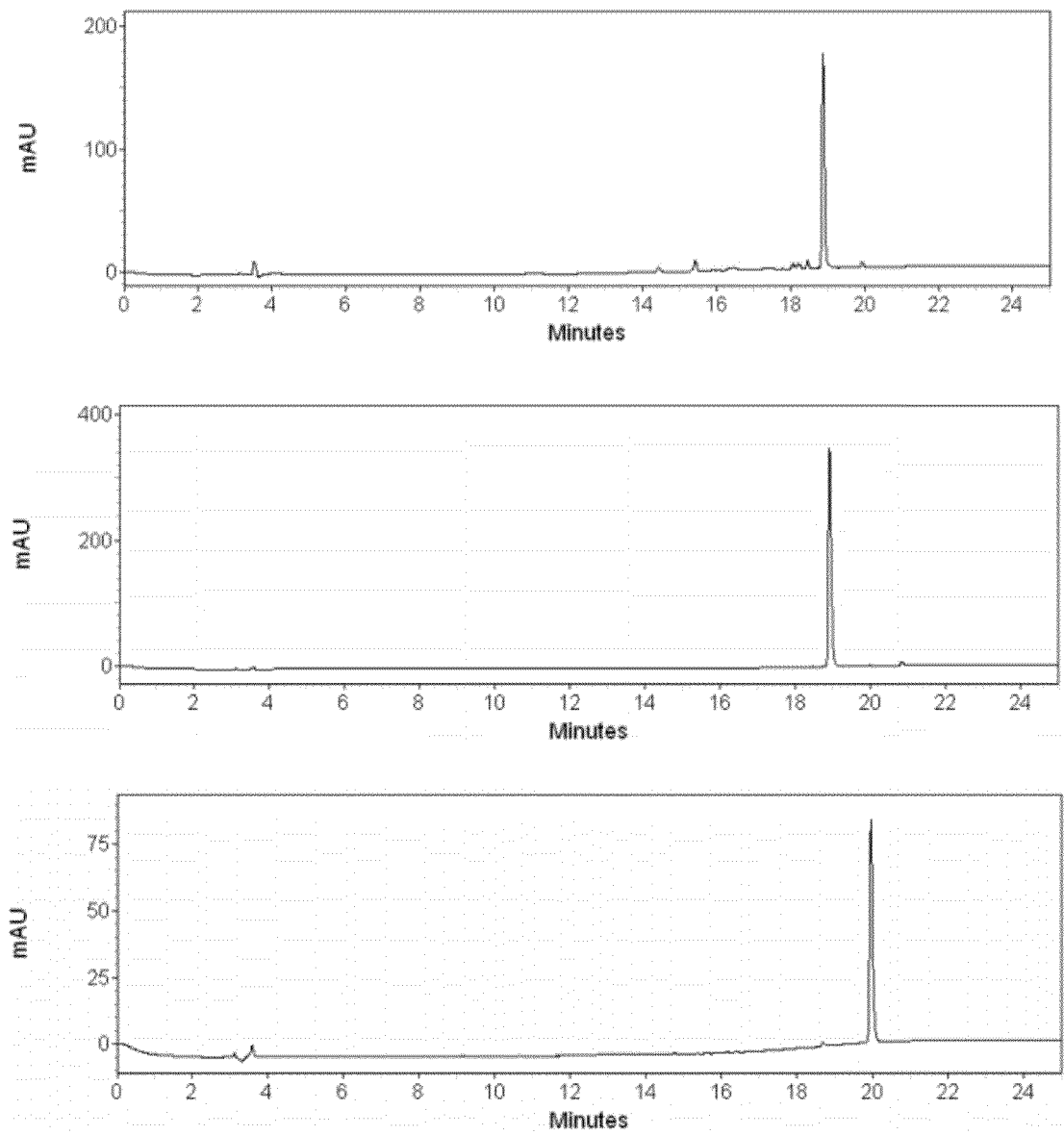

FIG. 4. HPLC traces of cyanopyridine 6Ae synthesized on a macroarray (top), cyanopyridine 6Ae synthesized in solution (middle), and an authentic sample of the alternate regioisomer of 6Ae (bottom). UV detection at 254 nm.

Figure 5:
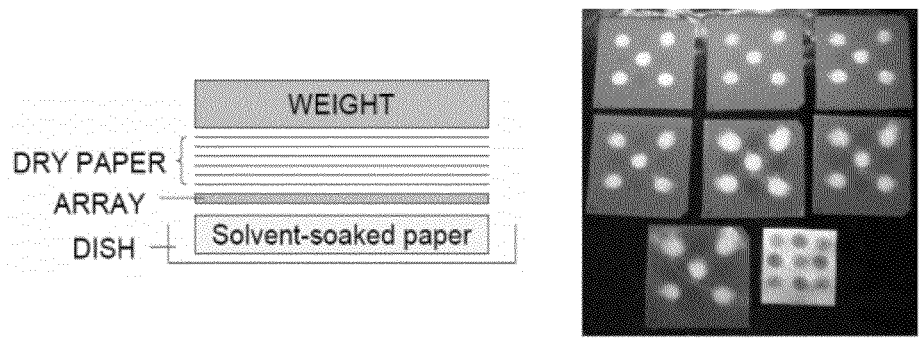

FIG. 5. Macroarray transfer. Left: Schematic of macroarray transfer method set-up. Right: Image of a representative original macroarray (lower right) and seven copies under UV light. Larger spots of fluorescent compounds were used here for image clarity.

Figure 6:
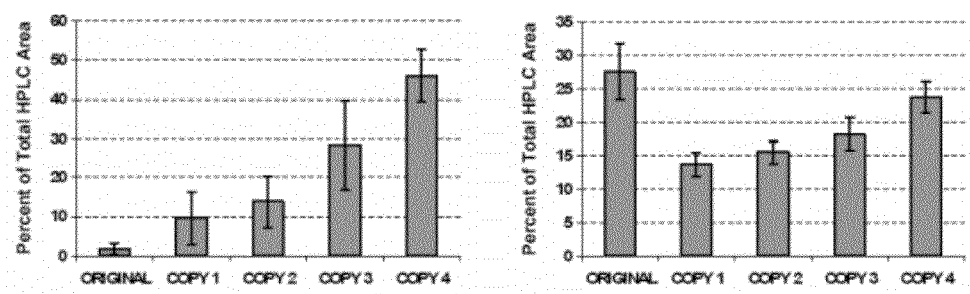

FIG. 6. Compound distribution on macroarray copies. Left: Concentration gradient of chalcone 4Be distributed on four macroarray copies after transfer; error bars show variability due to location on array. Right: Concentration gradient for five different chalcones 4 distributed on four copies after macroarray transfer; error bars show variability due to structural differences between chalcones.

Figure 7:
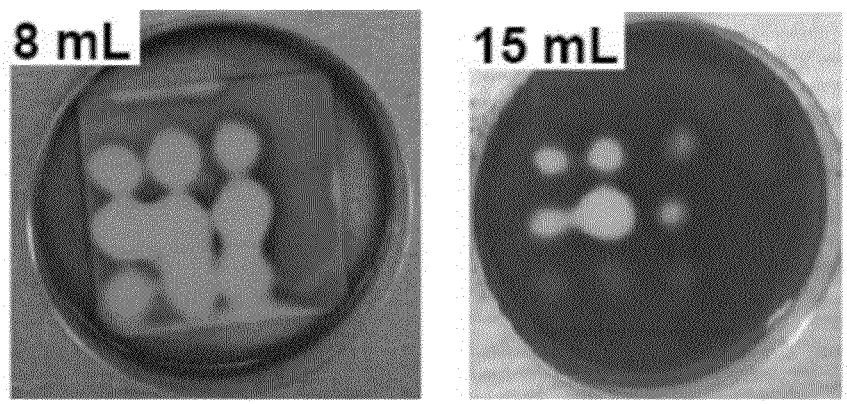

FIG. 7. Image of macroarrays overlaid with different volumes of agar. Compound 4Bv was clearly identified as the most active "hit" in the image on the right where 15 mL agar was used.

Figure 8:
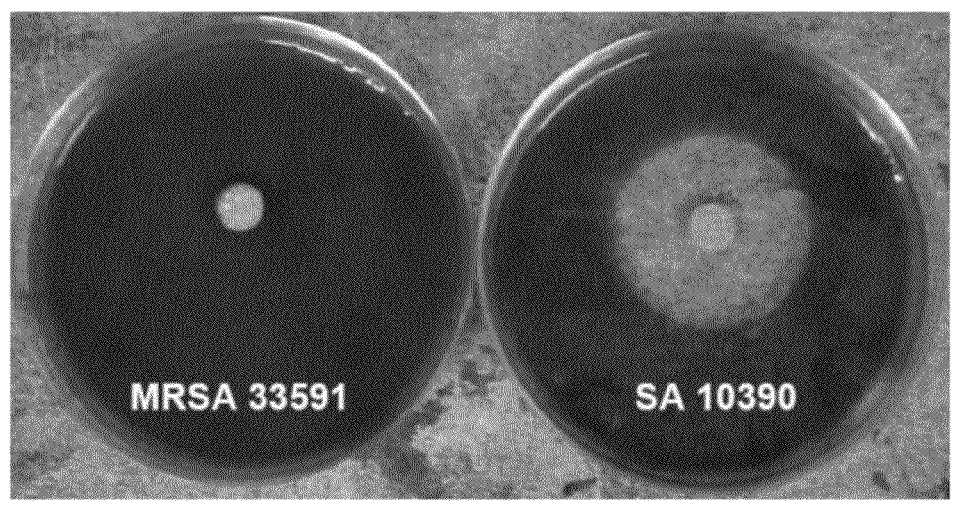

FIG. 8. Effects of methicillin susceptibility disks against methicillin-resistant *S. aureus* ATCC 33591 (MRSA, left) and *S. aureus* ATCC 10390 (SA, right) visualized using the agar overlay TTC assay. Zone of inhibition for SA=39 mm. Petri dish diameter=9 cm.

Figure 9:
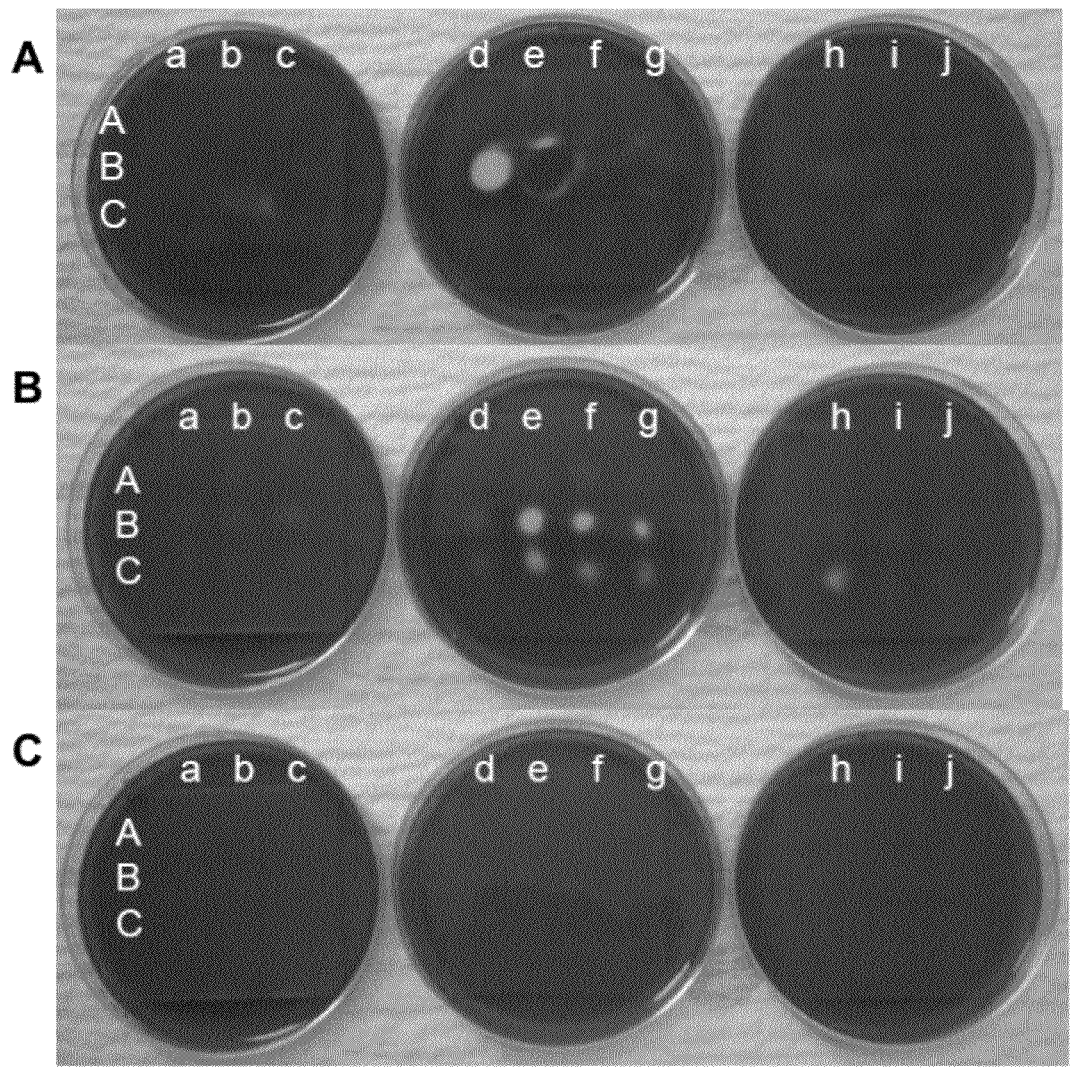
Figure 10:
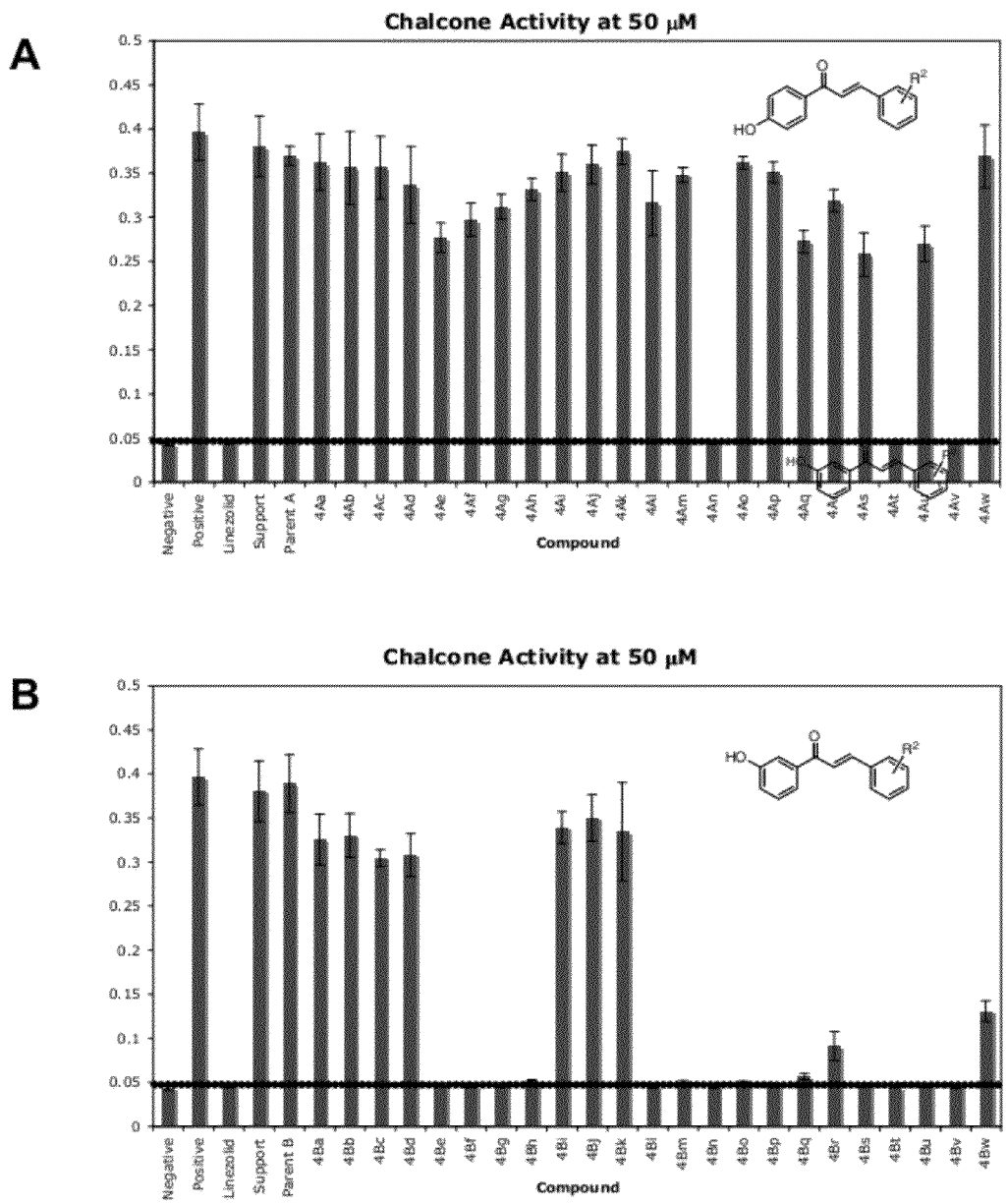
Figure 10:
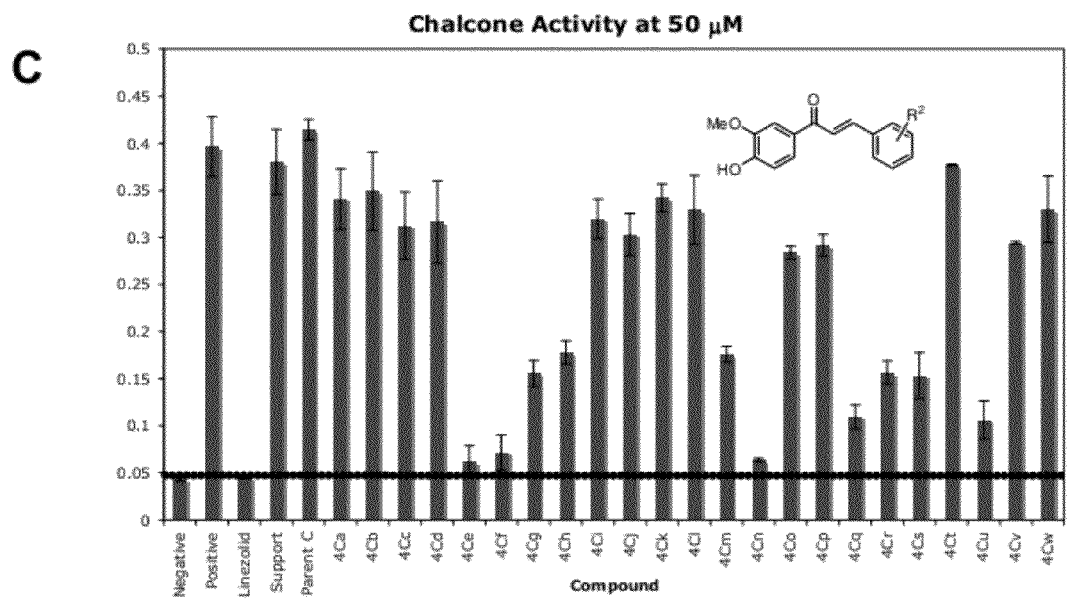
Figure 10:
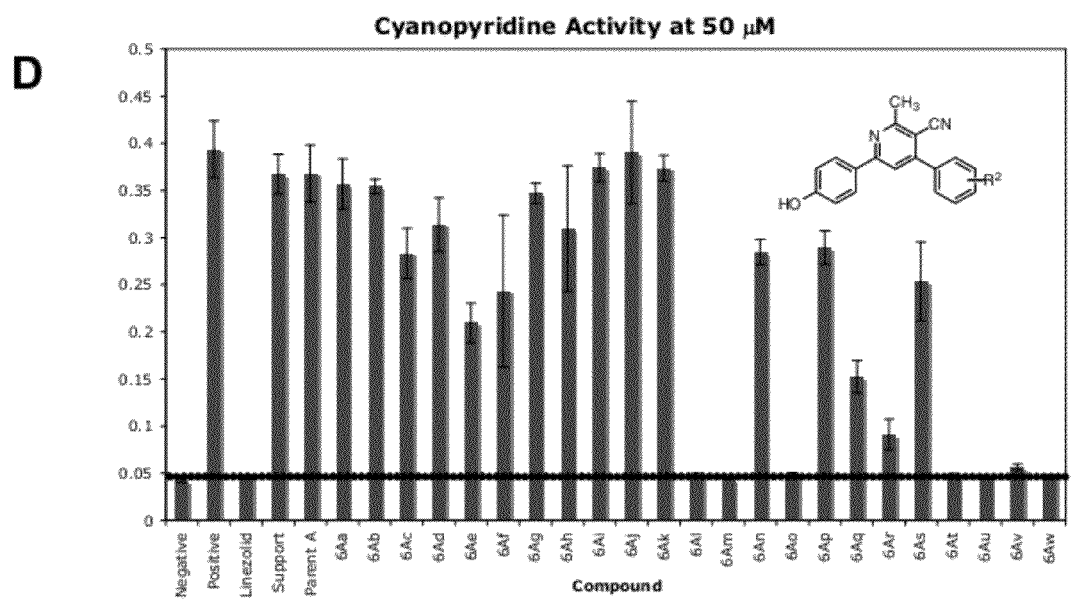
Figure 10:
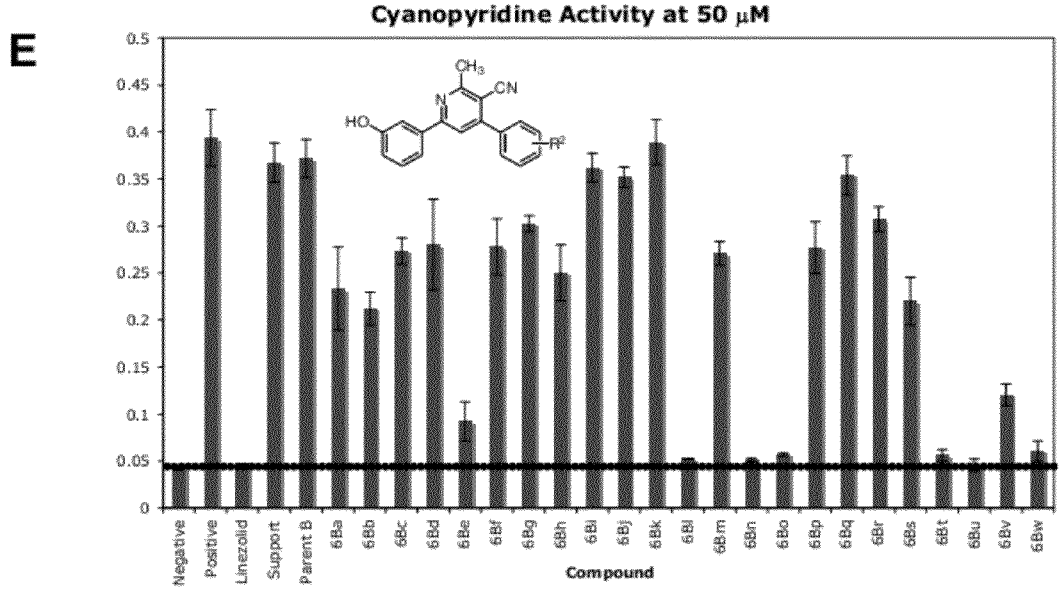
Figure 10:
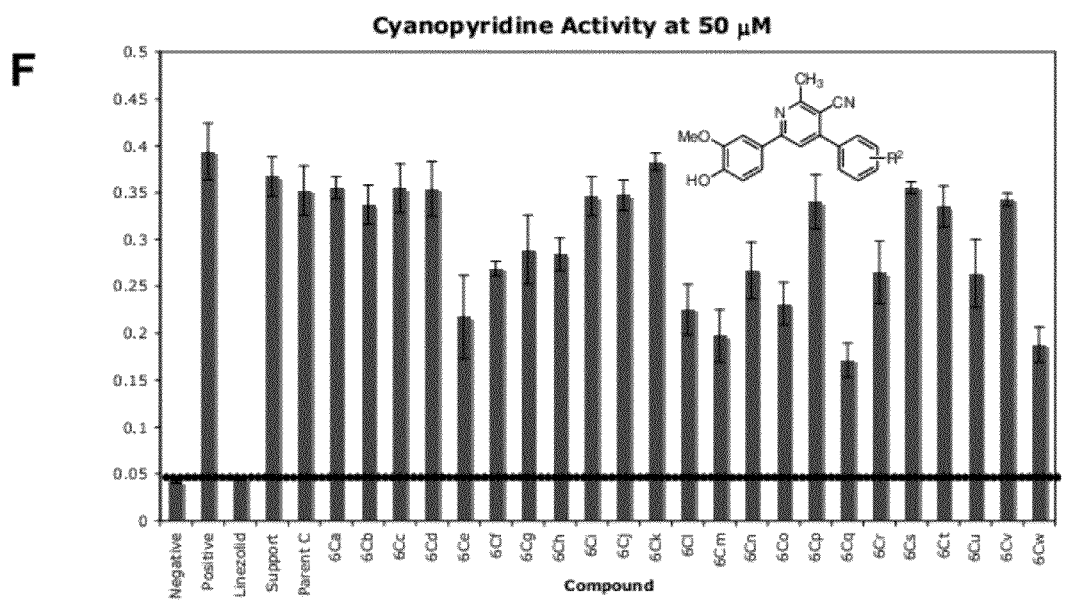
Figure 10:
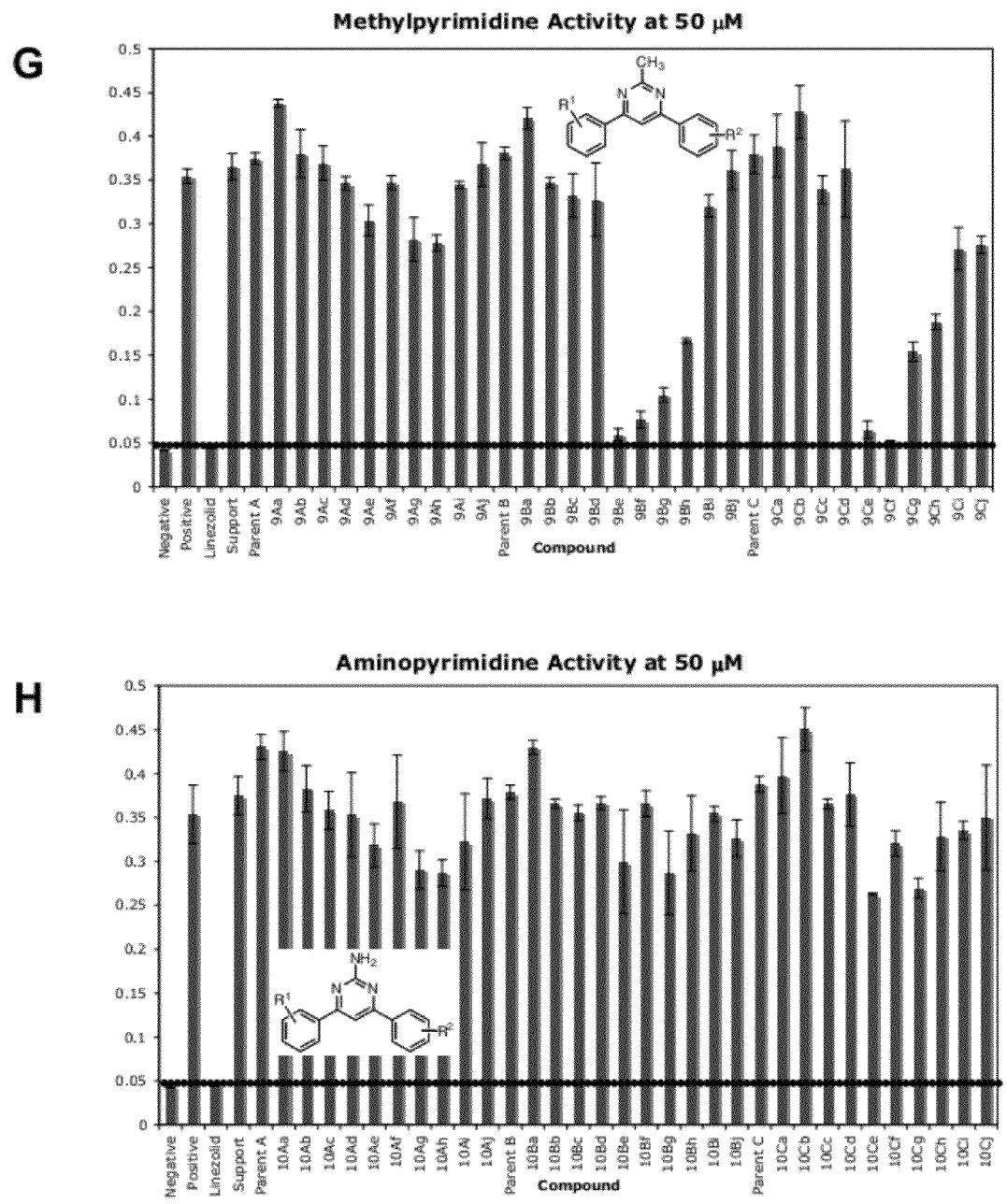

FIG. 9. Representative agar overlay TTC assay data for copies of macroarrays 6, 9, and 10. A: Cyanopyridine copy (6). B: Methylpyrimidine copy (9). C: Aminopyrimidine copy (10). The array building block grid is indicated. Petri dish diameter=9 cm.

FIG. 10A-H. Estimated MIC assay data for macroarray compounds.

Figure 11:
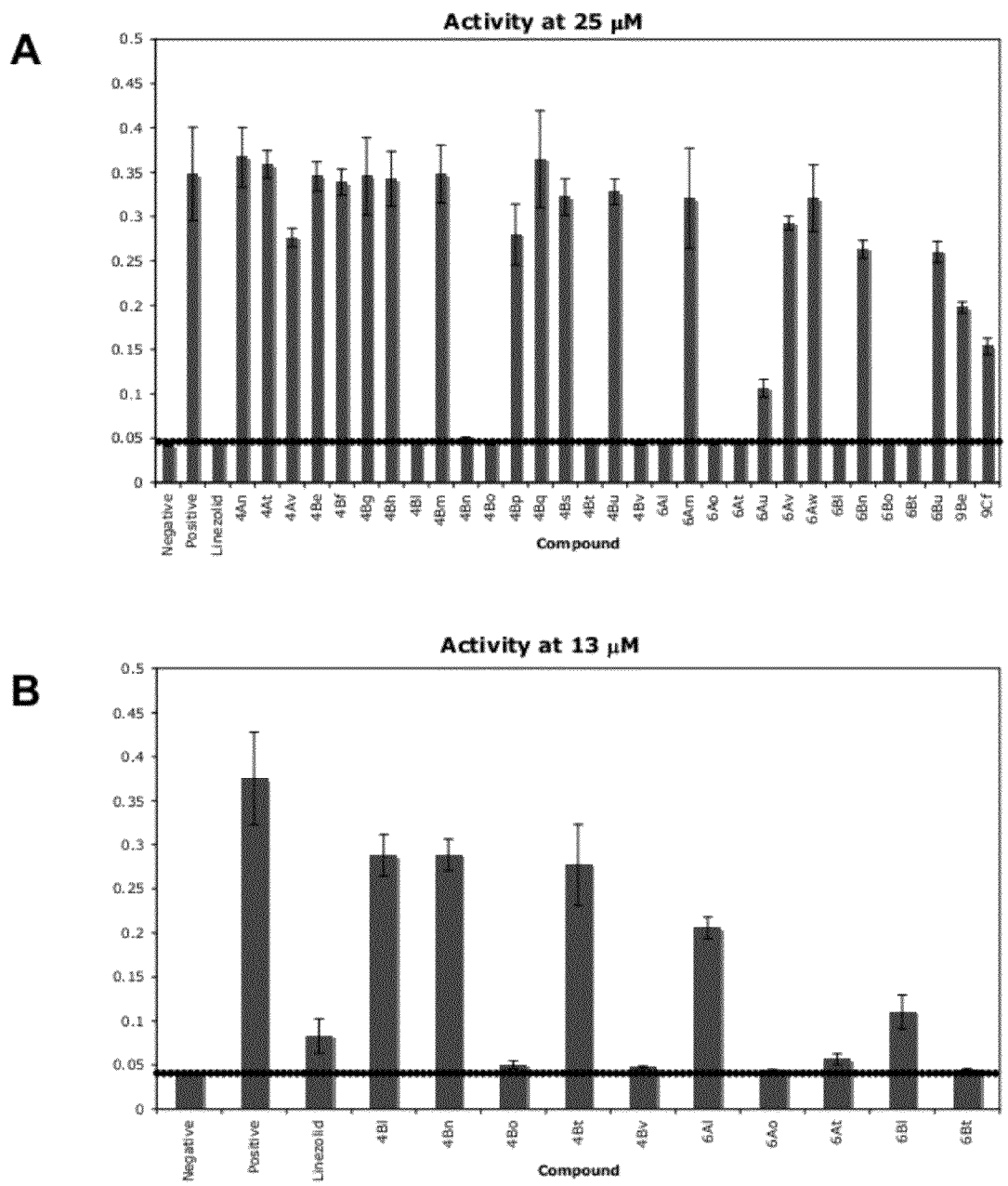

FIGS. 11A&B. Estimated MIC assay data for active macroarray compounds (25 and 13 µM).

Figure 12:
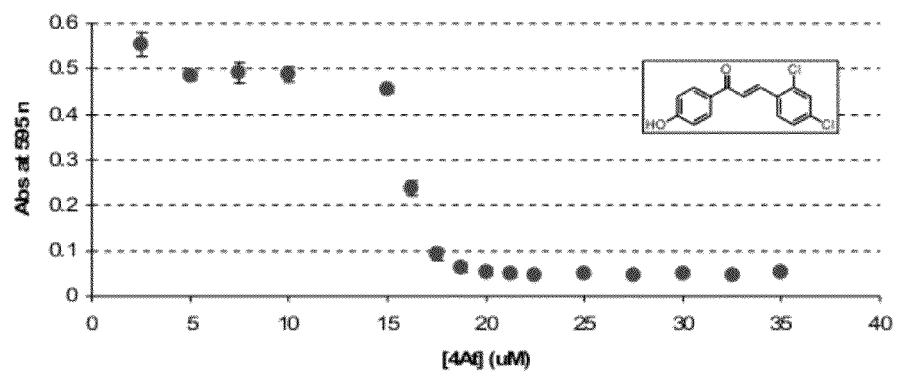
Figure 12:
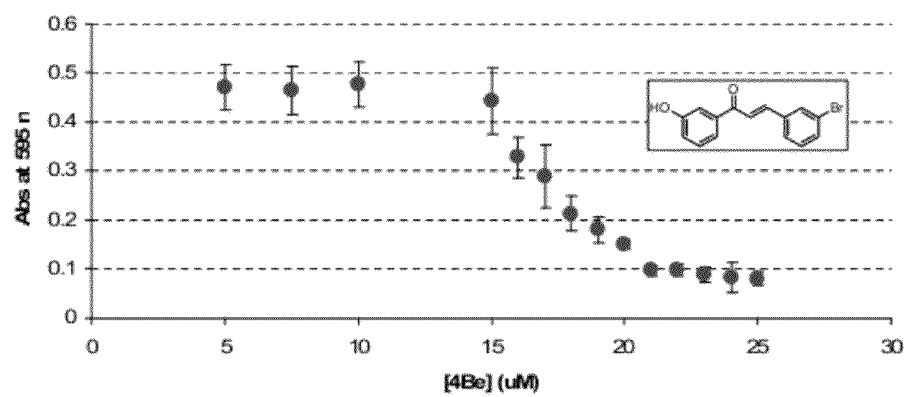
Figure 12:
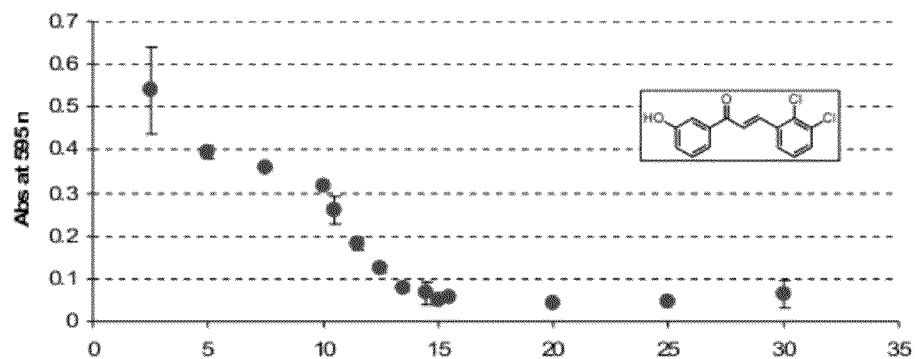
Figure 12:
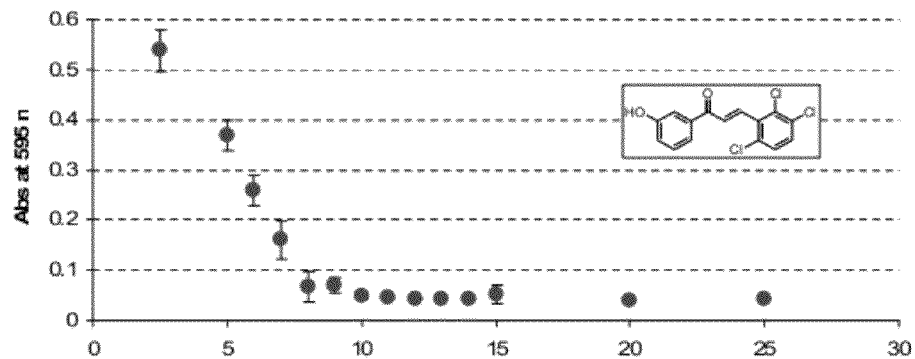
Figure 12:
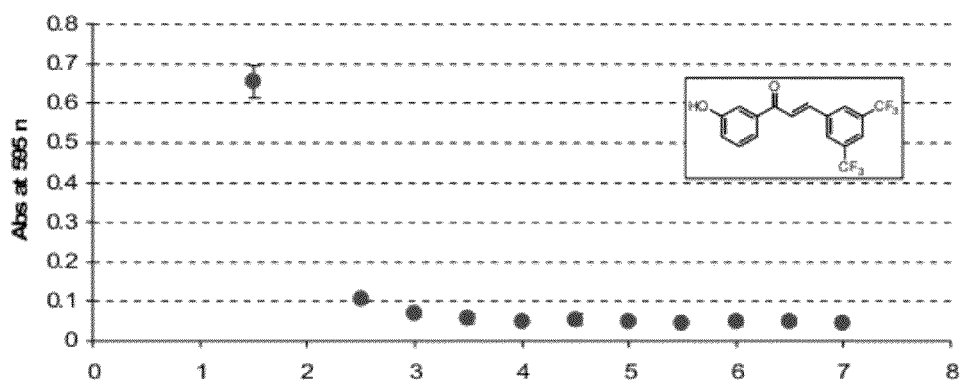
Figure 12:
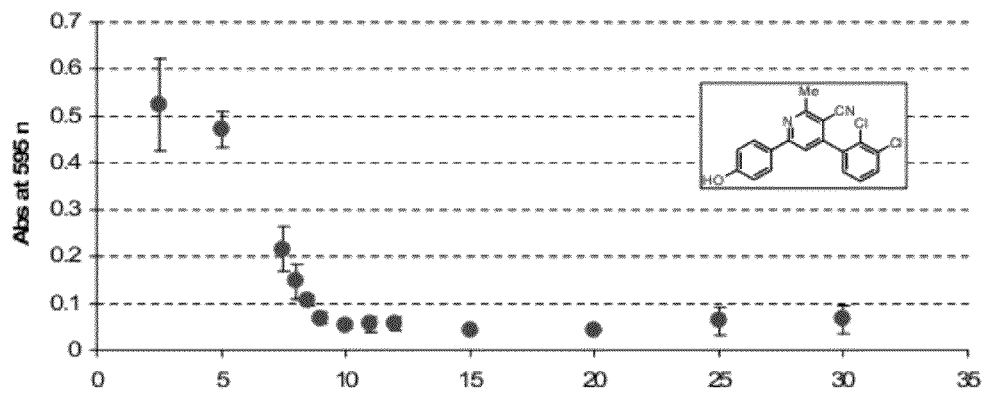
Figure 12:
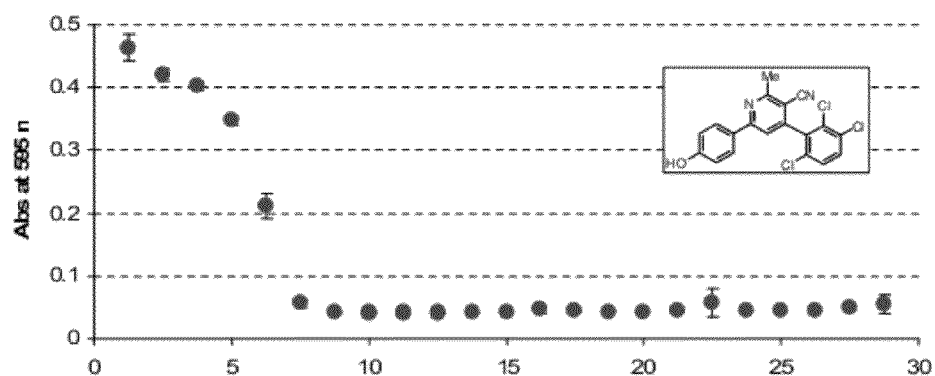
Figure 12:
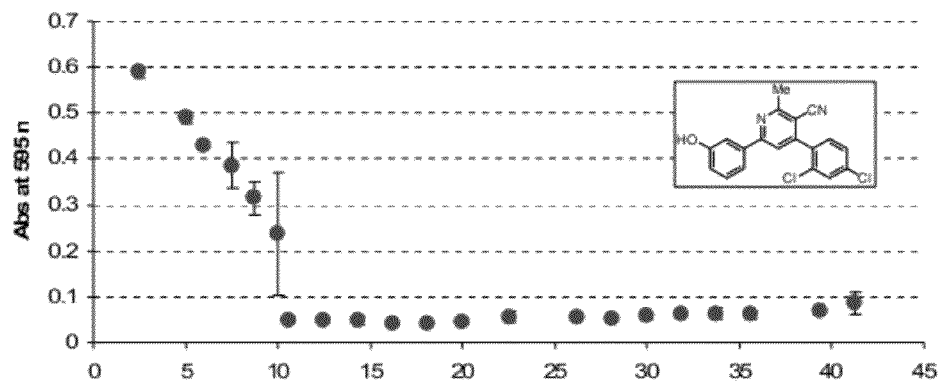
Figure 12:
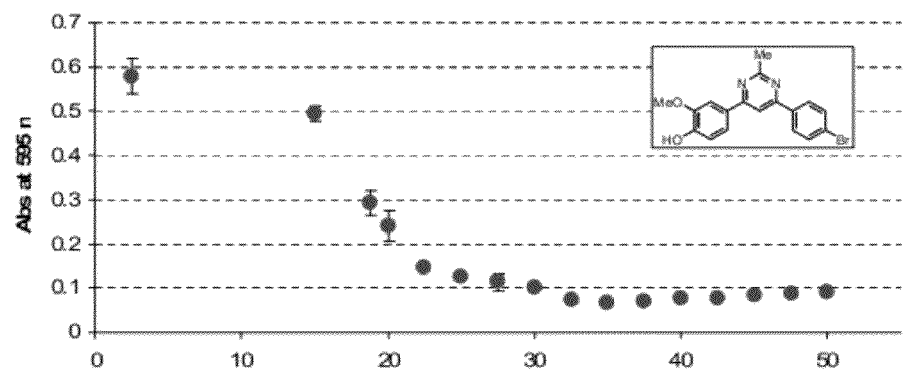
Figure 12:
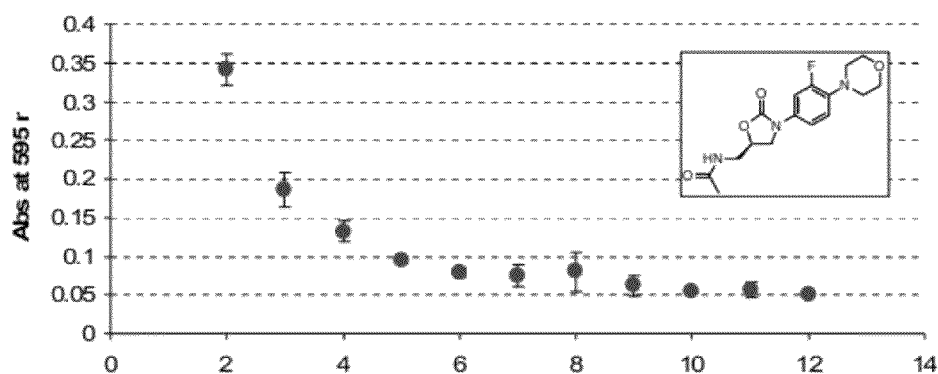
Figure 12:
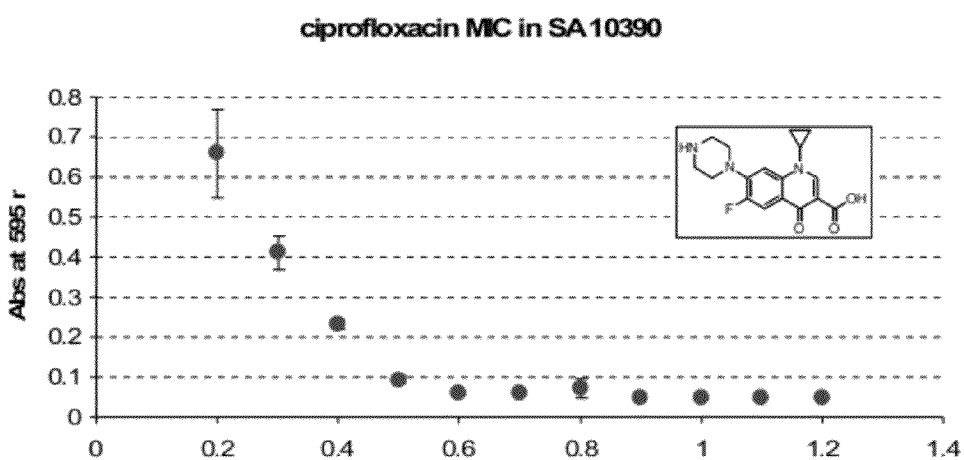
Figure 12:
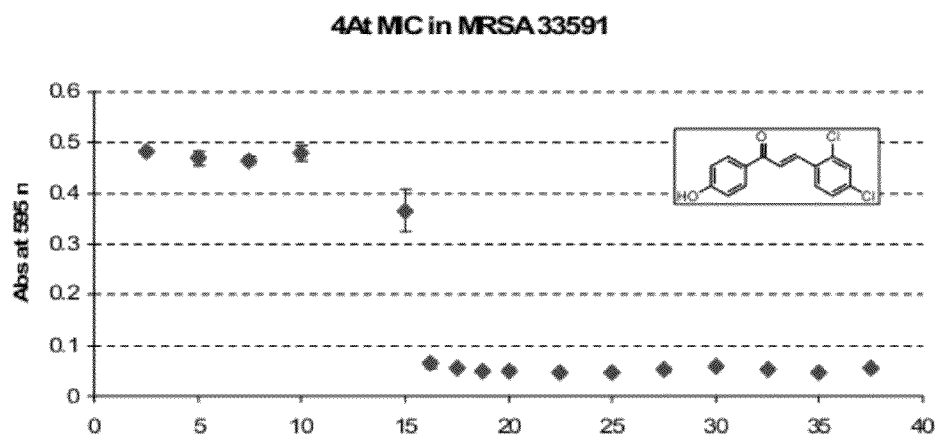
Figure 12:
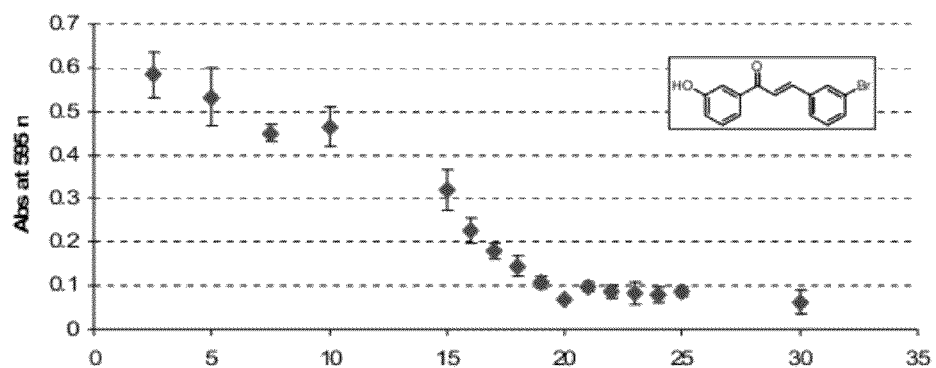
Figure 12:
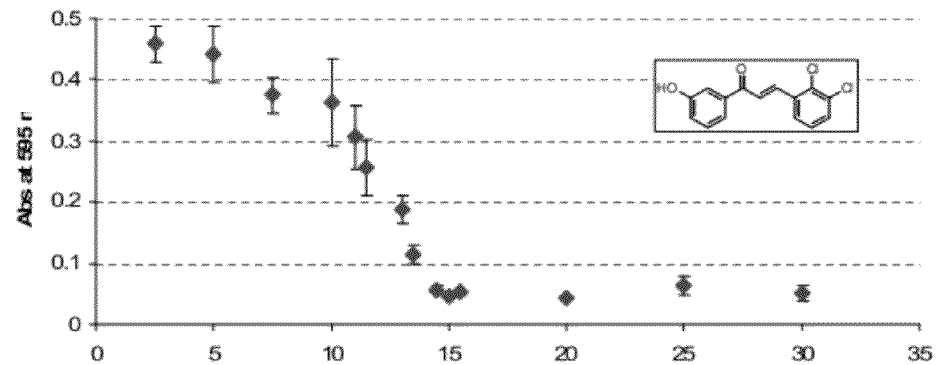
Figure 12:
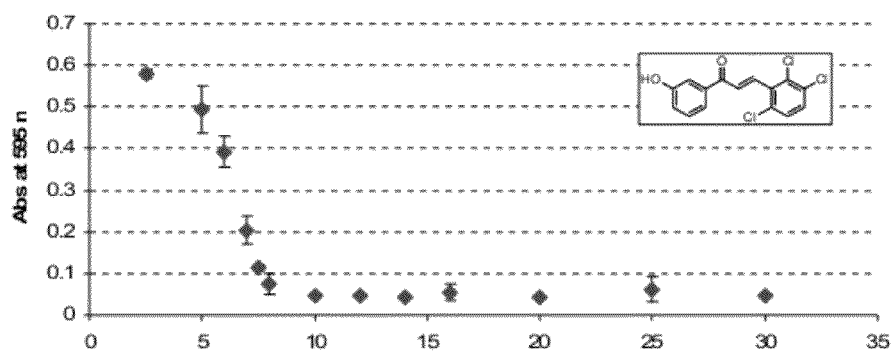
Figure 12:
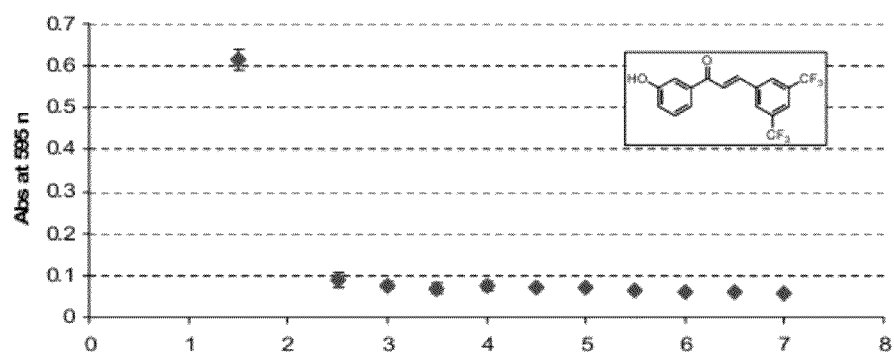
Figure 12:
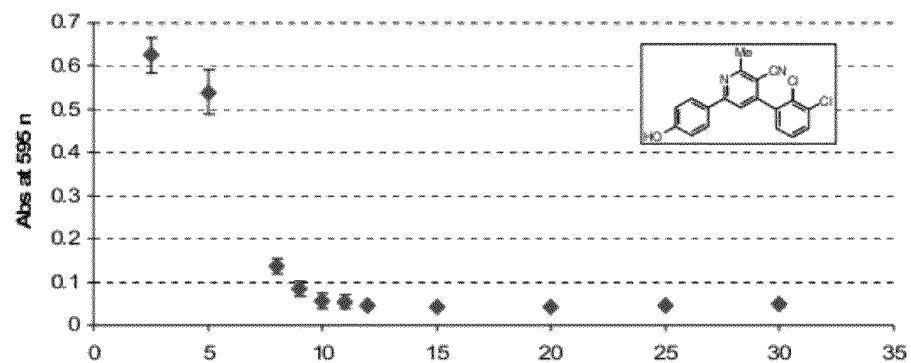
Figure 12:
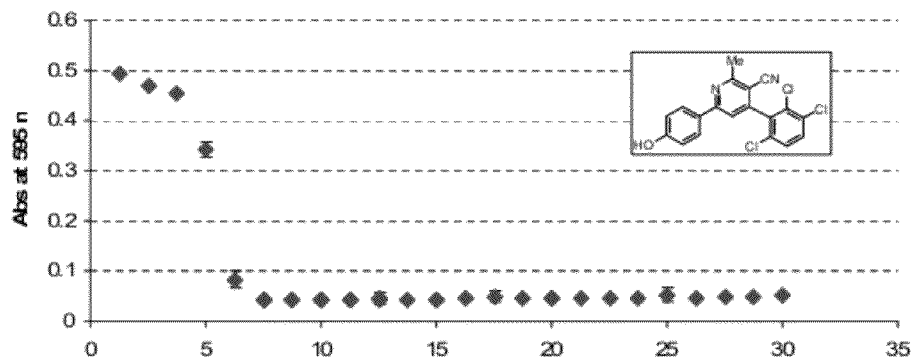
Figure 12:
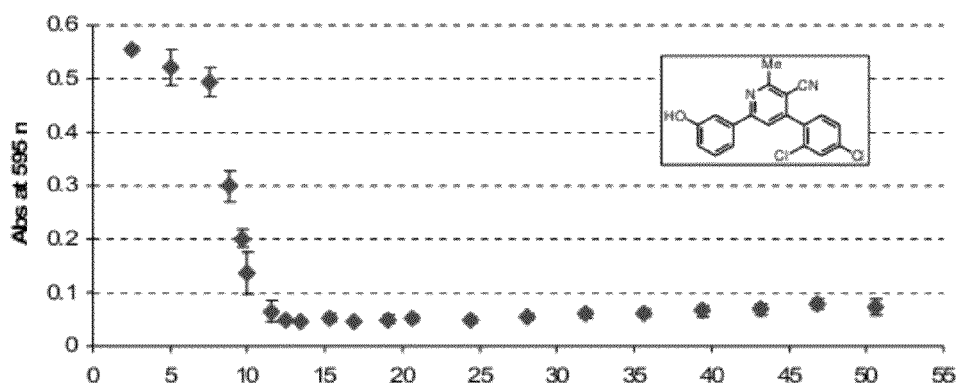
Figure 12:
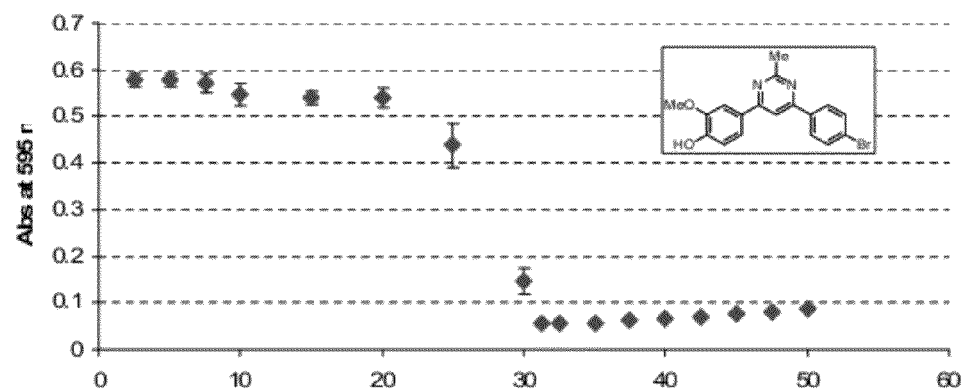
Figure 12:
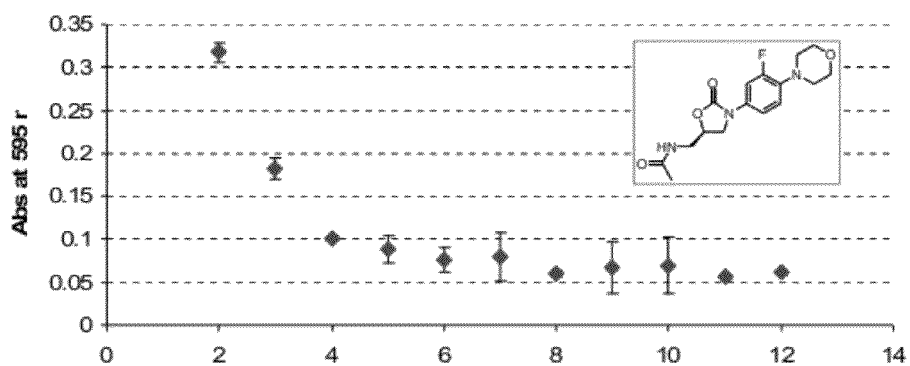
Figure 12:
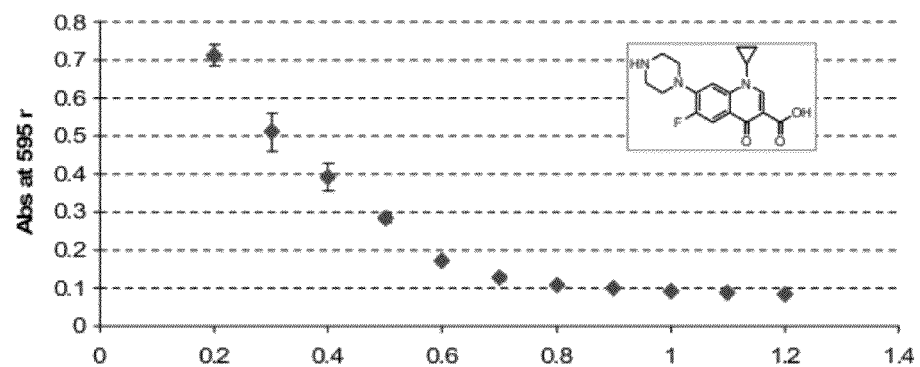
Figure 13:
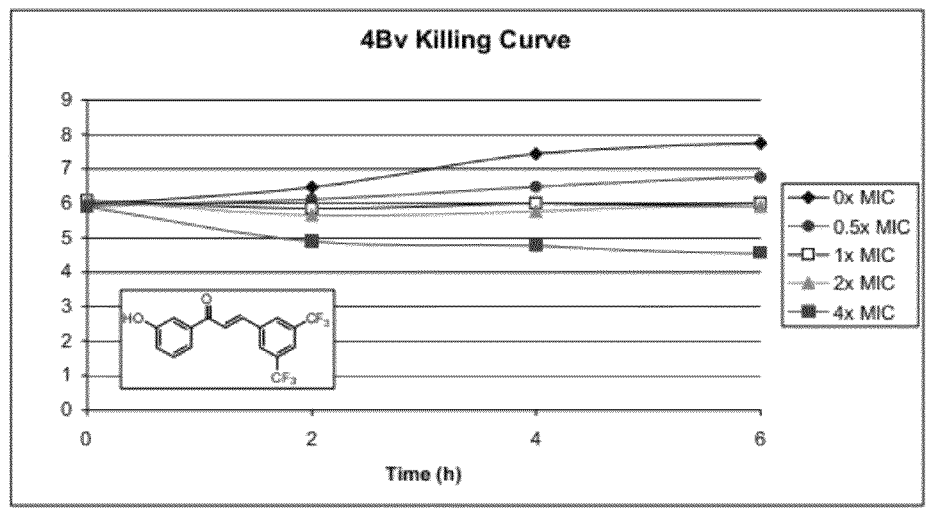
Figure 13:
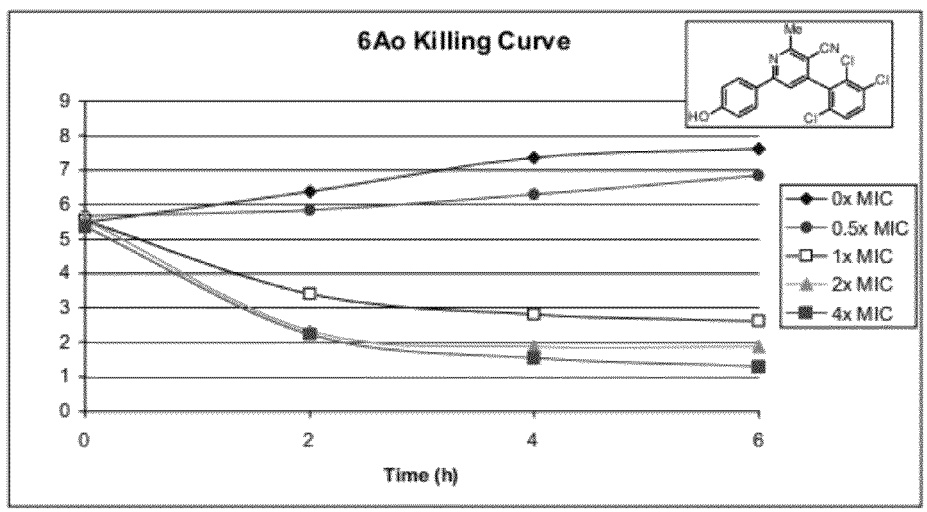
Figure 13:
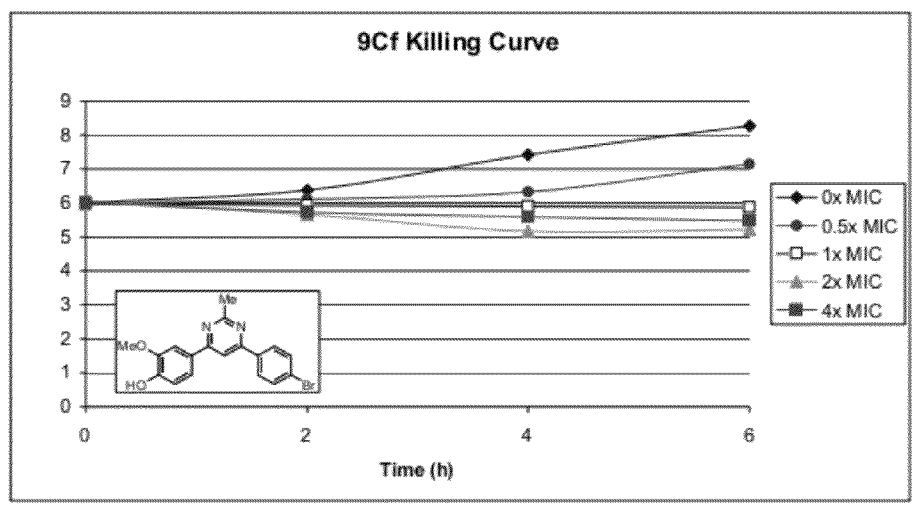
Figure 13:
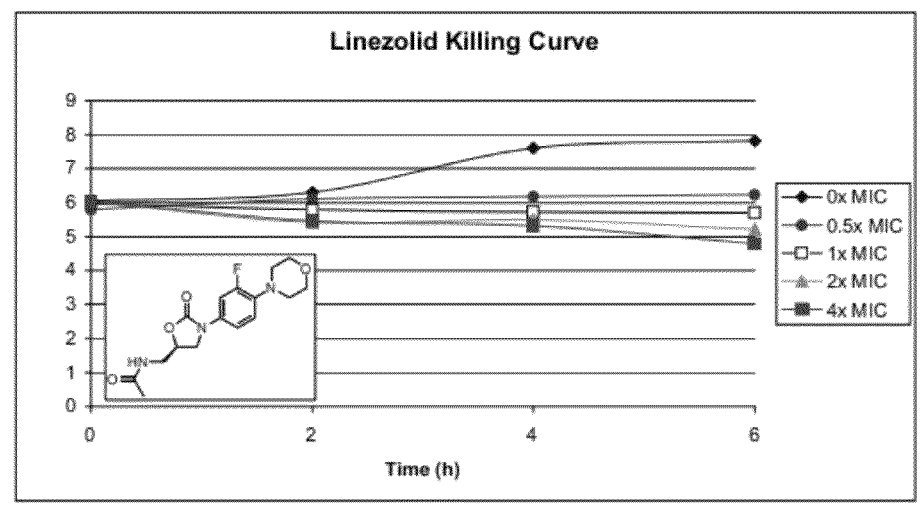

FIG. 12A-V. Inhibition dose response curves for active compounds.

FIG. 13A-D. Bacterial killing curves for compounds 4Bv, 6Ao, and 9Cf.

Figure 14:
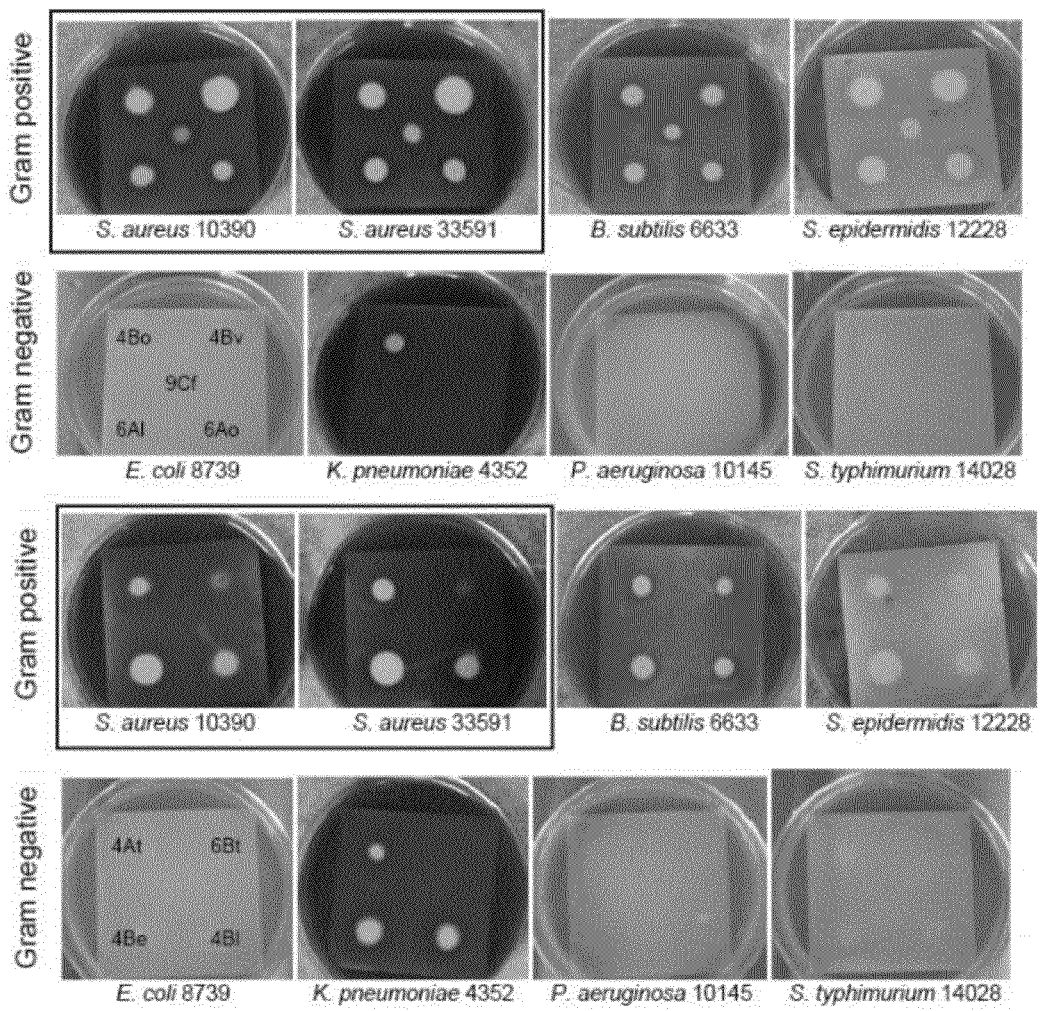
Figure 15:
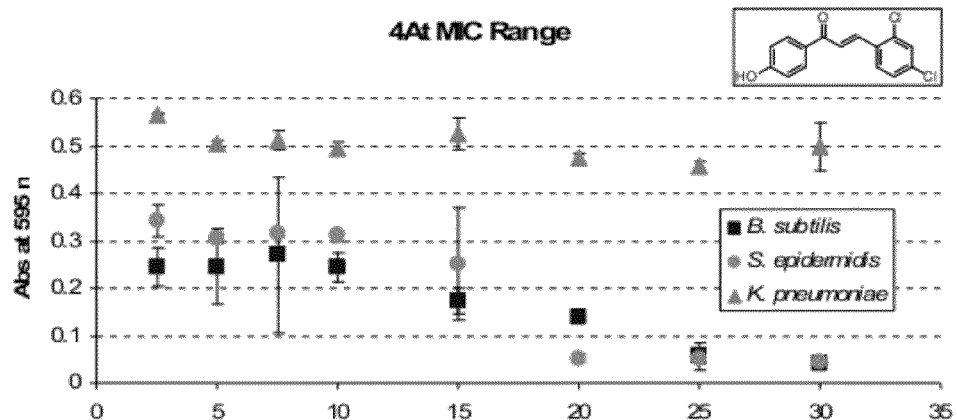
Figure 15:
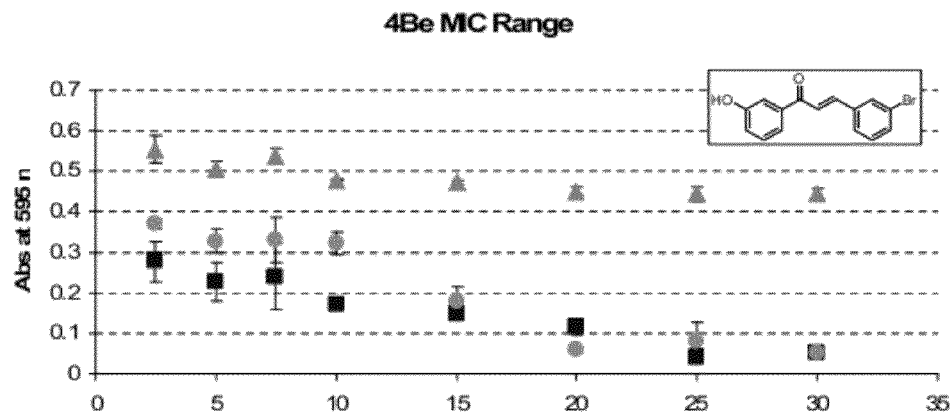
Figure 15:
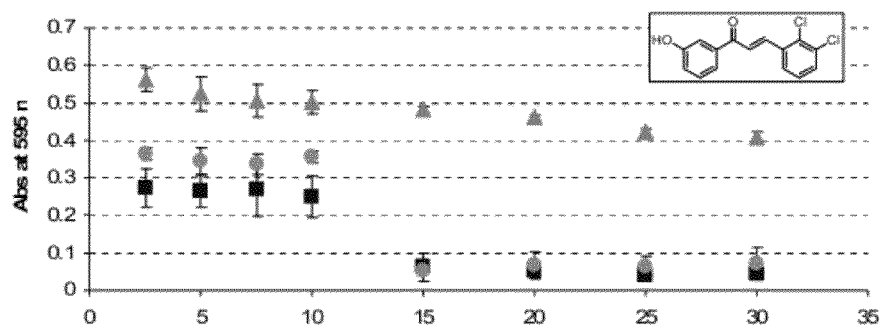
Figure 15:
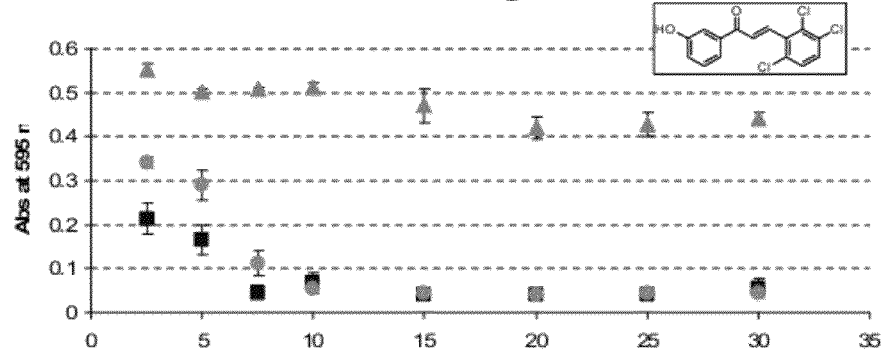
Figure 15:
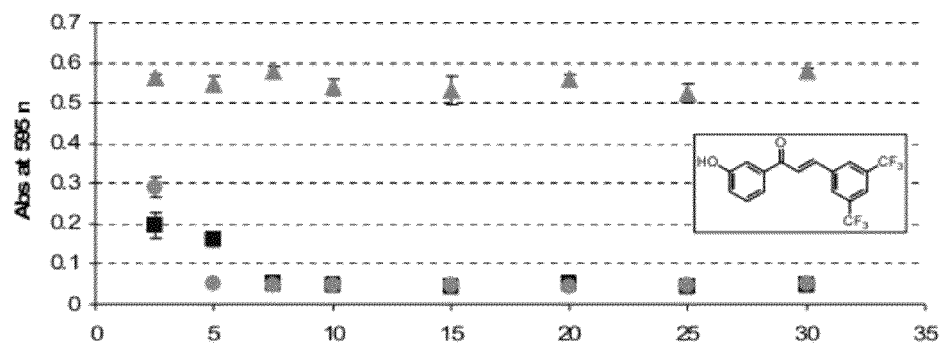
Figure 15:
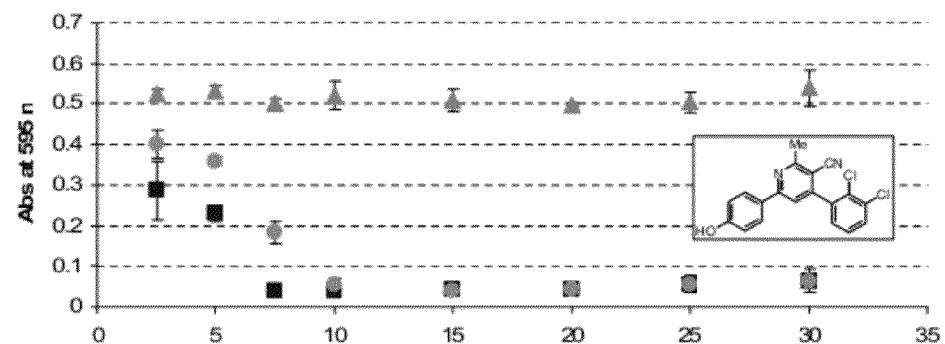
Figure 15:
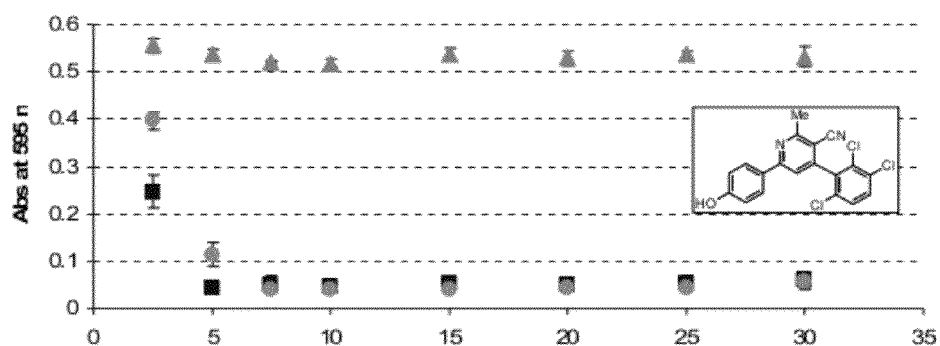
Figure 15:
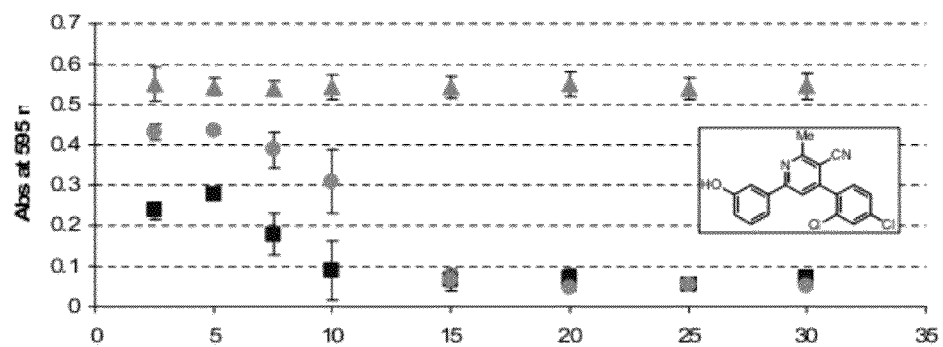
Figure 15:
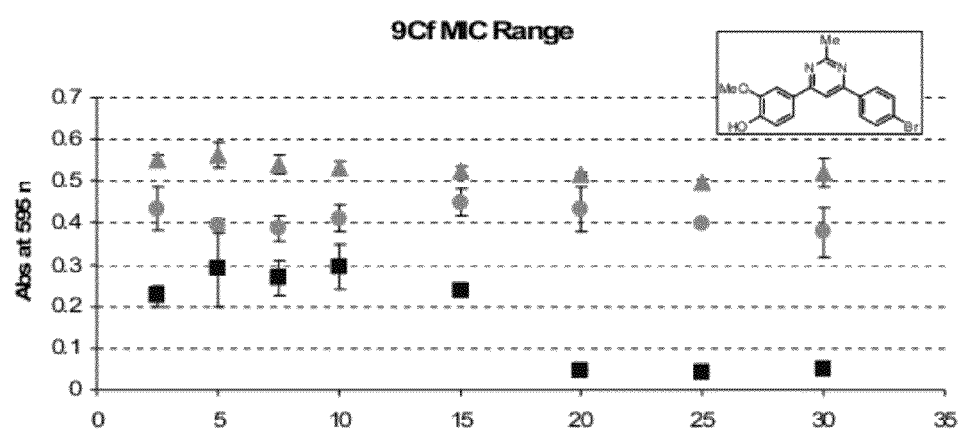
Figure 16:
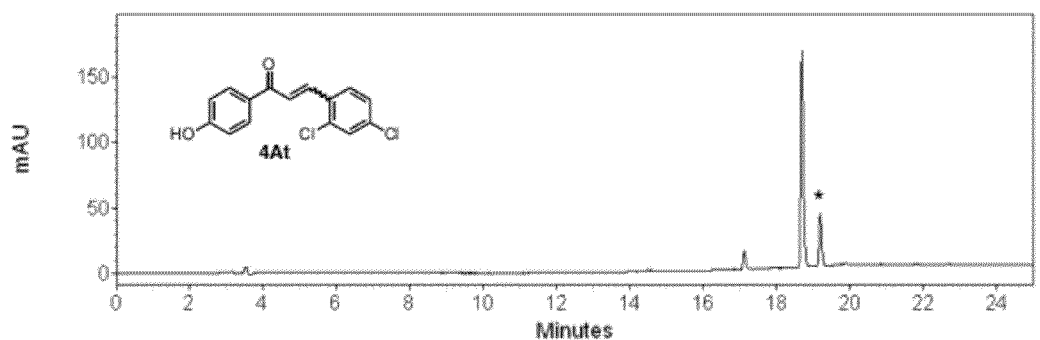
Figure 16:
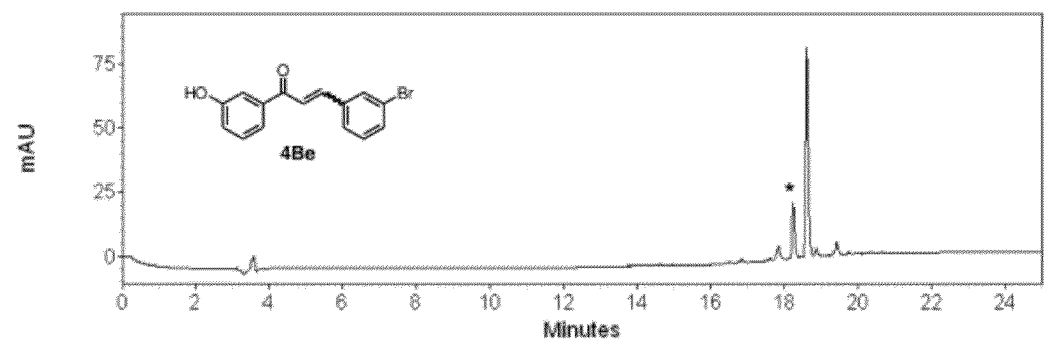
Figure 16:
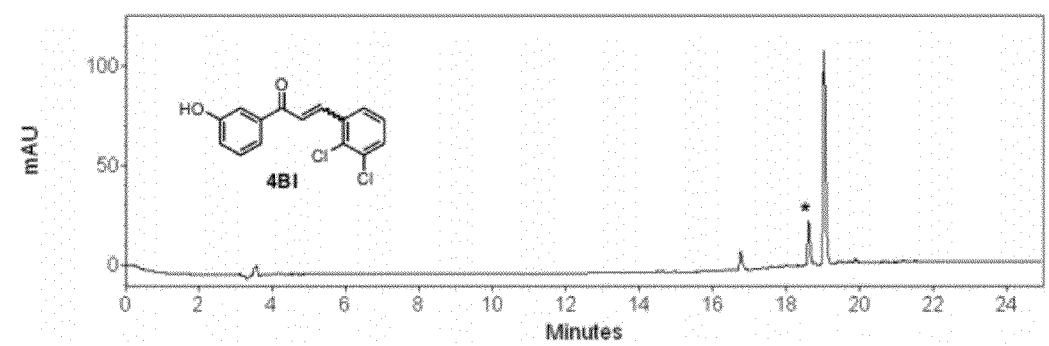
Figure 16:
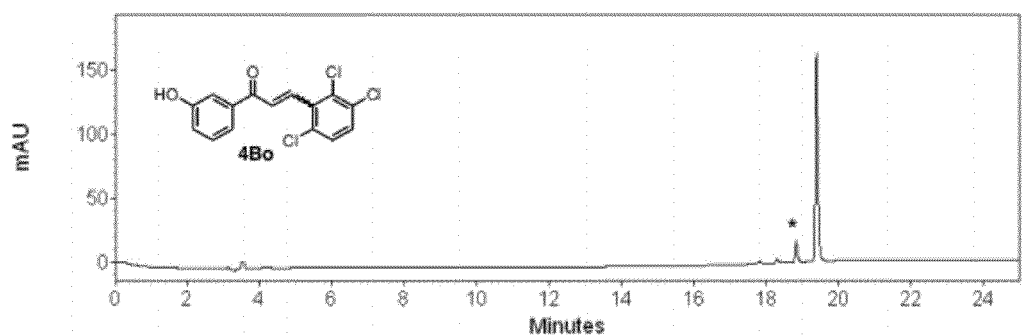
Figure 16:
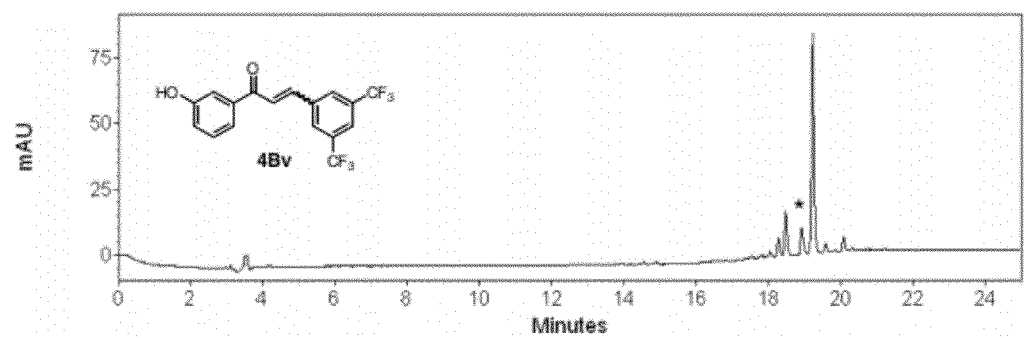
Figure 16:
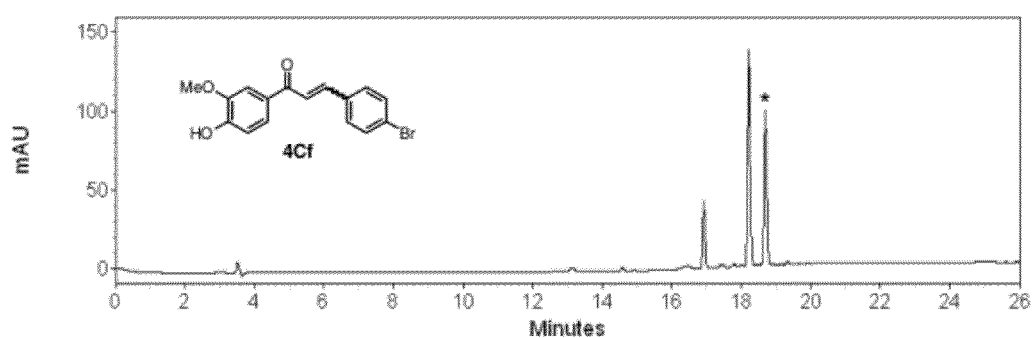
Figure 16:
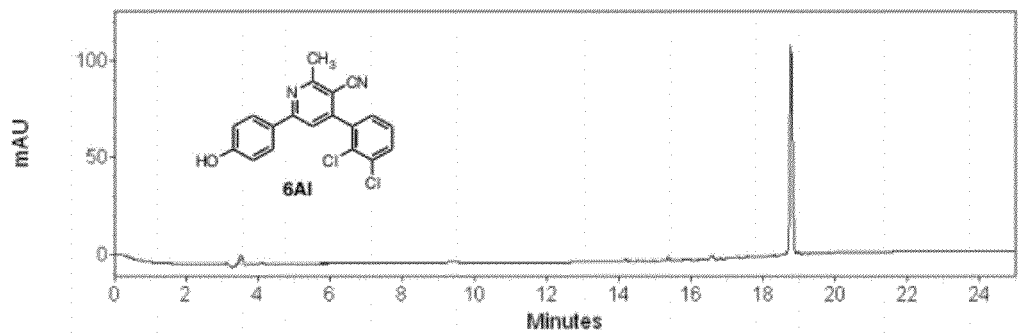
Figure 16:
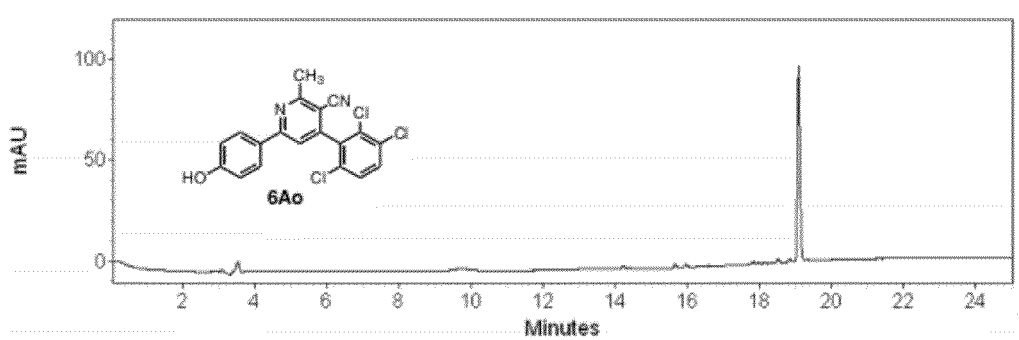
Figure 16:
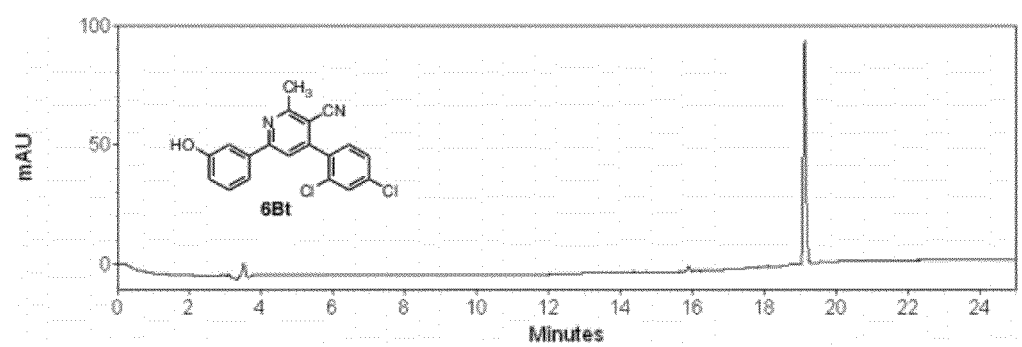
Figure 16:
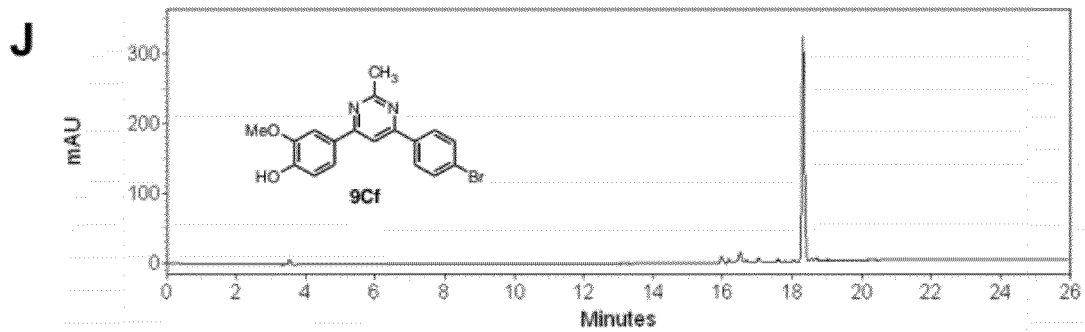

FIG. 14. Agar overlay TTC assays of active compounds against a range of Gram-positive and Gram-negative bacteria. The location of compounds on the arrays is indicated on the *E. coli* assay dishes. A: Compounds 4Bo, 4Bv, 6Al, 6Ao, and 9CF. B: 4At, 4Be, 4Bl, and 6Bt. The blue box indicates *S. aureus* control assays. Petri dish diameter=9 cm.

FIG. 15A-I. Inhibition dose response curves in *B. subtilis, S. epidermidis,* and *K. pneumoniae.*

FIG. 16A-J. HPLC traces of active compounds cleaved from macroarrays.

Figure 17:
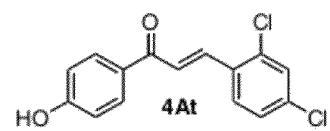
Figure 17:
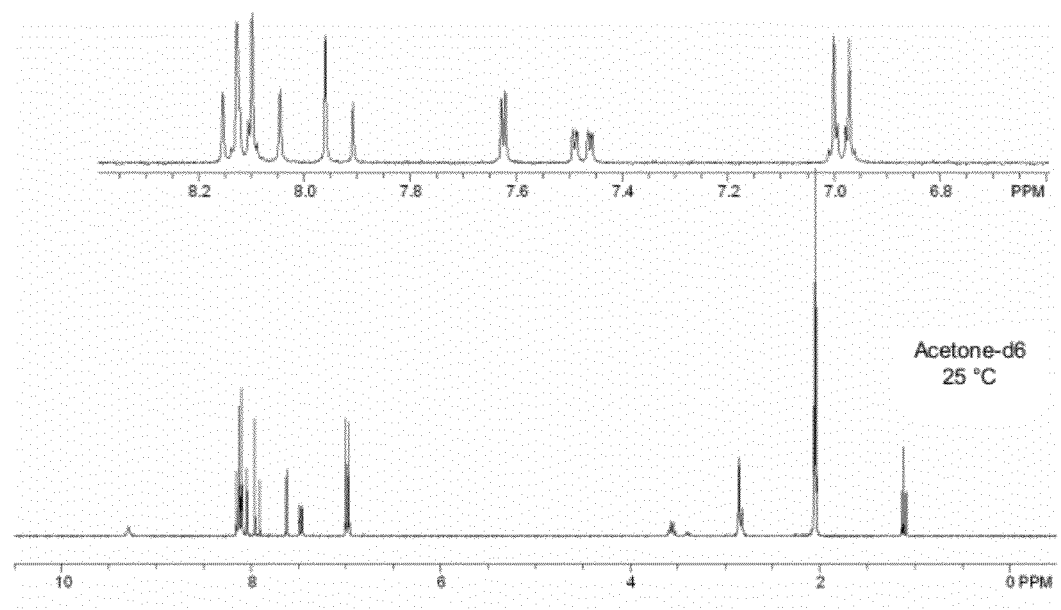
Figure 17:
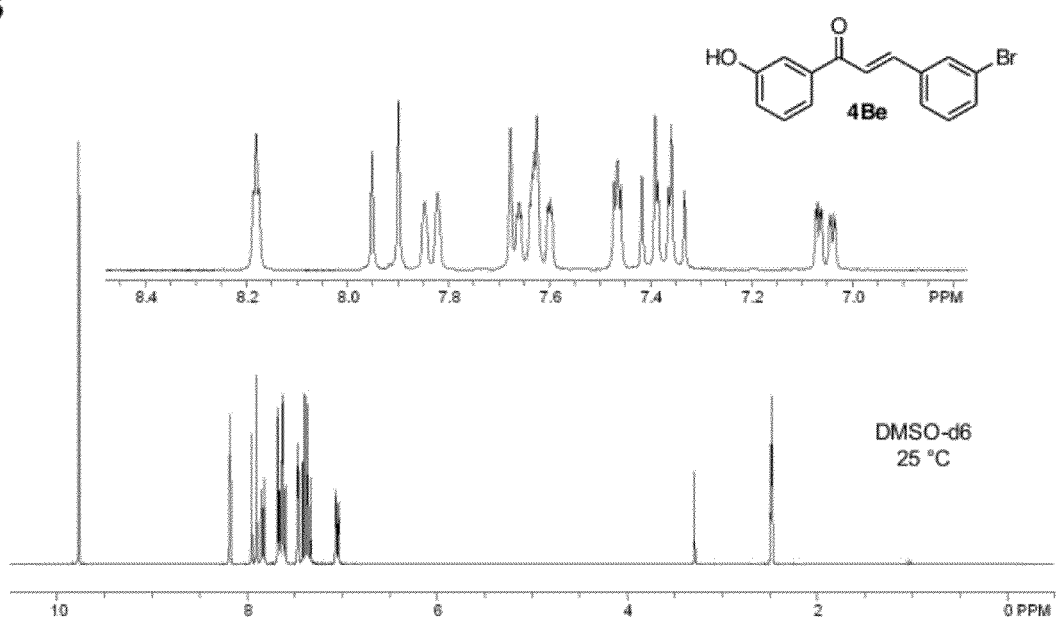
Figure 17:
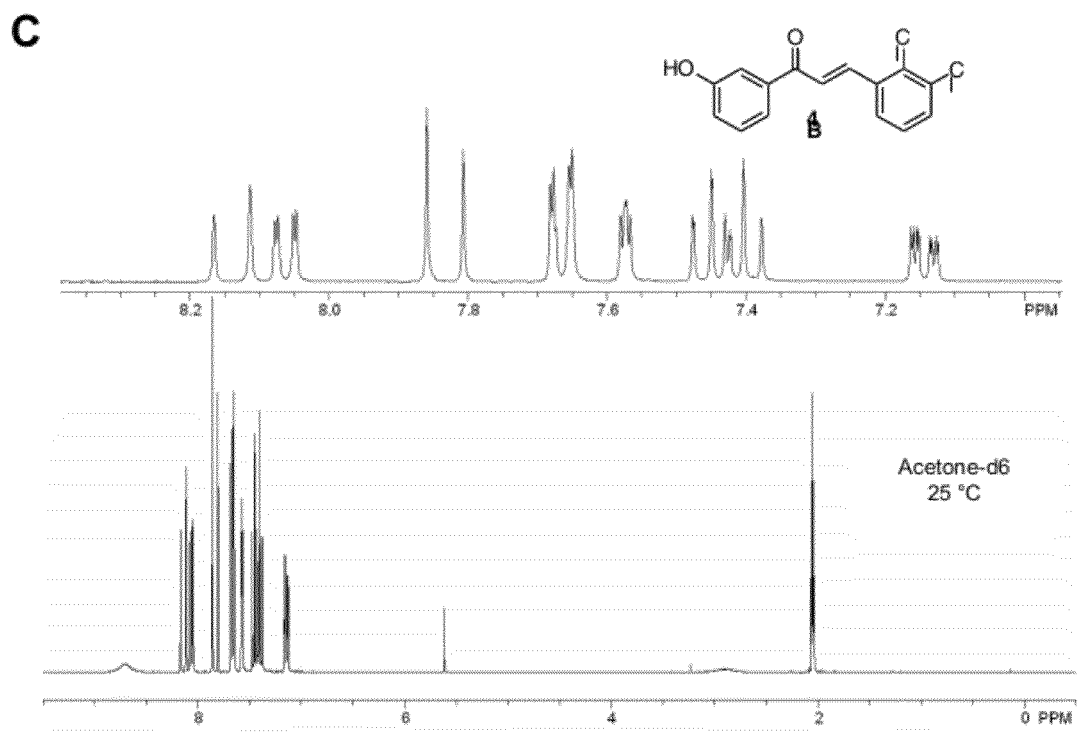
Figure 17:
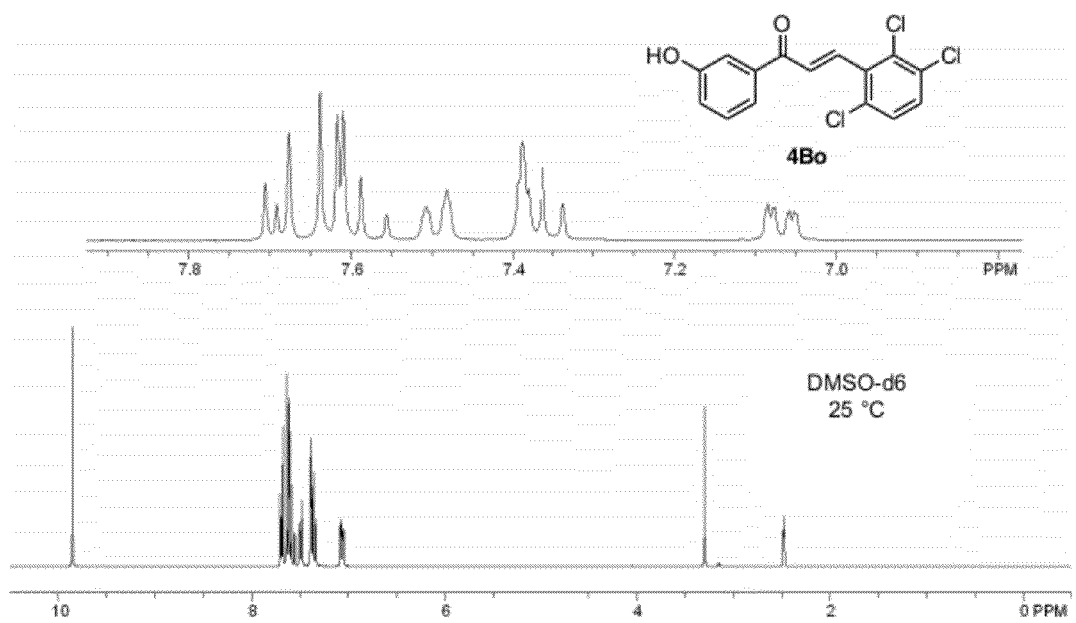
Figure 17:
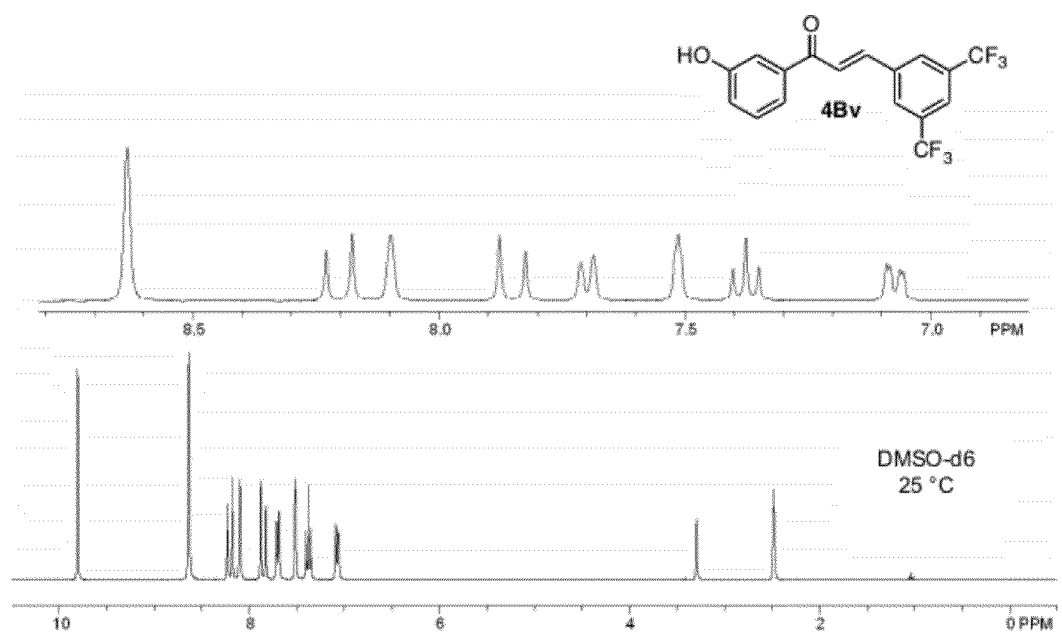
Figure 17:
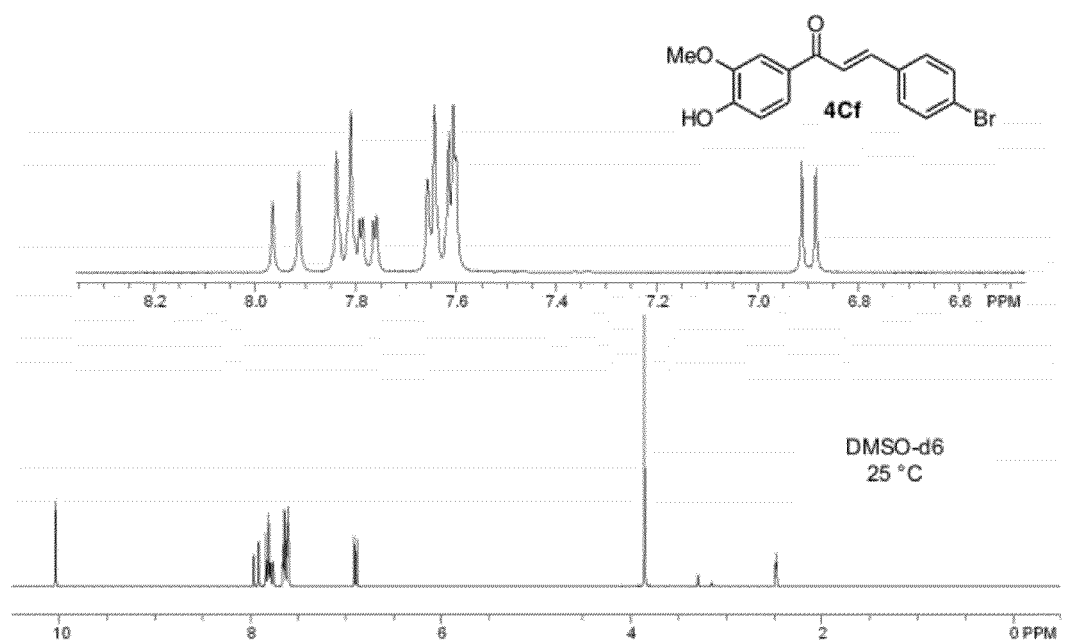
Figure 17:
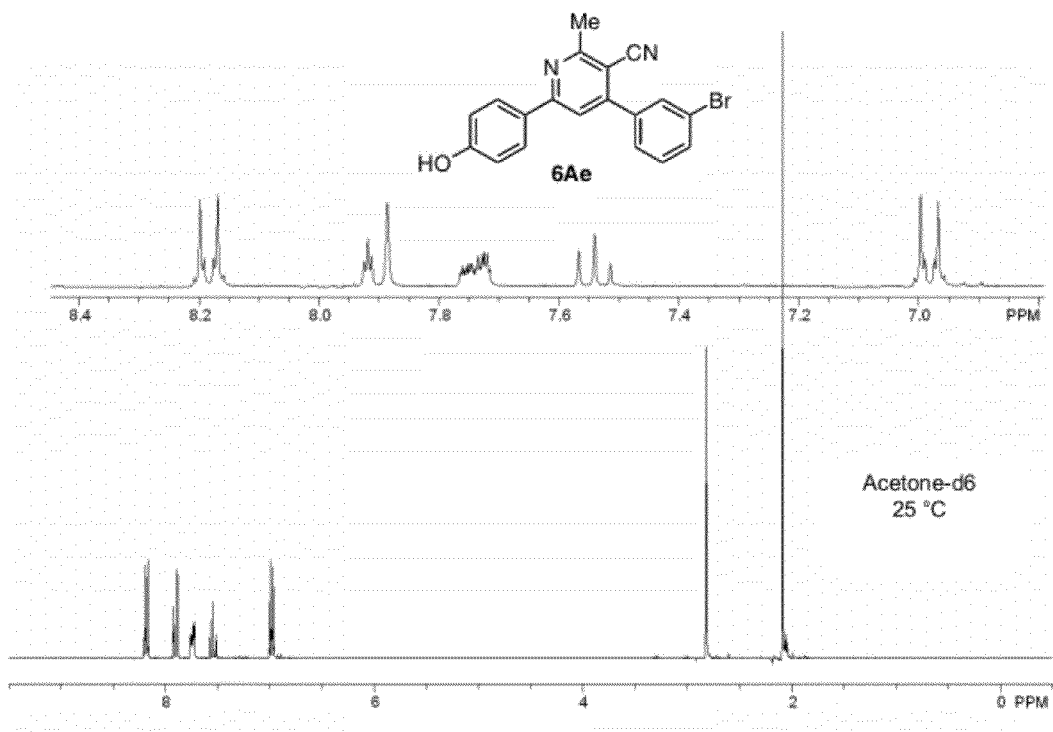
Figure 17:
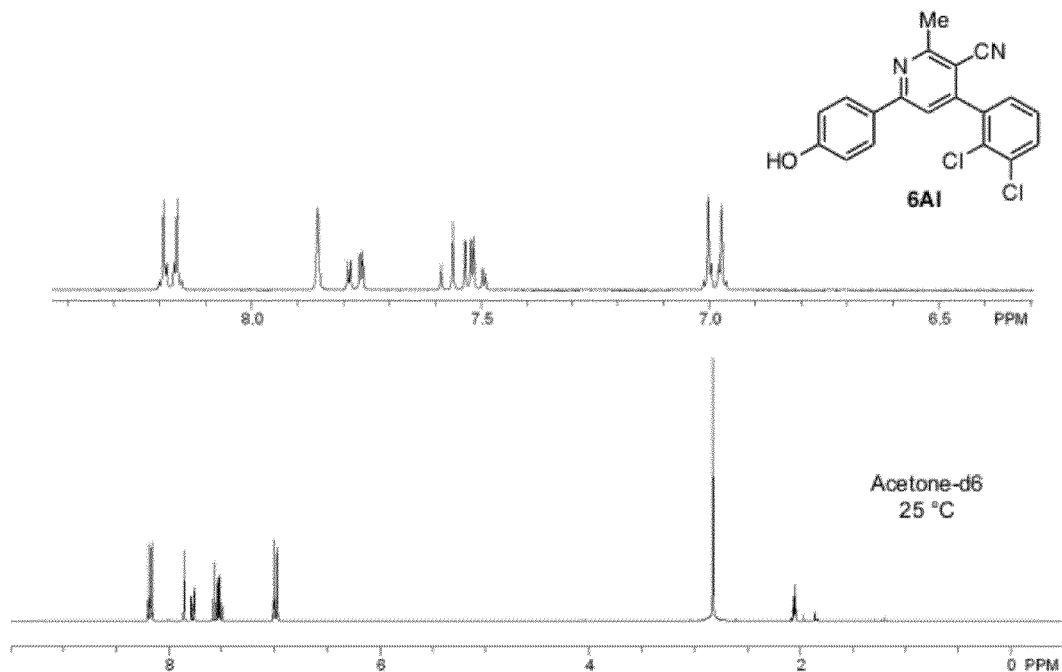
Figure 17:
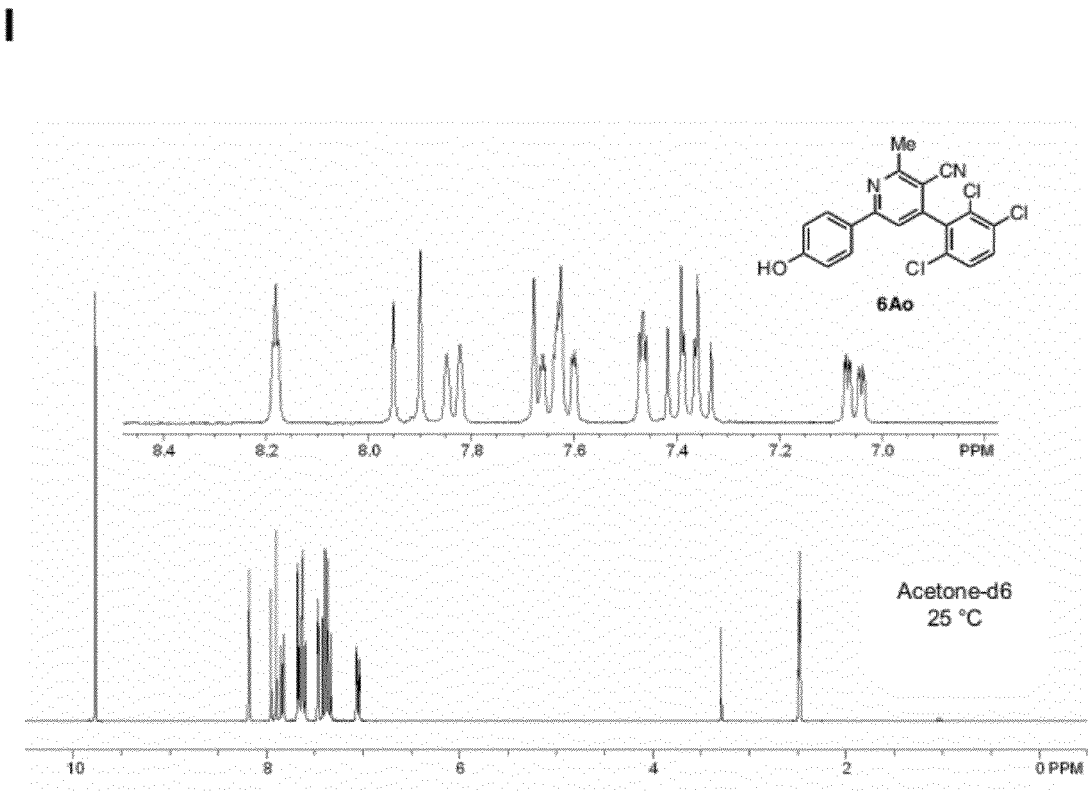
Figure 17:
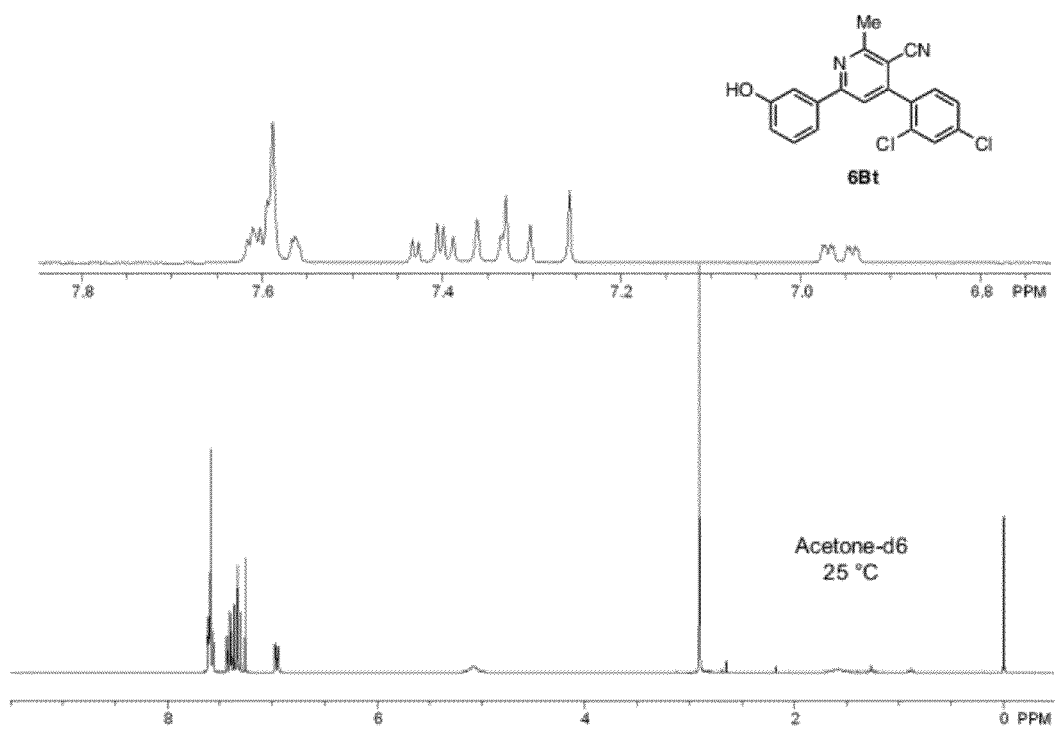
Figure 17:
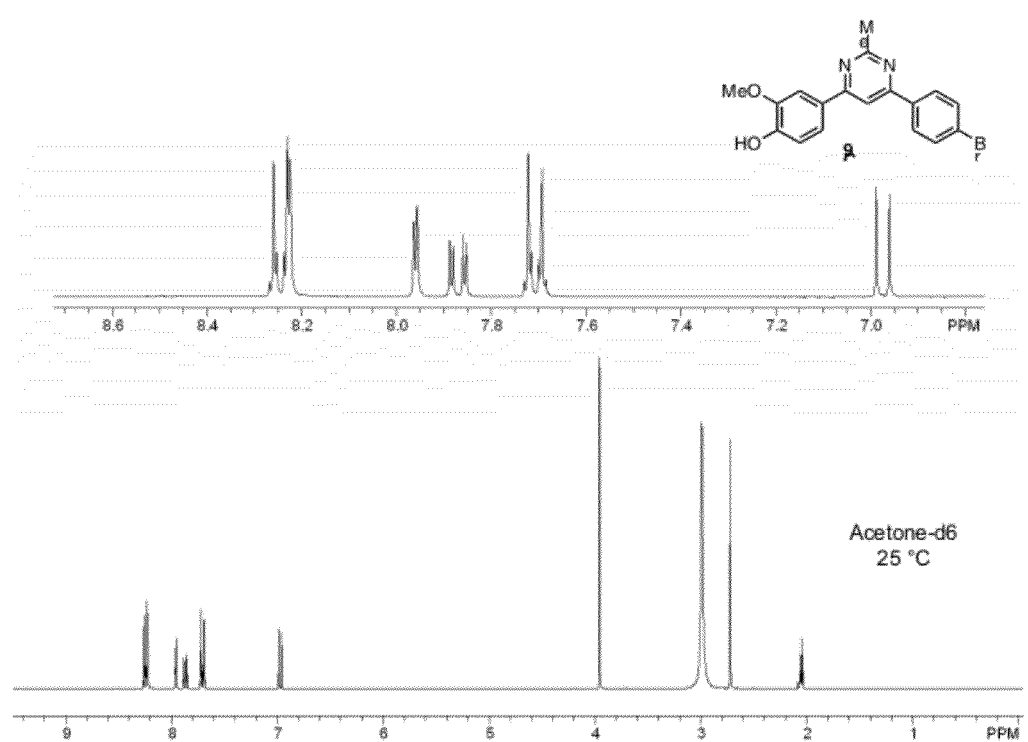
Figure 17:
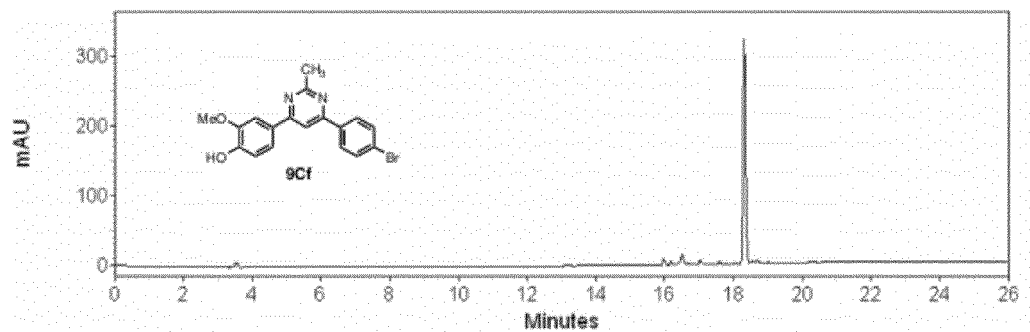
Figure 17:
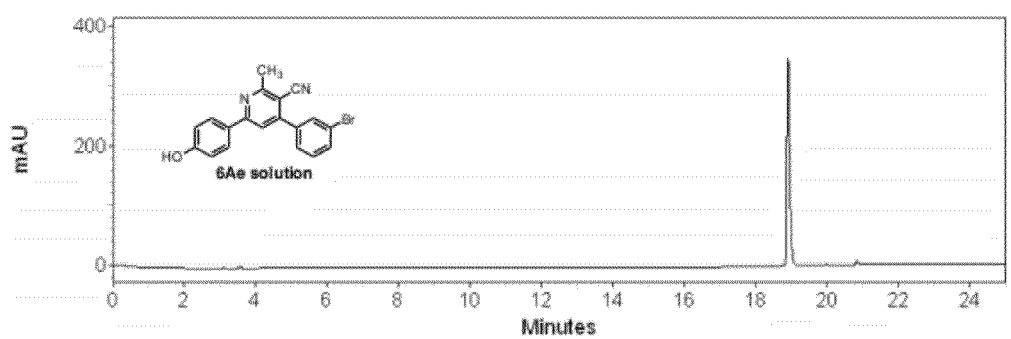
Figure 17:
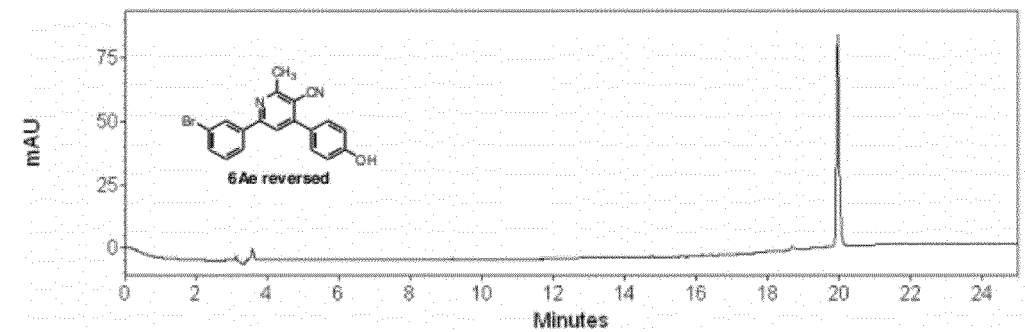

FIG. 17A-N. $^1$H NMR spectra of active compounds.

DETAILED DESCRIPTION OF THE INVENTION

Referring to the drawings, like numerals indicate like elements and the same number appearing in more than one drawing refers to the same element. Unless defined otherwise, all technical and scientific terms used herein have the broadest meanings as commonly understood by one of ordinary skill in the art to which this invention pertains. In addition, hereinafter, the following definitions apply:

As used herein, the term "array" refers to an ordered arrangement of structural elements, such as an ordered arrangement of individually addressed and spatially localized elements. Arrays useful in the present invention include arrays of containment structures and/or containment regions, such as fluid containment structures or regions, provided in a preselected, spatially organized manner. In some embodiments, for example, different containment structures and/or regions in an array are physically separated from each other and hold preselected materials, such as the reactants and/or products of chemical reactions, for example candidate compounds for screening of antimicrobial activity.

Arrays of the present invention include "microarrays" and "macroarrays" which comprise an ordered arrangement of containment structures and/or containment regions capable of providing, confining and/or holding reactants, products, solvent and/or catalysts corresponding to one or more chemical reactions, reaction conditions and/or screening conditions. In some embodiments, a portion of the reactants and/or products confined in a containment structure/region of a microarray or macroarray are immobilized, for example by spatially localized conjugation to a selected region of containment structure or region. Microarrays and macroarrays of the present invention, for example, are capable of providing an organized arrangement of containment structures and/or regions, wherein different containment structures and/or regions are useful for providing, confining and/or holding preselected combinations of reactants, products and/or candidate compounds having well defined and selected compositions, concentrations and phases. Containment structures and/or regions of microarrays and macroarrays are also useful for providing, confining and/or holding the products of chemical reactions. In some embodiments, for example, each containment structure and/or region of the microarrays and macroarrays is physically separated and contains the product of a different chemical reaction or a chemical reaction carried out under different reaction conditions.

The terms "microarray" and "macroarray" are used herein in a manner consist with the art. In some embodiments, a microarray comprises a plurality of containment structures or regions having at least one microsized (e.g., 1 to 1000s of microns) or sub-microsized (e.g., less than 1 micron) physical dimension. In some contexts, containment structures/regions of a microarray are smaller than containment structures/regions of a macroarray. In some contexts, containment structures/regions of a microarray are provided in a higher density than containment structures/regions of a macroarray. In some contexts, the number of containment structures/regions of a microarray is larger than the number of containment structures/regions of a macroarray. In specific embodiments, the invention provides macroarrays produced by SPOT synthesis are described herein and as known in the art. Macroarrays in the context of the present invention which are arrays of candidate compound for screening are prepared such that each compound member of the array (each spatially-localized compound) is present in an amount sufficient to allow its removal form the array for further analysis, for example, to measure spectral properties or to obtain confirmatory structural analysis (e.g., by mass spectroscopic analysis or NMR analysis). As will be understood by one having ordinary skill in the art may different microarray and macroarray formats are useable in the present invention including, but not limited to, standard 96, 384 or 1536 microarray configurations.

As defined herein, "contacting" means that a compound used in the present invention is provided such that is capable of making physical contact with another element, such as a microorganism, a microbial culture or a substrate. In another embodiment, the term "contacting" means that the compound used in the present invention is introduced into a subject receiving treatment, and the compound is allowed to come in contact in vivo.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxyl group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to an animal. In particular, an animal refers to a mammal, preferably a human. The subject either: (1) has a condition remediable or treatable by administration of a compound of the invention; or (2) is susceptible to a condition that is preventable by administering a compound of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The inventors have a developed an expedient approach to synthesize and screen focused parallel libraries prepared in a macroarray format for antibacterial behavior. Using this format, the inventors have discovered several new antibacterial agents, some of which are comparable to linezolid with respect to antibacterial activity. The inventors have discovered a new structure class for antibacterial compounds that displays excellent activity against *S. aureus*.

Cellulose paper is a robust, easy-to-manipulate support for the synthesis of macroarrays of chalcones and chalcone derived heterocycles (Scheme 1). Bowman, M. D.; Jacobson, M. M.; Pujanauski, B. G.; Blackwell, H. E. *Tetrahedron* 2006, 62, 4715-4727.

To further expand the utility of this platform, the synthesis of the macroarrays was coupled with high throughput screening techniques. Antimicrobial cationic peptides had been previously prepared by the SPOT-synthesis technique and subsequently screened to find inhibitors at the μg/mL range. Hilpert, K.; Volkmer-Engert, R.; Walter, T.; Hancock, R. E. W. *Nature Biotechnology* 2005, 23, 1008-1012. Encouraged by this work and previously published accounts of the antibacterial activity of chalcones, the inventors looked at the synthesis and the screening of small molecules by both on-support and solution-based assays. Nielsen, S. F.; Larsen, M.; Boesen, T.; Schønning, K.; Kromann, H. *J. Med. Chem.* 2005, 48, 2667-2677; Nielsen, S. F; Boesen, T.; Larsen, M.; Schønning, K.; Kromann, H. *Biorganic Medicinal Chemistry* 2004, 12, 3047-3054; Bowden, K. Dal Pozzo, A.; Duah, C. K. *J. Chem. Res. (S)* 1990, 12, 2801-2830.

Scheme I:

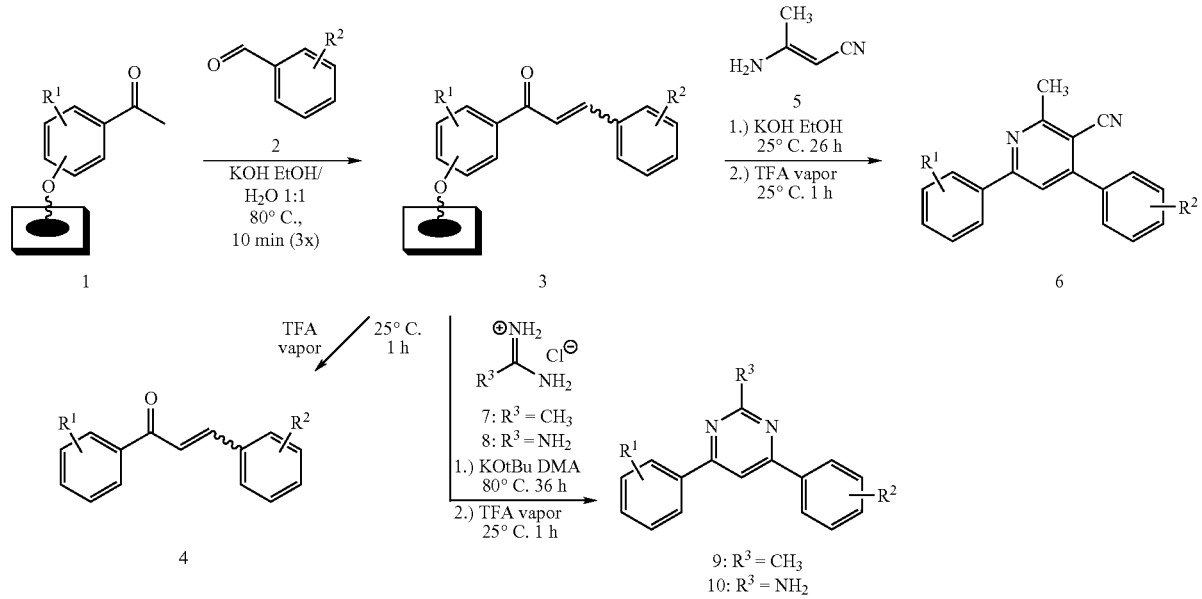

Three chalcone macroarrays using the building blocks in Table 1 were synthesized. The synthesis time for the macroarrays was only five hours. For optimization of high purity heterocycles, longer reaction times (26 h-36 h) are necessary especially with a highly loaded support (>180 nmole acetophenone/spot). Purity of compounds tends to diminish in the pyrimidines with multiply substituted benzaldehydes, due to replacement of a halide with a proton. The conditions used to generate aminopyrimidines 10 are especially conducive to this side reaction, and compounds 10Af, 10Bf, and 10Cf are readily reduced to 10Aa, 10Ba, and 10Ca respectively. Therefore, for the pyrimidine macroarrays, only benzaldehydes a-j were used.

TABLE 1

Library Building Blocks

TABLE 1-continued

Library Building Blocks

While the heterocyclic libraries were being synthesized, the chalcone macroarrays were analyzed using various direct assay techniques such as the Kirby-Bauer disk diffusion assay (FIG. 2E). Bauer, A. W.; Kirby, W. M. M.; Sherris, J. C.; Turck, M. *Technical Bulletin of the Registry of Medical Technologists* 1966, 36, 49-52. For this assay, the macroarray members are punched out from the membrane, cleaved from the support with TFA vapor, neutralized with ammonia vapor, and then placed on an agar bed inoculated with *S. aureus*. After incubating overnight, different diameters of zones of inhibition are measured as a factor of potency as well as solubility in the medium. Ammonia vapor neutralization was key in the disk diffusion assay, otherwise residual TFA vapor created a false positive signature. However, in this method, macroarrays have to be made in triplicate one for a replicate and one for compound characterization.

To take advantage of the spatially-addressed nature of the macroarray format, an agar overlay assay was employed that utilizes TTC (triphenyl tetrazolium chloride) as a visualization agent (FIG. 2F). Silen, J. L.; Lu, A. T.; Solas, D. W.; Gore, M. A.; Maclean, D.; Shah, N. H.; Coffin, J. M.; Bhinderwala, N. S.; Wang, Y.; Tsutsui, K. T.; Look, G. C.; Campbell, D. A.; Hale, R. L.; Navre, M.; DeLuca-Flaherty, C. R. *Antimicrob. Agents Chemother.* 1998, 1447-1453. Unfortunately, during macroarray synthesis the planarity of the support is not fully maintained, and small wrinkles develop in this particular assay. This problem was solved by using an adaptation of the common Western Blot technique to copy the macroarray members from the support to fresh wrinkle-free sheets while maintaining the spatially-addressed nature. This transfer can be completed in 90 seconds and four copies can be made at a time, however to date, it is applicable only for smaller macroarrays (6 cm×6 cm, 16 spots). The full macroarray was easily divided into these dimensions. The copies allowed for replicates to be made, and the original, which cannot be used in the assay, is used to validate the compounds by LCMS. As an added feature, the sensitivity of the assay was tuned by simply changing the amount of agar applied to the array. The copies generated in the assay can also be easily used to screened against multiple organisms.

The two evaluated assays gave rapid, but qualitative results. For more quantitative results, a solution-phase microdilution absorbance assay was developed that could give preliminary MIC information. Most importantly, the identity and purity of the screened library member can be obtained directly through LCMS analysis as opposed to a replicate spot (disk diffusion assay) or a compound that had undergone a mild form of paper chromatography (agar overlay assay).

Spots from a new 69 member chalcone macroarray as well as the three heterocyclic macroarrays prepared earlier were punched out, cleaved, and eluted with acetonitrile. The resulting solutions were concentrated to a residue that was taken up in DMSO to form 2 mM stock solutions.

Any excess stock solution not used in the assays can be concentrated again and analyzed by LCMS. For quality control, a random sampling (70%) of the library members of each macroarray was analyzed by LCMS. This resulted in moderate to high purities of the compounds tested (96% of the chalcones, 85% of the cyanopyridines, and 81% of the pyrimidines had purities greater than 70%).

From the stock solutions, microdilution assays in a 96 well plate starting at 50 µM were performed in quadruplicate. Each well contained 5 µL of the stock solution as well as 195 µL of a *S. aureus* culture. The turbidity of each well was measured after incubating 12 hours using a standard plate reader. Active compounds can be further diluted and the assay repeated.

In the initial assay at 50 µM, 17 chalcones, 12 cyanopyridines, and two pyrimidines were found to inhibit *S. aureus*. The initial stock solutions were diluted two and four fold and rescreened. Five chalcones and six cyanopyridines were active at the 25 µM level, and two chalcones (4Bo and 4Bv) and two cyanopyridines (6Ao and 6Bt) demonstrated complete inhibition at the 12.5 µM level. These compounds as well as a few with different levels of inhibition as determined by the preliminary screens were synthesized using standard techniques. These standard compounds were fully characterized and their activities were evaluated and compared to the activities estimated from the macroarray (Table 2). Excellent agreement from the macroarray microdilution, agar overlay, and the synthesized standards were seen in all but one case. In that case, the lower purity (72%) from the macroarray led to the underestimation of the activity of 4Bv.

TABLE 2

Antibacterial activity of compounds against *S. aureus*.

| entry | compound | purity[a] (%) | estimated MIC range[b] (µM) | observed MIC[c] (µM) |
|---|---|---|---|---|
| 1 | 4Cf | 86 | >50 | >250 |
| 2 | 4Be | 88 | 25-50 | 24 ± 2.0 |
| 3 | 4At | 94 | 25-50 | 18.8 ± 1.2 |
| 4 | 4Bl | 93 | 12.5-25 | 13.8 ± 1.2 |
| 5 | 4Bo | 91 | 6.25-12.5 | 6.5 ± 0.5 |
| 6 | 4Bv | 72 | 6.25-12.5 | 3.3 ± 0.3 |
| 7 | 6Al | 99 | 12.5-25 | 8.7 ± 1.3 |
| 8 | 6Ao | 99 | 6.25-12.5 | 6.0 ± 0.5 |
| 9 | 6Bt | 99 | 6.25-12.5 | 10.0 ± 1.0 |
| 10 | Ciprofloxacin | — | — | 0.75 ± 0.12 |
| 11 | Linezolid | — | — | 6.0 ± 0.5 |

[a] Determined after cleavage from the macroarray. Purity determined by integration of the HPLC trace at 254 nm.
[b] Estimated MIC range from the serial dilution of stock solutions obtained by SPOT-synthesis.
[c] Observed MIC determined using an authentic sample synthesized according to standard techniques; as described below.

The inventors have developed a versatile platform that can be used to synthesize small molecules and screen them in preliminary biological assays (both on-support and in solution). The real strength of this methodology lies not only in the ease of synthesis and screening, but also in the ability to identify a compound with a degree of certainty without the need for labor-intensive and time-consuming deconvolution steps. Chalcone macroarrays can be synthesized and screened in 24 hours. For chalcone-derived heterocycles, only an additional 26 to 36 hours are needed. In the case of the solution-phase assay and the agar overlay method, library member purity can be determined before or after screening allowing for confidence of the assay quality. Using these simple assays, a new potent inhibitor as well as a new antimicrobial structure class have been discovered.

EXAMPLE 1

Rapid Identification of Antibacterial Agents Effective Against *Staphylococcus aureus* Using Small Molecule Macroarrays 1.a. Summary There is an urgent, global need for the development of new antibacterial agents. We have applied the small molecule macroarray approach to the synthesis and screening of antibacterial compounds active against the Gram-positive pathogen *Staphylococcus aureus*. Several macroarrays of 1,3-diphenyl-2-propen-1-ones (chalcones), cyanopyridines, and pyrimidines were synthesized on a planar cellulose support system on the order of days. This support system was found to be highly compatible with antibacterial assay formats, including disk diffusion and agar overlay visualization methods. Further, sufficient compound was isolated from each spot of the macroarray for both compound characterization and minimum inhibitory concentration (MIC) estimation. Analysis of the small molecule macroarrays in these assays uncovered a set of antibacterial agents with novel structures and in vitro MIC values against methicillin-resistant *S. aureus* comparable to certain antibacterial drugs in use today.

1.b. Introduction

The continued emergence of bacterial strains resistant to antibacterial agents is a serious threat to human lives [1]. Each year, nearly two million patients in the US acquire bacterial infections in hospitals, and 10% of these patients die as a result. Over 70% of these infections involve bacteria that are resistant to at least one antibacterial drug [2]. The Gram-positive pathogen *Staphylococcus aureus* is possibly most notorious as a cause of these infections due to the rapid appearance of multi-drug resistant strains, including strains impervious to methicillin and the last-line therapy, vancomycin [3]. For example, only one year after FDA approval, *S. aureus* resistance emerged against oxazolidinones (e.g., linezolid), the newest class of synthetic antibacterials [1, 4]. Such a rapid growth of resistance underscores an urgent need for the continued development of new antibacterial agents. Here, we report the discovery of a suite of new compounds that display potent antibacterial activities against methicillin-resistant *S. aureus*. In addition, we have identified a new antibacterial structure class, 2-methyl-3-cyanopyridines. These compounds were uncovered using the small molecule macroarray approach and serve to demonstrate the utility of this technique for antibacterial research.

The continued need for new and structurally varied antibacterial agents strongly supports a combinatorial approach for their synthesis [1, 4], and this is evidenced by considerable research efforts in this area [5-7]. Our laboratory has been engaged in the development of the small molecule macroarray as a tool for the rapid, parallel synthesis of libraries of organic molecules (ca. 50-200 compounds) [8]. This method involves the spatially addressed, solid-phase synthesis of discrete small molecules (mol. wt≦500 g/mol) on planar cellulose supports (spot size=0.3 cm$^2$). Macroarrays provide several advantages relative to other combinatorial synthesis methods: the arrays are inexpensive to prepare, straightforward to manipulate, and yield sufficient compound per spot for numerous assays to be performed post-synthesis (100-200 nmol) [9-12]. We reasoned that these benefits significantly streamline the antibacterial discovery process.

1.c. Results and Discussion

Figure 1:
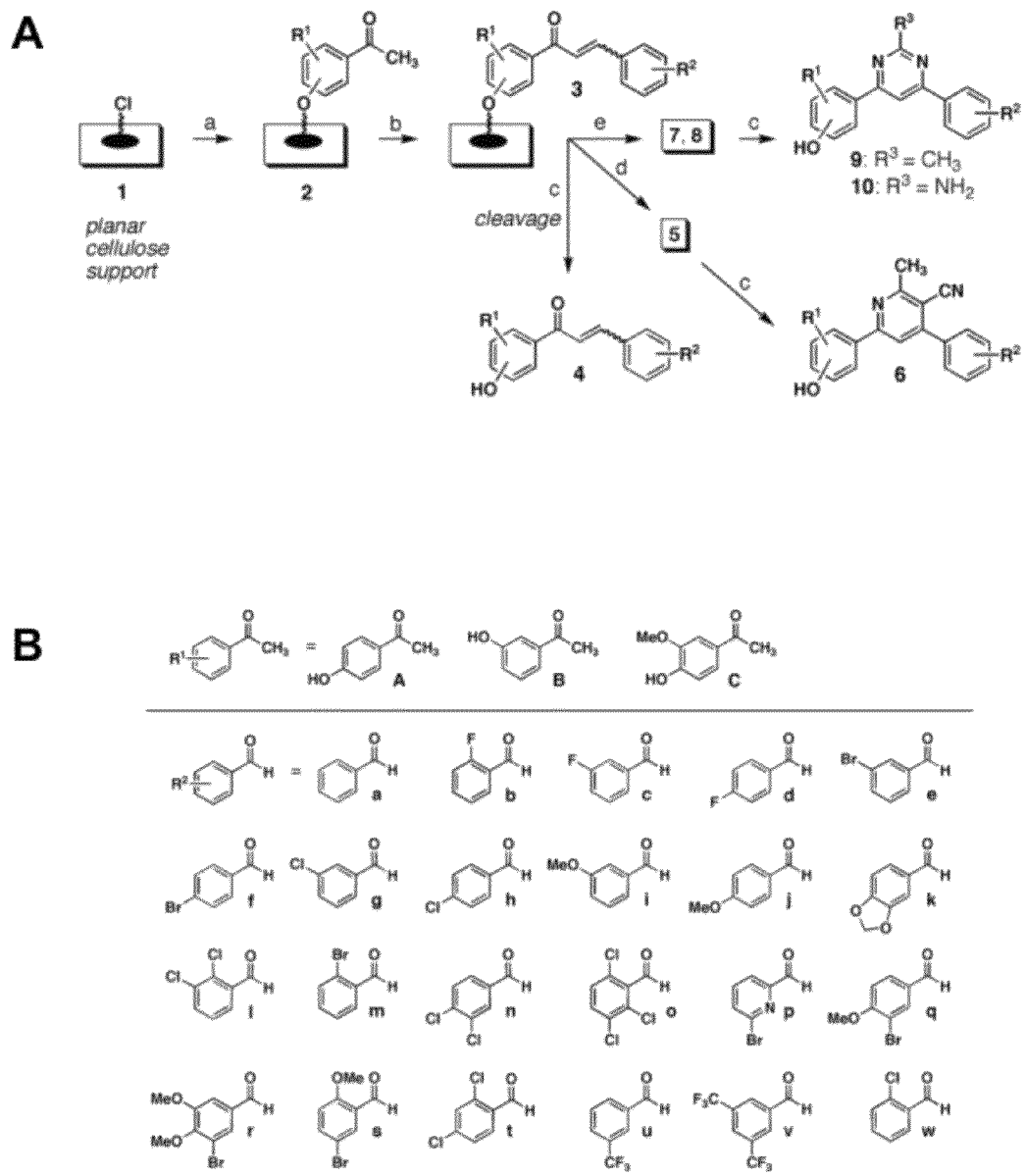
FIG. 1. Small Molecule Macroarray construction. (A) Macroarray synthesis. Reaction conditions: (a) hydroxyacetophenones A-C, KOtBu, DMF, 80° C., 10 min (3×). (b) benzaldehydes a-w, KOH, EtOH/H$_2$O (1:1), 80° C., 10 min (3×). (c) cleavage: TFA, then neutralization with NH$_3$, rt, 2 h. (d) 3-aminocrotononitrile, KOH, EtOH, rt, 26 h. (e) acetamidine- or guanidine-HCl, KOtBu, DMA, 80° C., 36 h. All reactions performed under air.

Three complementary design criteria guided our synthesis of macroarrays for antibacterial screening. First, we sought to examine molecular scaffolds known to exhibit antibacterial activity against *S. aureus*, as macroarrays of such compounds would allow us to validate on- and off-support antibacterial array screening formats. Second, we also desired to study small molecule classes that remain unexplored as antibacterials. Third, the synthetic routes needed to be compatible with our planar solid support system [8]. We selected three compound classes that met these design criteria: 1,3-diphenyl-2-propen-1-ones (chalcones), pyrimidines, and 2-methyl-3-cyanopyridines. Certain lipophilic chalcones have been reported to exhibit antibacterial activities against *S. aureus* [13, 14], while the latter two heterocycle classes have been largely unexplored as antibacterial agents [15, 16]. We built upon our previous macroarray synthesis methods and developed efficient synthetic routes to each structure class on planar supports (FIG. 1A) [10, 11]. These routes were applied to the construction of 30- to 69-member macroarrays incorporating a broad range of functionality; the building blocks utilized in macroarray synthesis are shown in FIG. 1B. Briefly, three hydroxyacetophenones (A-C) were coupled in a spatially addressed manner to planar cellulose derivatized with an acid cleavable Wang linker (1) [8]. Claisen-Schmidt condensation of support 2 with various benzaldehydes (a-w) afforded chalcone macroarrays 3. Further condensation of these arrays (3) with 3-aminocrotononitrile, acetamidine, or guanidine gave 2-methyl-3-cyanopyridine (5), methylpyrimidine (7), and aminopyrimidine (8) macroarrays, respectively [17].

LC-MS analyses of a subset of the total compounds (70%) cleaved from the macroarrays indicated good to excellent purities (ca. 70-98%). Certain chalcone products (4) were isolated as mixtures of cis and trans isomers, with the latter isomer predominating (ca. ≧4:1). As the double bonds in certain chalcones are labile to photoisomerization [13, 14], we reasoned that separating these isomers prior to primary screening would be unproductive. For the small number of library members with lower purities, the major by-product was starting material and therefore a known compound. Consequently, we deemed the macroarray purity levels acceptable to proceed to antibacterial assays. The total time required for the synthesis of all four macroarray classes was less than two days, highlighting the efficiency of this synthetic approach for library construction [8].

We first evaluated test chalcone macroarrays (3) in antibacterial assays against *S. aureus*. Because the macroarrays were prepared on cellulose filter paper, we had convenient access to the compounds in disk form for standard disk diffusion assays. Compound spots were punched out of the macroarrays, subjected to vapor phase cleavage with acid (TFA), and neutralized ($NH_3$) to afford disks containing ca. 30 µg of adsorbed compound [8]. These disks were manually placed on lawns of *S. aureus*, and zones of inhibition were measured after an 18 h incubation period. Using this assay, we identified several chalcones (4) with antibacterial activities against *S. aureus*, including two compounds that were comparable on a per microgram basis to vancomycin and had novel structures (4Bv and 4Bl, FIGS. 2A and 2B) [13, 14]. However, this antibacterial assay format had drawbacks: (1) the entire sample of compound was consumed during the assay, and thus replicate arrays needed to be synthesized to confirm activity, and (2) manipulating large numbers of compound disks was relatively labor intensive.

We found that an agar overlay assay was more effective for the antibacterial screening of macroarrays relative to disk diffusion. This assay format also took advantage of the spatially addressed nature of the arrays (FIG. 2C). Intact arrays were cleaved, overlaid with agar inoculated with *S. aureus*, and incubated for an 18 h period; treatment thereafter with the redox indicator triphenyl tetrazolium chloride (TTC) allowed clear and reproducible visualization of areas of live (red) or dead (white) cells [18]. Antibacterial compounds generated an obvious white spot, with sizes reflecting their relative activities and solubilities. To reduce compound consumption in this assay, we discovered that macroarray members could be transferred onto multiple sheets by simply sandwiching cleaved arrays between a solvent-saturated surface and dry cellulose sheets (to generate up to eight copies simultaneously). The copies were then subjected to replicate TTC assays.

Using this convenient transfer and overlay procedure, we identified antibacterial chalcones and cyanopyridines from test macroarrays 3 and 5 with a range of inhibitory activities (e.g., 4Be and 4Bo, FIG. 2C). This straightforward assay also revealed preliminary SAR, with chalcones (4) and cyanopyridines (6) bearing multiple halogens at the —$R^2$ position exhibiting the highest activities. Pyrimidines 9 and 10 displayed only low to moderate activities in this assay (see FIG. 6). In the course of these studies, we also found that the TTC assay is compatible with small molecule macroarrays in formats other than spots, as exemplified in FIG. 2D. We anticipate agar overlay assays should find broad application in macroarray-based research due to their ease of use and versatility.

To acquire more quantitative antibacterial activity data about our compounds and verify our on-support assay results, we performed solution-phase absorbance assays that provided estimates of the minimum inhibitory concentration (MIC) of each macroarray member against *S. aureus*. Stock solutions (ca. 2 mM) were generated by cleaving and eluting 198 individual compounds from chalcone (3) and heterocyclic macroarrays (5, 7, and 8). The stock solutions provided sufficient compound for estimated MIC determination over a range of concentrations (50-12.5 µM) in quadruplicate. The good overall purities of the crude macroarray compounds allowed for reasonable estimations of MICs.

The preliminary MIC assays revealed two chalcones (4Bo and 4Bv) and two cyanopyridines (6Ao and 6Bt) with estimated MICs of less than 12.5 µM against *S. aureus* (Table 1). We resynthesized these active compounds in solution, along with several other compounds that exhibited varied levels of inhibition in these three assays for comparison, and determined their actual MIC values. (Note: all chalcones 4 were isolated and screened as the single trans isomer.) The absolute and relative MIC values compared favorably with our primary screening data (Table 3). Furthermore, this set of compounds exhibited analogous activities against a methicillin-resistant clinical strain of *S. aureus*. Notably, four compounds (4Bo, 4Bv, 6Al, and 6Ao) were identified that displayed MIC values against methicillin-resistant *S. aureus* comparable to that of the current drug linezolid (entry 11), with chalcone 4Bv closer in activity to ciprofloxacin (entry 12). Evaluation of these compounds in time-dependent bacterial killing assays indicated different modes of activity for the two structure classes, i.e., chalcone 4Bv was found to be bacteriostatic against *S. aureus* at its MIC, while cyanopyridine 6Ao was bactericidal. Compounds with either mode of action are valuable as antibacterial strategies [4]. To our knowledge, chalcones 4Bo and 4Bv were previously unknown to have activity against *S. aureus*. Moreover, the discovery of 6Al and 6Ao is significant, as 2-methyl-3-cyanopyridines represent, to our knowledge, a new antibacterial structure class.

To broaden the potential utility of these lead compounds as antibacterial agents, we examined their activities against a panel of bacterial strains. We selected the following six pathogens due to their clinical relevance: (1) Gram-negative—*Pseudomonas aeruginosa, Escherichia coli, Klebsiella pneumoniae*, and *Salmonella typhimurium*, and (2) Gram-positive—*Staphylococcus epidermidis* and *Bacillus subtilis*. Previous reports have indicated that chalcones are most effective against Gram-positive bacteria [19], while the selectivities of 2-methyl-3-cyanopyridines and pyrimidines are for the most part unknown [15, 16]. To rapidly access the compounds' activities, we performed agar overlay TTC assays against the panel of six strains. Briefly, we prepared arrays of our nine active compounds in Table 3 by spotting 30 nanomole aliquots of purified compound onto individual filter paper sections, and subjected the arrays to TTC overlay assays against each strain as described above. These experiments revealed that the compounds were significantly more active against the Gram-positive strains relative to Gram-negative, with only *K. pneumoniae* being weakly susceptible to chalcones 4At, 4Be, 4Bl, and 4Bo (see FIG. 7).

We determined MIC values for each active compound against *S. epidermidis, B. subtilis*, and *K. pneumoniae* (Table 4), and the MICs for the former two Gram-positive strains closely matched those determined for *S. aureus* (Table 3). Indeed, cyanopyridines 6Al and 6Ao and methylpyrimidine 9Cf displayed increased activities against *B. subtilis* versus *S. aureus* (entries 6, 7, and 9, respectively; Table 4). In accordance with the agar overlay assays, the MIC values against *K. pneumoniae* were considerably higher, however. Together, these data indicate that the lead compounds identified in this study represent both a potent and selective family of antibacterials.

In summary, this example demonstrates the utility of the small molecule macroarray as a new tool for the discovery of antibacterial agents. Three complementary assay protocols were developed that underscore the versatility of the macroarray platform for antibacterial research. Reasonably sized macroarrays were constructed and screened in these assays on the order of days. Through this work, we identified four compounds displaying in vitro MIC values against methicillin-resistant *S. aureus* that rival certain antibacterials in use today.

1.d. Significance

*Staphylococcus aureus* infections represent one of the largest health threats in hospital and community settings in the US. The effectiveness of current antibacterial agents against *S. aureus* has become severely limited due to the rapid rise of bacterial resistance. As resistant strains will only continue to emerge, there is an urgent need for the development of new antibacterial compounds. Combinatorial synthesis approaches are poised to have an impact in this area. Toward this end, we have applied the small molecule macroarray approach to the synthesis and screening of new antibacterial agents effective against *S. aureus*. Macroarrays of chalcones and heterocycles were constructed and subjected to a suite of antibacterial assays conducted either on or off of the macroarray support. These studies revealed two chalcones and two 2-methyl-3-cyanopyridines with in vitro MIC values against *S. aureus* comparable to those of established antibacterial agents. Furthermore, these compounds displayed similar activities against a methicillin-resistant strain of *S. aureus* and selectivity for certain Gram-positive bacteria. These results are significant, as these lead compounds were identified through the synthesis and analysis of only 198 compounds in total. Further studies will be required to establish the efficacy of these compounds in vitro and in vivo. Overall, this work underscores the utility of the small molecule macroarray as a tool for the identification of antibacterial agents.

1.e. Experimental Procedures

Synthesis

Planar cellulose membranes were derivatized with a Wang-type linker as previously described (loading=ca. 1.5 µmol/cm$^2$) [11]. Macroarrays 3, 5, 7, and 8 were synthesized according to modified procedures [10, 11]. Compounds displaying a range of antibacterial activities (Table 3) were resynthesized in solution using standard procedures and fully characterized (purities≧98%).

Bacteriological Assays

Bacteriological work was performed with strains obtained from ATCC. Luria-Bertani (LB) medium was used, as directed, for all bacterial work and was solidified with agar as needed. Overnight cultures were grown at 37° C. with shaking (*B. subtilis* was grown at 30° C.).

Disk Diffusion Assay

Compound spots were cleaved with TFA and neutralized with NH$_3$ as described herein. A 200-µL portion of diluted *S. aureus* 10390 (10$^6$ CFU/mL) was spread homogeneously across an agar plate. Compound spots were placed onto the agar, the plate was incubated at 37° C. for 18 h, and the diameters of the zones of inhibition were measured.

Agar Overlay TTC Assay

Macroarray copies were generated using the array transfer protocol described herein. Warm agar (15 mL) containing 10$^6$ CFU/mL bacteria was poured into a Petri dish (9 cm diameter). The dish was swirled to eliminate air bubbles, and a macroarray copy (6×6 cm) was fully submerged in the agar.

Following an 18 h incubation at 37° C., the plates were flooded with 0.1% (w/v) TTC in LB and allowed to develop for 1 h to visualize the zones of inhibition. Red zones indicated healthy bacteria, while white zones indicated that a compound on the macroarray inhibits growth of the bacterial strain [18].

MIC Determination

For estimated MIC determination, DMSO was added to the dried compound residue obtained from a single spot to afford ca. 100 μL of a 2 mM stock solution. Aliquots (5 μL) of these solutions were added to a 96-well plate, followed by 195 μL of diluted S. aureus 10390 ($10^6$ CFUs/mL) to yield ca. 50 μM final concentrations. The plates were swirled for 1 h to ensure compound dissolution, incubated for 12 h at 37° C., and the absorbance at 595 nm was recorded using a plate reader [5]. Compounds that showed complete growth inhibition at ca. 50 μM (Abs=0.04) were subjected to further testing at lower concentrations (ca. 25 and 12.5 μM). Actual MIC values were determined for lead compounds resynthesized in solution using an analogous procedure with solutions of known concentration (see).

TABLE 3

Antibacterial Activity Data of Selected Macroarray Compounds against S. aureus.

| Entry | Compound | Purity[a,b] (%) | S. aureus Estimated MIC range[c,d] (μM) | S. aureus MIC[c,e] (μM) | MRSA MIC[e,f] (μM) |
|---|---|---|---|---|---|
| 1 | 4At | 94 | 25-50 | 21.2 ± 1.2 | 18.7 ± 1.2 |
| 2 | 4Be | 88 | 25-50 | 21.0 ± 1.0 | 20.0 ± 1.0 |
| 3 | 4Bl | 93 | 12.5-25 | 15.0 ± 0.5 | 15.0 ± 0.5 |
| 4 | 4Bo | 91 | <12.5 | 10.0 ± 1.0 | 10.0 ± 1.0 |
| 5 | 4Bv | 88 | <12.5 | 3.5 ± 0.5 | 3.0 ± 0.5 |
| 6 | 4Cf | 86 | >50 | >250 | >250 |
| 7 | 6Al | 99 | 12.5-25 | 10.0 ± 0.5 | 10.0 ± 0.5 |
| 8 | 6Ao | 99 | <12.5 | 7.5 ± 1.2 | 7.5 ± 1.2 |
| 9 | 6Bt | 99 | <12.5 | 11.6 ± 0.9 | 13.4 ± 0.9 |
| 10 | 9Cf | 86 | 25-50 | 32.5 ± 1.2 | 31.2 ± 1.2 |
| 11 | linezolid | — | — | 10.0 ± 1.0 | 8.0 ± 1.0 |
| 12 | ciprofloxacin | — | — | 0.6 ± 0.1 | 0.9 ± 0.1 |

[a]From HPLC analyses of crude macroarray compounds (UV detection at 254 nm).
[b]Certain chalcones 4 were mixtures of cis and trans isomers (on average 80% trans;).
[c]S. aureus ATCC 10390.
[d]From serial dilution of spot stock solutions of crude macroarray compounds.
[e]From an authentic sample of the compound. Only trans isomers of chalcones 4 were evaluated. Error reflects step size in the serial dilutions.
[f]Methicillin-resistant S. aureus ATCC 33591 (MRSA).

TABLE 4

Antibacterial Activity Data of Lead Compounds against Selected Susceptible Bacterial Pathogens.[a]

| Entry | Compound | S. epidermidis MIC[b] (μM) | B. subtilis MIC[b] (μM) | K. pneumoniae MIC[b] (μM) |
|---|---|---|---|---|
| 1 | 4At | 27.5 ± 2.5 | 27.5 ± 2.5 | >250 |
| 2 | 4Be | 22.5 ± 2.5 | 22.5 ± 2.5 | 40 ± 10 |
| 3 | 4Bl | 12.5 ± 2.5 | 22.5 ± 2.5 | >250 |
| 4 | 4Bo | 12.5 ± 2.5 | 8.8 ± 2.5 | >250 |
| 5 | 4Bv | 3.8 ± 1.2 | 8.8 ± 1.2 | NA |
| 6 | 6Al | 12.5 ± 2.5 | 6.3 ± 1.2 | NA |
| 7 | 6Ao | 6.3 ± 1.2 | 3.8 ± 1.2 | NA |
| 8 | 6Bt | 17.5 ± 2.5 | 22.5 ± 2.5 | NA |
| 9 | 9Cf | >30 | 17.5 ± 2.5 | NA |

[a]S. epidermidis ATCC 12228, B. subtilis subsp. spizizenii ATCC 6633, and K. pneumoniae ATCC 4352.
[b]From an authentic sample of the compound. Only trans isomers of chalcones 4 were evaluated. Error reflects step size in the serial dilutions.

Analytical and Synthetic Instrumentation.

$^1$H NMR and $^{13}$C NMR spectra were recorded on a Bruker AC-300 spectrometer in deuterated solvents at 300 MHz and 75 MHz, respectively. Chemical shifts are reported in parts per million (ppm, δ) using tetramethyl silane (TMS) as a reference (0.0 ppm). Couplings are reported in hertz. LC-MS analyses were performed using a Shimadzu LCMS-2010a (Columbia, Md.) equipped with two pumps (LC-10ADvp), controller (SCL-10Avp), auto injector (SIL-10Advp), UV diode array detector (SPD-M10Avp), and single quadrupole analyzer (by electrospray ionization, ESI). The LC-MS is interfaced with a PC running the Shimadzu LCSolutions software package (Version 2.04 Su2-H2). A Supelco (Bellefonte, Pa.) 15 cm×2.1 mm C-18 wide-pore reverse-phase column was used for all LC-MS work. Standard reverse-phase HPLC conditions for LC-MS analyses were as follows: flow rate=200 μL/min; mobile phase A=0.4% formic acid in $H_2O$; mobile phase B=0.2% formic acid in acetonitrile. HPLC analyses were performed using a Shimadzu HPLC equipped with a single pump (LC-10Atvp), solvent mixer (FCV-10Alvp), controller (SCL-10Avp), auto injector (SIL-10AF), and UV diode array detector (SPD-M10Avp). A Shimadzu Premier 25 cm×4.6 mm C-18 reverse-phase column was used for all HPLC work. Standard reverse-phase HPLC conditions were as follows: flow rate=1.0 mL/min; mobile phase A=0.1% trifluoroacetic acid (TFA) in water; mobile phase B=0.1% TFA in acetonitrile. UV detection at 254 nm was used for all HPLC analyses. Compound purities were determined by integration of the peaks in HPLC traces measured at this wavelength.

Attenuated total reflectance (ATR)-IR spectra were recorded with a Bruker Tensor 27 spectrometer, outfitted with a single reflection MIRacle Horizontal ATR by Pike Technologies. A ZnSe crystal with spectral range 20,000 to 650 $cm^{-1}$ was used. UV spectra were recorded using a Cary 50 Scan UV-Vis spectrometer running Cary WinUV 3.00 software. Thin layer chromatography (TLC) was performed on silica gel 60 $F_{254}$ plates (E-5715-7, Merck). Sonication of reactions was performed in a laboratory ultrasound bath (Branson model # 1510R-MT). All reported melting points are uncorrected.

Macroarray reactions subjected to oven heating were performed on a pre-heated bed of sand in a standard drying oven (VWR model #13OOU). Temperature measurements of planar surfaces were acquired using a non-contact IR thermometer (Craftsman model #82327) with an error of ±2.5%. An Eppendorf pipetteman with a calibrated range between 0.5 μL and 10.0 μL was used to "spot" or apply reagents onto planar membranes in a spatially addressed manner using disposable plastic tips. Washing steps were 5 min each. After each washing sequence, the macroarray was dried under a stream of $N_2$ for 20 min.

Solution-phase, microwave-assisted reactions were performed in a Milestone MicroSYNTH Labstation multimode microwave (MW) synthesis reactor.[i] This instrument is equipped with a continuous power source (1000 W max) and interfaced with an Ethos MicroSYNTH Lab Terminal PC running EasyWave reaction monitoring software. Using this reactor system, MW irradiation can be applied to reactions using either power (wattage) control or temperature control. Specialized, 70 mL Teflon/polyetheretherketone (PEEK) vessels, designed to withstand temperatures up to 200° C. and pressures up to 280 psi, were used for all MW-assisted reactions.[ii] The internal temperature of the reaction vessel was monitored using a fiber-optic temperature sensor enclosed in a protective ceramic sheath. At pressures above the 280-psi limit, the vessels are designed to release excess pressure by venting and then resealing themselves. No evidence of venting was observed during the course of the reactions described herein.

All chemical reagents were purchased from commercial sources (Alfa-Aesar, Aldrich, and Acros) and used without further purification. Solvents were purchased from commercial sources (Aldrich and J. T. Baker) and used as obtained, with the exception of dichloromethane ($CH_2Cl_2$), which was distilled over calcium hydride immediately prior to use. Planar cellulose membranes (Whatman 1Chr and 3MM chromatography paper, 20×20 cm squares) were purchased from Fisher Scientific and stored in a dessicator at room temperature until ready for use. All reaction on planar supports were performed under air.

Construction of Small Molecule Macroarrays (3, 5, 7, and 8).

Representative synthesis of amino cellulose support. The cellulose amination procedure was adapted from the protocol of Ast et al.[iii] Dots were marked on a 15 cm×18 cm sheet of Whatman 1CHR paper at distances 1.4 cm apart using a #2 lead pencil. In this format, 120 compound spots (area=0.3 cm$^2$) can be accommodated on a single sheet without any detectable cross contamination. The sheet was immersed in 100 mL of 20% TFA in $CH_2Cl_2$ (v/v) for 10 min in a covered 2.6 L Pyrex dish. The acid solution was decanted carefully away from the sheet. The sheet was washed (2×) with 60 mL $CH_2Cl_2$, and dried. TsCl (19.0 g, 100 mmol) was dissolved in 50 mL pyridine in a covered 2.6 L Pyrex dish. The solution was swirled for 5 min, after which the acid-swelled sheet was added. The sheet was swirled in this TsCl solution for 1 h, and the solution was decanted. The support was washed by immersion in two consecutive baths of EtOH (100 mL), followed by $CH_2Cl_2$. The tosylated support was then dried under a stream of $N_2$.

The diamine spacer unit, 4,7,10-trioxa-1,13-tridecanediamine (60 mL), was added to a glass-covered 2.6 L Pyrex dish and heated in an oven to 80° C. The tosylated support was immersed in the pre-heated amine solution and heated for 30 min at 80° C. The amine solution was carefully decanted from the support. The support was washed by adding and then decanting 100 mL portions of DMF, EtOH, 1.0 N NaOH, $H_2O$, EtOH (2×), and $CH_2Cl_2$, and dried.

Representative Fmoc quantitation protocol on cellulose supports. The amine loading of the planar support was quantified according to standard UV Fmoc analysis procedures.[iv] A spot (6 mm diameter) was punched from the amino support using a desktop hole punch and immersed in 200 μL of 0.6 M N-(9-fluorenylmethoxycarbonyloxy)succinimide (Fmoc-OSu) in DMF for 2 h. The spot was washed with 10 mL of EtOH, 10 mL of acetone, and 10 mL of $CH_2Cl_2$. The spot was allowed to air dry for 20 min in a glass vial, after which 960 μL it of DMF and 40 μL of 1,8-diazabicyclo[5.4.0]undec-7-ene (DBU) were added. The spot was swirled in this mixture for 30 sec and then allowed to stand for 15 min. A 100 μL aliquot of this solution was removed and diluted with 2.0 mL of DMF. The absorbance was read at 296 nm ($\epsilon_{296}$=9500 M$^{-1}$ cm$^{-1}$) in a quartz cuvette. The value was multiplied by 21 to account for the dilution. Amine loadings of ca. 2-10 μmol/cm$^2$ were obtained using this method. Longer tosylation reaction times gave higher amine loadings (e.g., 1 h=2.3 μmol/cm$^2$, 12 h=10 μmol/cm$^2$).

Representative synthesis of Wang-type linker functionalized cellulose support. 4-formylphenoxyacetic acid (5.40 g, 30.0 mmol), diisopropylcarbodiimide (DIC, 4.7 mL, 30.0 mmol), N-hydroxysuccinimide (HOSu, 3.45 g, 30.0 mmol), $NEt_3$ (4.2 mL, 30.0 mmol), and DMF (50 mL) were combined in a 2.6 L Pyrex dish. The dish was covered and swirled for 30 min at room temperature. A 15 cm×18 cm sheet of amino cellulose support was added. The dish was covered again, and the mixture was swirled at room temperature for 2 h on a rotary shaker. The coupling solution was decanted, and the support was washed by adding and then decanting 70 mL portions of DMF (2×), EtOH (2×), and $CH_2Cl_2$. The aldehyde-derivatized support was then dried under a stream of $N_2$.

A 100 mL aliquot of 1.0 M $NaBH_4$ in 1.0 M aq. NaOH was added to the aldehyde-derivatized support. The mixture was swirled for 20 min, after which the $NaBH_4$ solution was decanted. The support was washed by adding and then decanting 100 mL portions of $H_2O$ (2×), EtOH (2×), and $CH_2Cl_2$, and then dried. To approximate the linker loading, the amount of residual amine was measured by Fmoc quantitation as described above, except that an 11-fold dilution was used. Residual amine loadings were found to be ca. 600-800 nmol/cm$^2$, giving linker loadings of ca. 1.5 μmol/cm$^2$.

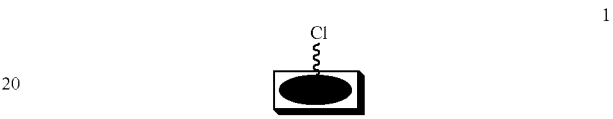

1

Preparation of chloride-derivatized support (1). A 15 cm×18 cm sheet of benzyl alcohol-derivatized support was immersed in a solution of $SOCl_2$ (10 mL, 137 mmol) in $CH_2Cl_2$ (40 mL) within a 2.6 L Pyrex dish. The dish was covered and swirled for 30 min at room temperature. The $SOCl_2$ solution was carefully decanted, and the support was washed by immersing and decanting 100 mL portions of $CH_2Cl_2$ (3×, 2 min in each wash). The chloride-derivatized, or "activated linker", support (1) was placed under a stream of $N_2$ to dry for 10 min and then used immediately in the next step.

Coupling of hydroxyacetophenones (A-C) to chloride-derivatized support (1). Coupling solutions of the three hydroxyacetophenones (A-C, 2.0 M) were prepared by mixing equal volumes of a 4.0 M solution of KOtBu in dry DMF with a 4.0 M solution of hydroxyacetophenone in dry DMF. Aliquots (3.0 μL) of these solutions were spotted across the appropriate rows of the chloride-derivatized support (1) in the following order:
Row A: 4'-hydroxyacetophenone
Row B: 3'-hydroxyacetophenone
Row C: acetovanillone

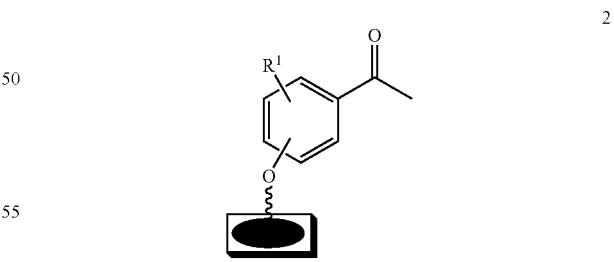

2

The spotted support was heated at 80° C. for 10 min, and the spotting and heating steps were repeated (2×). The support was then washed by adding and decanting 100 mL portions of 1.0 N aq. NaOH, $H_2O$, EtOH (2×), and $CH_2Cl_2$, and dried to give hydroxyacetophenone support (2). Acetophenone loading levels were examined by cleavage of a representative building block (A) from the support, analyzing the sample by HPLC, and comparing peak area to a UV calibration curve for A (loading=260 nmol/cm$^2$).[ii]

Representative synthesis of a chalcone macroarray (3). Individual solutions (ca. 300-900 μL) of 10 benzaldehydes (a-j, for 30-member macroarrays) or 23 benzaldehydes (a-w, for 69-member macroarrays) were prepared in 1.5 N KOH in 50% aq. EtOH. Aliquots (6.0 μL) of these solutions were spotted down the three rows of the hydroxyacetophenone macroarray (2) in columns as follows:

Column a: 1.0 M benzaldehyde
Column b: 0.5 M 2-fluorobenzaldehyde
Column c: 1.0 M 3-fluorobenzaldehyde
Column d: 1.0 M 4-fluorobenzaldehyde
Column e: 0.5 M 3-bromobenzaldehyde
Column f: 0.5 M 4-bromobenzaldehyde
Column g: 1.0 M 3-chlorobenzaldehyde
Column h: 0.5 M 4-chlorobenzaldehyde
Column i: 0.5 M m-anisaldehyde
Column j: 1.0 M p-anisaldehyde
Column k: 0.5 M piperonal
Column l: 0.5 M 2,3-dichlorobenzaldehyde
Column m: 0.5 M 2-bromobenzaldehyde
Column n: 0.25 M 3,4-dichlorobenzaldehyde
Column o: 0.25 M 2,3,6-trichlorobenzaldehyde
Column p: 0.25 M 6-bromo-2-pyridinecarboxaldehyde
Column q: 0.5 M 3-bromo-4-methoxybenzaldehyde
Column r: 0.25 M 3-bromo-4,5-dimethoxybenzaldehyde
Column s: 0.25 M 5-bromo-2-methoxybenzaldehyde
Column t: 0.25 M 2,4-dichlorobenzaldehyde
Column u: 0.5 M 3-trifluoromethylbenzaldehyde
Column v: 0.5 M 3,5-bis(trifluoromethyl)benzaldehyde
Column w: 0.5 M 2-chlorobenzaldehyde

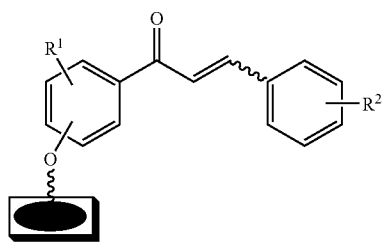

3

The spotted support was again heated at 80° C. for 10 min, and the spotting and heating steps were repeated (2×). The support was then washed by adding and decanting 100 mL portions of 1.0% aq. AcOH, DMSO, EtOH (2×), and CH$_2$Cl$_2$, and dried to yield 30- or 69-member chalcone macroarrays (3). Product loading (nmol/cm$^2$) was estimated by assuming 100% conversion from the hydroxyacetophenone.[ii]

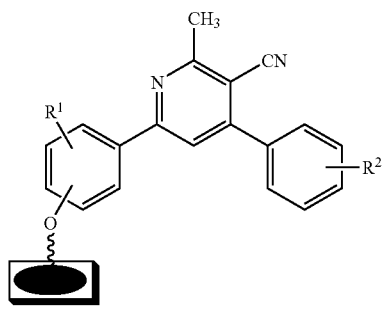

5

Representative synthesis of a 2-methyl-3-cyanopyridine macroarray (5). In a 250 mL glass bottle, 3-aminocrotononitrile (18.0 g, 220 mmol), KOH (12.3 g, 220 mmol), and 100 mL of EtOH were combined. The mixture was capped with a Teflon lid and vortexed until the mixture was homogeneous, and the solution was then poured into a 2.6 L Pyrex dish. A dry 69-member chalcone macroarray (3, 10 cm×13 cm) was submerged in the solution, covered, and slowly swirled on an orbital shaker at room temperature for 26 h. The solution was carefully decanted away from the support. The support was washed by adding and decanting 100 mL portions of 1.0% aq. AcOH, DMSO, EtOH (2×), and CH$_2$Cl$_2$, and dried to give cyanopyridine support (5). Product loading (nmol/cm$^2$) was estimated by assuming 100% conversion from the chalcone.[ii]

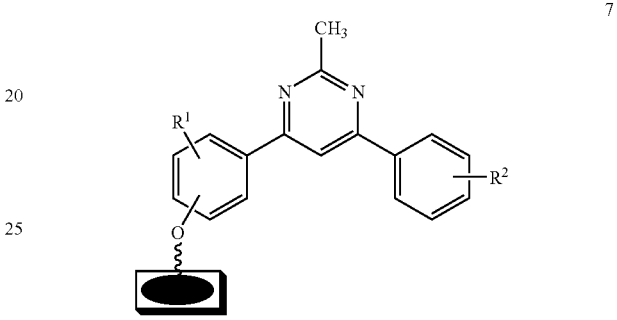

7

Representative synthesis of a methylpyrimidine macroarray (7). Methylpyrimidine macroarrays 7 were constructed from chalcone macroarrays 3 composed of benzaldehydes a-j.[v] Acetamidine hydrochloride (4.72 g, 50 mmol), KOtBu (5.62 g, 50 mmol), and 100 mL of dimethylacetamide (DMA) were combined in a 250 mL glass bottle and tightly capped with a Teflon lid. The resulting mixture was sonicated for 15 min and then poured into a 2.6 L Pyrex dish. A dry 30-member chalcone macroarray (3, 6 cm×13 cm) was added to the dish and submerged in the solution.[vi] The dish was covered and heated at 80° C. for 36 h in a drying oven. The solution was carefully decanted away from the support. The support was washed by adding and decanting 100 mL portions of 1.0 aq. % AcOH, DMSO, EtOH (2×), and CH$_2$Cl$_2$, and dried to yield macroarray (7). Product loading (nmol/cm$^2$) was estimated by assuming 100% conversion from the chalcone.[ii]

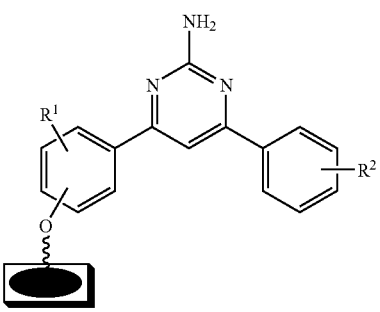

8

Representative synthesis of an aminopyrimidine macroarray (8). Aminopyrimidine macroarrays 8 were constructed from chalcone macroarrays 3 composed of benzaldehydes a-j. Guanidine hydrochloride (4.78 g, 50 mmol), KOtBu (5.62, 50 mmol), and 100 mL of DMA were combined in a 250 mL glass bottle and tightly capped with a Teflon lid. The resulting mixture was sonicated for 15 min and then poured into a 2.6 L Pyrex dish. A dry 30-member chalcone macroarray (3, 6 cm×13 cm) was added to the dish and submerged in the solution.[vi] The dish was covered and heated at 80° C. for 36 h in a drying oven. The solution was carefully decanted away from the support. The support was washed by adding and decanting 100 mL portions of 1.0% aq. AcOH, DMSO, EtOH (2×), and $CH_2Cl_2$, and dried to give aminopyrimidine macroarray (8). Product loading ($nmol/cm^2$) was estimated by assuming 100% conversion from the chalcone.[ii]

TFA vapor compound cleavage procedure. Cleavage was performed either on compound spots (for the Kirby-Bauer disk diffusion assay and the solution-phase MIC assay) or the intact macroarray (for the TTC agar overlay assay). Compound spots were punched out of macroarrays using a standard desktop hole punch (spot diameter=6 mm) and placed in individual 4 mL vials. A 10 mL portion of TFA was added to the bottom of a glass vacuum dessicator (interior diameter 21 cm, interior height 20 cm). Up to 240 vials containing the spots (or one 12 cm×18 cm, intact macroarray) were placed on a perforated ceramic platform in the dessicator that was situated 7 cm above the TFA. The dessicator was evacuated to 60 mm Hg over a 10 min period. The dessicator was disconnected from the vacuum, sealed, and allowed to stand for an additional 50 min at room temperature. The vials (or intact macroarray) were removed from the dessicator and allowed to vent in a fume hood for 15 min. For routine LC-MS characterization or the solution-phase MIC assays, the compounds were eluted from the spots by adding acetonitrile (1.0 mL) to each vial. The vials were sealed and shaken for 15 min, after which the paper disks were removed, and the acetonitrile was evaporated under reduced pressure. For the Kirby-Bauer disk diffusion assay or the TTC agar overlay assay, the cleaved spots or macroarrays were subjected to an ammonia ($NH_3$) neutralization step instead of elution (see biological assay section below). This cleavage method gave quantitative release of products (as determined by quantification of cleaved hydroxyacetophenone A).[ii]

Solution-phase Synthesis of Active Compounds.

2,4-dichloro-4'-hydroxychalcone (4At). Prepared according to literature procedure.[vii]

3-bromo-3'-hydroxychalcone (4Be). 3'-Hydroxyacetophenone (1.36 g, 10.0 mmol), 3-bromobenzaldehyde (1.30 mL, 11.1 mmol), and MeOH (30 mL) were combined in a 70 mL Teflon Milestone MW reaction vessel with a stir bar. After all of the reactants were dissolved, 50% (w/v) aq. NaOH (1.0 mL, 19 mmol) was added. The reaction vessel was closed tightly and heated with stirring in the Milestone MW reactor from room temperature to 110° C. over 10 min, held at 110° C. for 10 min, and allowed to cool to room temperature over 20 min. The reaction mixture was transferred to a 200 mL Erlenmeyer flask. Portions of EtOH (10 mL) and 1.0 N HCl (20 mL) were added to the dark red solution. An oily yellow mixture resulted and was stirred overnight at room temperature. A yellow solid slowly formed. This solid was isolated and recrystallized from 10 mL of EtOH to afford 1.06 g of 4Be as yellow crystals (35% yield). TLC: $R_f$=0.27 (hexane/EtOAc 4:1); Melting point: 130-134° C.; $^1$H NMR: (300 MHz, DMSO-d6) δ 9.77 (s, 1H), 8.18 (t, J=1.7 Hz, 1H), 7.92 (d, J=15.8 Hz, 1H), 7.83 (bd, J=7.8 Hz, 1H), 7.64 (d, 15.8 Hz, 1H), 7.62 (ddd, J=8.0, 1.4, 1.0 Hz, 1H), 7.61 (ddd, J=8.0, 1.7, 1.0 Hz, 1H), 7.46 (dd, J=2.3, 1.8 Hz, 1H), 7.39 (t, J=8.0 Hz, 1H), 7.36 (t, J=8.0 Hz, 1H), 7.05 (ddd, J=8.0, 2.3, 1.0 Hz, 1H); $^{13}$C NMR: (75 MHz, DMSO-d6) δ 189.64, 158.42, 142.66, 139.47, 137.89, 133.65, 131.59, 131.51, 130.51, 128.86, 124.41, 123.06, 121.41, 120.44, 115.39; IR (ATR): 3401, 1662, 1583, 1561, 1453, 1417, 369, 1341, 1309, 1285, 1267, 1231, 199, 1186, 1058, 997, 971 $cm^{-1}$; ESI-MS: expected, 302.0; observed, m/z 302.9 [M+H$^+$].

2,3-dichloro-3'-hydroxychalcone (4Bl). 3'-Hydroxyacetophenone (1.23 g, 9.0 mmol), 2,3-dichlorobenzaldehyde (1.93 g, 11.0 mmol), and MeOH (30 mL) were combined in a 100 mL round bottom flask with a stir bar. After all of the reactants were dissolved, 50% (w/v) aq. NaOH (2.0 mL, 38 mmol) was added. The flask was stoppered and stirred at room temperature for 8 h. The resulting mixture was poured onto 5.0 g of ice in a 250 mL Erlenmeyer flask with a stir bar. While the mixture was stirring, 40 mL of 1.0 N HCl was added slowly (in 10 mL portions every 5 min). A yellow precipitate formed. This precipitate was filtered and washed with MeOH (3 mL, 3×). The resulting yellow solid was recrystallized from MeOH to afford 1.04 g of 4Bl as a yellow crystalline powder (39% yield). TLC: $R_f$=0.22 (hexane/EtOAc 4:1); Melting point: 175-178° C.; $^1$H NMR: (300 MHz, Acetone-d6) δ 9.81 (brs, 1H), 8.14 (dd, J=8.0, 4.0 Hz, 1H), 7.97, 7.89 (AB peak, J=15.4 Hz, 2H), 7.71 (dd, J=8.0, 1.4 Hz, 1H), 7.63 (t, J=8.0, 1.4 Hz, 1H), 7.44 (m, 2H), 7.36 (t, J=8.0 Hz, 1H), 7.06 (ddd, J=8.0, 2.4, 0.8 Hz, 1H); $^{13}$C NMR: (75 MHz, DMSO-d6) δ 188.83, 158.02, 139.48, 138.88, 135.91, 133.47, 132.78, 131.92, 130.07, 128.41, 126.98, 126.44, 120.54, 120.27, 115.06; IR (ATR): 3385, 1688, 1656, 1588, 1451, 1413, 1315, 1283, 1262, 1230, 1180, 1048, 998, 979 $cm^{-1}$, ESI-MS: expected, 292.0; observed, m/z 292.9 [M+H$^+$].

3'-hydroxy-2,3,6-trichlorochalcone (4Bo). 3'-Hydroxyacetophenone (227 mg, 1.67 mmol), 2,3,6-trichlorobenzaldehyde (419 mg, 2.0 mmol), and MeOH (3.0 mL) were combined in a 4 mL vial. After all of the reactants were dissolved, 50% (w/v) aq. NaOH (200 μL, 3.8 mmol) was added slowly (as the reaction was very exothermic). The solution was tightly capped with a Teflon cap and vortexed for 36 h at room temperature. The resulting deep red solution was transferred to a 25 mL Erlenmeyer flask containing 2.0 g of ice and a stir bar. A 5.0 mL portion of 1.0 N HCl was added to the flask, and a white precipitate formed. This solid was isolated by filtration and recrystallized twice from MeOH to afford 132 mg of 4Bo as yellow crystals (24% yield). TLC: $R_f$=0.33 (hexane/EtOAc 4:1); Melting point: 147-152° C.; $^1$H NMR: (300 MHz, DMSO-d6) δ 9.85 (s, 1H), 7.68, 7.60 (AB peak, J=8.6 Hz, 2H), 7.65, 7.59 (AB peak, J=16.1 Hz, 2H), 7.49 (dt, J=7.7, 1.0 Hz), 7.39 (t, J=2.4 Hz, 1H), 7.36 (t, J=7.7 Hz, 1H), 7.06 (ddd, J=7.7, 2.4, 1.0 Hz, 1H); $^{13}$C NMR: (75 MHz, DMSO-d6) δ 189.52, 160.02, 158.52, 138.80, 137.44, 135.30, 132.98, 132.76, 132.16, 131.68, 130.79, 130.36, 121.60, 120.33, 115.27; IR (ATR): 3430, 1660, 1615, 1588, 1447, 1380, 1291, 1217, 1186, 1094, 1059, 999, 974 $cm^{-1}$; ESI-MS: expected, 326.0; observed, m/z 326.8 [M+H$^+$].

3'-hydroxy-3,5-bis(trifluoromethyl)chalcone (4Bv). 3'-Hydroxyacetophenone (227 mg, 1.67 mmol), 3,5-bis(trifluoromethyl)benzaldehyde (330 μL, 2.0 mmol), and MeOH (3.0 mL) were combined in a 4 mL vial. After all of the reactants were dissolved, 50% (w/v) aq. NaOH (200 μL, 3.8 mmol) was added. The solution was tightly capped with a Teflon cap and vortexed for 12 h at room temperature. The resulting deep red solution was transferred to a 25 mL Erlenmeyer flask and 5.0 mL of 1.0 N HCl was added. A yellow precipitate formed. This solid was isolated by filtration and recrystallized from EtOH to afford 256 mg of 4Bv as yellow crystals (43% yield). TLC: $R_f$=0.37 (hexane/EtOAc 4:1); Melting point: 169-173° C.; $^1$H NMR: (300 MHz, DMSO-d6) δ 9.80 (brs, 1H), 8.63 (brs, 2H), 8.20 (d, J=15.8 Hz, 1H), 8.10 (brs, 1H), 7.85 (d, J=15.8 Hz, 1H), 7.70 (d, J=7.4 Hz, 1H), 7.52 (brs, 1H), 7.38 (t, J=7.9 Hz, 1H), 7.07 (dd, J=7.9, 1.7 Hz, 1H);

$^{13}$C NMR: (75 MHz, DMSO-d6) δ 189.55, 158.48, 140.87, 139.23, 131.55 (q, J=33 Hz), 130.46, 129.95, 126.65, 123.90 (q, J=272 Hz), 123.59, 121.34, 120.58, 115.56; IR (ATR): 3298, 1657, 1599, 1575, 1472, 1454, 1378, 1337, 1320, 1286, 1277, 1203, 1170, 1122, 1053, 998 cm$^{-1}$; ESI-MS: expected, 360.1; observed, m/z 360.9 [M+H$^+$].

4-bromo-4'-hydroxy-3'-methoxy-chalcone (4Cf). Acetovanillone (1.50 g, 9.0 mmol), 4-bromobenzaldehyde (2.04 g, 11.0 mmol), and MeOH (30 mL) were combined in a 100 mL round bottom flask with a stir bar. After all of the reactants were dissolved, 50% (w/v) aq. NaOH (2.0 mL, 38 mmol) was added. The flask was stoppered and stirred at room temperature for 8 h. The resulting mixture was poured onto 5.0 g of ice in a 250 mL Erlenmeyer flask with a stir bar. While the mixture was stirring, 40 mL of 1.0 N HCl was added slowly (in 10 mL portions every 5 min). A yellow precipitate formed. This precipitate was filtered and washed with MeOH (3 mL, 3×). The resulting yellow solid was recrystallized from MeOH to afford 1.05 g of 4Cf as yellow needles (35% yield). TLC: R$_f$=0.47 (CH$_2$Cl$_2$); Melting point: 166-168° C.; $^1$H NMR: (300 MHz, DMSO-d6) δ 10.04 (s,1H), 7.93 (d, J=15.4 Hz, 1H), 7.82 (d, J=8.6 Hz, 2H), 7.77 (dd, J=8.2, 2.0 Hz), 7.62 (m, 4H), 6.89 (d, J=8.5 Hz, 1H), 3.86 (s, 3H); $^{13}$C NMR: (75 MHz, DMSO-d6) δ 187.62, 152.73, 148.74, 141.96, 134.89, 132.48, 131.32, 130.03, 124.51, 124.56, 123.58, 115.70, 112.40, 56.43; IR (ATR): 3293, 1649, 1610, 1575, 1562, 1519, 1484, 1462, 1429, 1400, 1330, 1300, 1279, 1176, 1108, 1071, 1051, 1034, 1010, 980 cm$^{-1}$; ESI-MS: expected, 332.0; observed, m/z 332.9 [M+H$^+$].

3-bromo-4'-(tetrahydropyranyloxy)chalcone (THP-4Ae). 4'-Tetrahydropyranyloxy-acetophenone (1.1 g, 5.0 mmol, synthesized according to our previously reported method),[ii] 3-bromobenzaldehyde (650 μL, 5.5 mmol), and MeOH (20 mL) were combined in a 50 mL round bottom flask with a stir bar. After all of the reactants were dissolved, 50% (w/v) aq. NaOH (1.5 mL, 27.5 mmol) was added. The flask was stoppered and stirred at room temperature for 5 h. The resulting precipitate was filtered, washed with EtOH (1 mL, 3×), and allowed to air dry to afford 1.06 g of THP-4Ae as a white powder (55% yield). The product was used without further purification. TLC: R$_f$=0.23 (hexane/EtOAc 4:1); Melting point: 166-168° C.; $^1$H NMR: (300 MHz, CDCl$_3$) δ 8.01, 7.14 (AA'XX' peak, J$_{aa'}$=J$_{xx'}$=2.5, J$_{ax}$=8.5, J$_{ax'}$=0.3 Hz, 2H), 7.78 (t, J=1.7 Hz, 1H), 7.70 (d, J=15.5 Hz, 1H), 7.54 (bs, 1H), 7.51 (m, 2H), 7.29 (d, J=7.9 Hz, 1H), 5.54 (t, J=3 Hz, 1H), 3.87 (ddd, J=11.3, 8.5, 3 Hz, 1H), 3.63 (dtd, J=11.3, 44.0, 1.4 Hz, 1H), 2.03 (m, 1H), 1.70 (m, 1H); $^{13}$C NMR: (75 MHz, CDCl$_3$) δ 188.60, 161.35, 142.33, 137.48, 133.24, 131.64, 130.93, 130.63, 127.38, 123.45, 123.28, 116.39, 96.32, 62.27, 30.32, 25.28, 18.70; IR (ATR): 2946, 1660, 1607, 1595, 1576, 1557, 1509, 1480, 1420, 1357, 1331, 1314, 1284, 1224, 1202, 1175, 1112, 1076, 1038, 1022, 1010, 965 cm$^{-1}$; ESI-MS: expected, 386.1; observed, m/z 387.0 [M+H$^+$].

4-(3-bromophenyl)-6-(4-hydroxyphenyl)-2-methyl-3-cyanopyridine (6Ae). THP-4Ae (775 mg, 2.0 mmol), 3-aminocrotononitrile (164.2 mg, 2.0 mmol), NaOH (80 mg, 2.0 mmol), and EtOH (40 mL) were combined in a 100 mL round bottom flask with a stir bar. The resulting solution was stirred rapidly and refluxed for 24 h, after which it was allowed to cool to room temperature. The solution then was stirred under an O$_2$ atmosphere at room temperature for 8 h (using a balloon of O$_2$). A 40 mL portion of 1.0 N aq. HCl was added to the flask, and a yellow precipitate formed. This precipitate was filtered and recrystallized from acetone (3×) to yield 120 mg of 6Ae as colorless crystals (16% yield). TLC: R$_f$=0.16 (hexane/EtOAc 4:1); Melting point: 214-218° C.; $^1$H NMR: (300 MHz, Acetone-d6) δ 8.79 (bs, 1H), 8.18, 6.98 (AA'XX' peak, J$_{aa'}$=J$_{xx'}$=2.5, J$_{ax}$=8.5, J$_{ax'}$=0.2 Hz, 2H), 7.91 (t, J=1.8 Hz, 1H), 7.87 (s, 1H), 7.74 (m, 2H), 7.53 (t, J=7.9 Hz, 1H), 2.82 (s, 3H); $^{13}$C NMR: (75 MHz, Acetone-d6) δ 162.27, 160.13, 158.96, 151.96, 139.43, 132.72, 131.63, 130.90, 129.54, 129.08, 127.89, 122.45, 116.97, 116.71, 115.87, 104.66, 23.75; IR (ATR): 3000, 2220, 1611, 1578, 1537, 1496, 1381, 1296, 1233, 1174, 1141, 1078, 1063 cm$^{-1}$; ESI-MS: expected, 364.0; observed, m/z 364.9 [M+H$^+$].

2,3-dichloro-4'-(tetrahydropyranyloxy)chalcone (THP-4Al). 4'-Tetrahydropyranyloxy-acetophenone (1.98 g, 9.0 mmol),[ii] 2,3-dichlorobenzaldehyde (1.93 g, 11.0 mmol), EtOH (15 mL), and MeOH (15 mL) were combined in a 100 mL round bottom flask with a stir bar. After all of the reactants were dissolved, 50% (w/v) aq. NaOH (1.0 mL, 19 mmol) was added. The flask was stoppered and stirred at room temperature for 8 h. The resulting white precipitate was filtered, washed with EtOH (1 mL, 3×), and allowed to air dry to afford 2.95 g of THP-4Al as a white powder (87% yield). The product was used without further purification. TLC: R$_f$=0.40 (hexane/EtOAc 4:1); Melting point: 116-118° C.; $^1$H NMR: (300 MHz, Acetone-d6) δ 8.15, 7.18 (AA'XX' peak, J$_{aa'}$=J$_{xx'}$=2.5, J$_{ax}$=8.4, J$_{ax'}$=0.4 Hz, 2H), 8.13 (d, J=16 Hz, 1H), 8.04 (dd, J=7.9, 1.4 Hz, 1H), 7.89 (d, J=16 Hz, 1H), 7.64 (dd, J=7.9, 1.4 Hz, 1H), 7.43 (t, J=7.9 Hz, 1H), 5.61 (t, J=3.0 Hz, 1H), 3.82 (ddd, J=11.5, 8.4, 2.6 Hz, 1H), 3.61 (dtd, J=11.5, 4.0, 1.3 Hz, 1H), 1.86 (m, 3H), 1.66 (m, 3H); $^{13}$C NMR: (75 MHz, DMSO-d6) δ 187.23, 161.54, 138.27, 136.06, 133.45, 132.73, 131.77, 131.48, 130.95, 128.36, 126.93, 126.31, 116.38, 96.22, 61.89, 30.14, 25.13, 18,67; IR (ATR): 2964, 1656, 1608, 1595, 1573, 1556, 1507, 1455, 1425, 1411, 1372, 1326, 1314, 1248, 1222, 1205, 1173, 1155, 1121, 1106, 1035, 1020, 961 cm$^{-1}$; ESI-MS: expected, 376.1; observed, m/z 376.9 [M+H$^+$].

4-(2,3-dichlorophenyl)-6-(4-hydroxyphenyl)-2-methyl-3-cyanopyridine (6Al). THP-4Al (755 mg, 2.0 mmol), 3-aminocrotononitrile (164.2 mg, 2.0 mmol), NaOH (80 mg, 2.0 mmol), and EtOH (40 mL) were combined in a 100 mL round bottom flask and stirred rapidly. The resulting solution was refluxed for 24 h and then allowed to cool to room temperature. The solution was stirred under an O$_2$ atmosphere at room temperature for an additional 8 h (using a balloon of O$_2$). A 40 mL portion of 1.0 N aq. HCl was added to the flask, and a dark red precipitate formed. The precipitate was filtered and recrystallized from EtOH to yield 162 mg of 6Al as white crystals (23% yield). TLC: R$_f$=0.29 (hexane/EtOAc 4:1); Melting point: 220-223° C.; $^1$H NMR: (300 MHz, Acetone-d6) δ 8.17, 6.98 (AA'XX' peak, J$_{aa'}$=J$_{xx'}$=2.5, J$_{ax}$=8.5, J$_{ax'}$=0.3 Hz, 2H), 7.85 (s, 1H), 7.77 (dd, J=7.8, 1.8 Hz, 1H), 7.56 (t, J=7.8 Hz, 1H), 7.50 (dd, J=7.7, 1.8 Hz, 1H), 2.83 (s, 3H); $^{13}$C NMR: (75 MHz, Acetone-d6) δ 161.70, 160.26, 158.99, 151.32, 138.63, 133.27, 131.66, 130.63, 129.56, 129.51, 128.92, 128.61, 117.20, 116.19, 115.96, 106.08, 23.60; IR (ATR): 3069, 2228, 1614, 1589, 1576, 1536, 1457, 1405, 1378, 1287, 1230, 1179, 1169, 1154, 1112, 1052 cm$^{-1}$; ESI-MS: expected, 354.0; observed, m/z 354.9 [M+H$^+$].

4'-(tetrahydropyranyloxy)-2,3,6-trichlorochalcone (THP-4Ao). 4'-Tetrahydropyranyl-oxyacetophenone (1.98 g, 9.0 mmol),[ii] 2,3,6-trichlorobenzaldehyde (1.93 g, 11.0 mmol), EtOH (15 mL), and MeOH (15 mL) were combined in a 100 mL round bottom flask with a stir bar. After all of the reactants were dissolved, 50% (w/v) aq. NaOH (1.0 mL, 19 mmol) was added. The flask was stoppered and stirred at room temperature for 8 h. The resulting precipitate was filtered, washed with EtOH (5 mL), 50% aq. EtOH (5 mL), EtOH (5 mL, 2×), and allowed to air dry. This procedure afforded 2.6 g of THP-4Ao as a white powder (70% yield). The product was used without further purification. (Note: The powder is light sensitive and slowly turns red with exposure to ambient light. Efforts were made to shield the compound from light after isolation.) TLC: $R_f$=0.56 (hexane/EtOAc 4:1); Melting point: 101-104° C.; $^1$H NMR: (300 MHz, Acetone-d6) δ 8.10, 7.19 (AA'XX' peak, $J_{aa'}$=$J_{xx'}$=2.5, $J_{ax}$=8.7, $J_{ax'}$=0.3 Hz, 2H), 7.75, 7.71 (AB peak, J=16.2 Hz, 2H), 7.63, 7.56 (AB peak, J=8.8 Hz, 2H), 5.62 (t, J=3.0 Hz, 1H), 3.82 (ddd, J=11.6, 8.9, 2.8 Hz, 1H), 3.61 (dtd, J=11.6, 4.2, 1.2 Hz, 1H); 1.95 (m, 3H), 1.62 (m, 3H); $^{13}$C NMR: (75 MHz, Acetone-d6) δ 187.24, 161.68, 136.37, 135.50, 132.96, 132.90, 132.31, 131.59, 131.16, 130.98, 130.90, 129.73, 116.50, 96.24, 61.91, 30.12, 25.12, 18.66; IR (ATR): 2944, 1663, 1601, 1576, 1513, 1437, 1424, 1376, 1293, 1251, 1221, 1205, 1186, 1171, 1119, 1093, 1023 cm$^{-1}$; ESI-MS: expected, 410.0; observed, m/z 410.9 [M+H$^+$].

2-methyl-6-(4-(tetrahydro-2H-pyran-2-yloxy)phenyl)-4-(2,3,6-trichlorophenyl)-3-cyano-pyridine (THP-6Ao). THP-4Ao (1.23 g, 3.00 mmol), 3-aminocrotononitrile (2.46 g, 30.0 mmol), KOtBu (0.60 g, 5.35 mmol), and acetonitrile (50 mL) were combined in a 100 mL round bottom flask with a stir bar. The solution was stirred rapidly under an $O_2$ atmosphere for 15 h (using a balloon of $O_2$), after which the solution was filtered. To the filtrate, 1.0 N aq. HCl (50 mL) was added, and a white precipitate quickly formed. After stirring for 1 h at room temperature, the reaction was cooled to 8° C. and allowed to stand at this temperature for 1 h. The resulting white precipitate was filtered, washed with $H_2O$ (5 mL, 3×) and EtOH (5 mL, 2×), and allowed to air dry to afford 460 mg of THP-6Ao as a white solid (32% yield). The product was used without further purification. TLC: $R_f$=0.48 (hexane/EtOAc 4:1); Melting point: 148-152° C.; $^1$H NMR: (300 MHz, Acetone-d6) δ 8.24, 7.19 (AA'XX' peak, $J_{aa'}$=$J_{xx'}$=2.5, $J_{ax}$=8.8 $J_{ax'}$=0.2 Hz, 2H), 7.96 (s, 1H), 7.82, 7.70 (AB peak, J=8.7 Hz, 2H), 5.58 (t, J=3.2 Hz, 1H), 3.84 (ddd, J=11.8, 8.7, 2.8 Hz, 1H), 3.60 (dtd, J=11.8, 3.9, 1.4 Hz, 1H), 2.86 (s, 3H), 1.88 (m, 3H), 1.65 (m, 3H); $^{13}$C NMR: (75 MHz, Acetone-d6) δ 159.78, 159.43, 152.85, 149.54, 132.52, 132.25, 130.48, 129.64, 129.16, 125.94, 117.43, 116.87, 115.57, 109.99, 106.25, 96.24, 61.82, 39.46, 30.24, 25.18, 23.6, 18.74; IR (ATR): 2948, 2874, 2217, 1606, 1583, 1544, 1436, 1396, 1331, 1231, 1170, 1118, 1053, 1022, 1009, 965 cm$^{-1}$; ESI-MS: expected, 472.1; observed, m/z 473.1 [M+H$^+$].

6-(4-hydroxyphenyl)-2-methyl-4-(2,3,6-trichlorophenyl)-3-cyanopyridine (6Ao). THP-6Ao (400 mg, 0.84 mmol) was dissolved in 3 mL of 80% (v/v) TFA in $CH_2Cl_2$ in a 4 mL vial. The vial was tightly capped with a Teflon cap and vortexed at room temperature for 10 min. The solution was concentrated under a slow stream of $N_2$. The resulting red oil was dissolved in 2 mL of EtOAc and washed with 2 mL of $H_2O$. The aqueous layer was extracted with an additional 2 mL of EtOAc. The organic layers were combined, dried over $Na_2SO_4$, filtered, and concentrated to yield a light tan foam. The foam was purified by silica gel chromatography (hexane/EtOAc 4:1) to afford 220 mg of 6Ao as a yellow-white solid (67% yield). TLC: $R_f$=0.29 (hexane/EtOAc 4:1); Melting point: 191-195° C.; $^1$H NMR: (300 MHz, Acetone-d6) δ 8.72 (bs, 1H), 8.18, 6.99 (AA'XX' peak, $J_{aa'}$=$J_{xx'}$=2.5, $J_{ax}$=8.6 $J_{ax'}$=0.2 Hz, 2H), 7.90 (s, 1H), 7.80, 7.68 (AB peak, J=8.8 Hz, 2H), 2.85 (s, 3H); $^{13}$C NMR: (75 MHz, CDCl$_3$) δ 162.78, 160.08, 158.81, 149.70, 136.37, 132.87, 132.45, 131.99, 129.80, 129.66, 129.17, 117.92, 116.31, 116.01, 106.44, 24.35; IR (ATR): 3323, 2221, 1704, 1611, 1587, 1542, 1437, 1399, 1378, 1332, 1280, 1229, 1173, 1112, 1094, 1046 cm$^{-1}$; ESI-MS: expected, 388.0; observed, m/z 388.9 [M+H$^+$].

3'-(tetrahydropyranyloxy)-2,4-dichlorochalcone (THP-4Bt). 3'-Tetrahydropyranyloxy-acetophenone (3.96 g, 18.0 mmol, synthesized according to a literature procedure),$^{viii}$ 2,4-dichlorobenzaldehyde (3.5 g, 20.0 mmol), and EtOH (30 mL) were combined in a 100 mL round bottom flask with a stir bar. After all of the reactants were dissolved, KOH (2.0 g, 36.0 mmol) was added. The flask was stoppered and stirred at room temperature for 8 h, during which time a viscous oil developed. The solution was carefully decanted from the oil. The oil was dissolved in 100 mL of EtOAc and washed with $H_2O$, 5% aq. citric acid, brine, and $H_2O$. The organic phase was isolated, dried over $Na_2SO_4$ and concentrated to give a viscous yellow oil. The oil was further purified by silica gel chromatography (hexane/EtOAc 4:1) to afford 572 mg of THP-4Bt as a yellow oil (8.5% yield). We found that THP-4Bt was prone to decomposition, and thus this compound was used immediately in the next step without full characterization. TLC: $R_f$=0.52 (hexane/EtOAc 4:1); $^1$H NMR: (300 MHz, Acetone-d6) δ 8.13 (d, J=8.8 Hz, 1H), 8.09 (d, J=16.0 Hz, 1H), 7.88 (d, J=16.0 Hz, 1H), 7.77 (m, 2H), 7.62 (d, J=2.0 Hz, 1H), 7.48 (m, 2H), 7.34 (ddd, J=8.3, 2.4, 1.1 Hz, 1H), 5.57 (t, J=3.0 Hz, 1H), 3.82 (m, 1H), 3.60 (dtd, J=11.3, 3.0, 1.1 Hz, 1H), 1.69 (m, 6H); ESI-MS: expected, 376.1; observed, m/z 376.9 [M+H$^+$].

4-(2,4-dichlorophenyl)-6-(3-hydroxyphenyl)-2-methyl-3-cyanopyridine (6Bt). THP-4Bt (570 mg, 1.52 mmol), 3-aminocrotononitrile (2.24 g, 15.63 mmol), KOtBu (0.30 g, 2.70 mmol), and acetonitrile (50 mL) were combined in a 100 mL round bottom flask with a stir bar. The solution was stirred rapidly under an $O_2$ atmosphere for 20 h (using a balloon of $O_2$), after which the reaction was filtered. To the filtrate, 1.0 N aq. HCl (50 mL) was added, and a yellow-white precipitate quickly formed. After stirring for 1 h at room temperature, the reaction was cooled to 8° C. and allowed to stand at this temperature for 1 h. The resulting white precipitate was filtered, washed with $H_2O$ (5 mL, 3×), EtOH (5 mL, 2×), and allowed to air dry. The precipitate was further purified by silica gel chromatography (hexane/EtOAc 4:1) to afford 182 mg of 6Bt as a yellow-white solid (34% yield). TLC: $R_f$=0.27 (hexane/EtOAc 4:1); Melting point: 208-210° C.; $^1$H NMR: (300 MHz, Acetone-d6) δ 8.56 (bs, 1H), 7.91 (s, 1H), 7.78 (m, 2H), 7.69 (ddd, J=7.8, 1.7, 1.0 Hz, 1H), 7.60 (d, J=1.3 Hz), 7.35 (t, J=7.8 Hz, 1H), 7.00 (ddd, J=8.0, 2.5 1.0 Hz, 1H), 2.85 (s, 3H); $^{13}$C NMR: (75 MHz, CDCl$_3$) δ 162.58, 158.89, 156.44, 139.34, 136.67, 134.08, 133.51, 131.47, 130.52, 130.46, 127.89, 121.12, 120.15, 119.04, 117.85, 116.37, 114.61, 107.72, 24.47; IR (ATR): 3364, 2237, 1587, 1575, 1484, 1437, 1396, 1345, 1307, 1286, 1237, 1216, 1182, 1140, 1114, 1102, 1052, 998 cm$^{-1}$; ESI-MS: expected, 354.0; observed, m/z 354.9 [M+H]$^+$.

3'-methoxy-4'-tetrahydropyranylacetophenone (THP-C). In an oven-dried, 500 mL round bottom flask equipped with a stir bar and an addition funnel, p-toluenesulfonic acid monohydrate (156 mg, 0.82 mmol), pyridine (66 µL, 0.82 mmol), acetovanillone (6.10 g, 36.7 mmol), and $CH_2Cl_2$ (170 mL) were combined and rapidly stirred. Dihydropyran (10 mL, 110 mmol) was diluted with 40 mL of $CH_2Cl_2$, poured into the addition funnel, and added drop wise to the acetovanillone solution over a period of 2 h. The reaction was stirred for an additional 12 h at room temperature, after which it was washed with 200 mL of 1.0 N NaOH (2×). The organic phase was dried over $Na_2SO_4$, filtered, and concentrated to a clear oil under reduced pressure. The oil crystallized upon standing to afford 4.2 g of THP-C as a white solid (46% yield). The solid was used without further purification. TLC: $R_f$=0.19 (hexane/EtOAc 4:1); Melting point: 67-69° C.; $^1$H NMR: (300 MHz, CDCl$_3$) δ 7.52 (s, 1H), 7.50 (d, J=10 Hz, 1H), 7.13

(d, J=8 Hz, 1H), 5.50 (t, J=3 Hz, 1H), 3.90 (s, 3H), 3.89 (m, 1H), 3.59 (m, 1H), 2.54 (s, 3H), 1.95 (m, 3H), 1.63 (m, 1H); $^{13}$C NMR: (75 MHz, CDCl$_3$) δ 197.08, 150.92, 150.12, 131.60, 123.18, 115.65, 111.29, 97.14, 62.31, 56.32, 30.33, 26.45, 25.31, 18.79; IR (ATR): 2966, 2936, 2880, 1672, 1585, 1510, 1462, 1442, 1413, 1390, 1352, 1290, 1272, 1243, 1221, 1201, 1172, 1153, 1120, 1110, 1051, 1032, 1020, 959 1046 cm$^{-1}$; ESI-MS: expected, 250.1; observed, m/z 251.1 [M+H$^+$].

4-bromo-3'-methoxy-4'-(tetrahydropyranyloxy)chalcone (THP-4Cf). THP-C (1.0 g, 4.0 mmol), 4-bromobenzaldehyde (814 mg, 4.4 mmol), and EtOH (20 mL) were combined in a 100 mL round bottom flask with a stir bar. After all of the reactants were dissolved, 50% (w/v) aq. NaOH (1.0 mL, 19 mmol) was added. The flask was stoppered and stirred at room temperature for 8 h. The resulting precipitate was filtered, washed with EtOH (1.0 mL, 3×), and allowed to air dry to afford 1.55 g of THP-4Cf as a white powder (93% yield; ~80% purity, as determined by $^1$H NMR). The product was used in the next step without further purification. TLC: R$_f$=0.27 (hexane/EtOAc 4:1); Melting point: 142-145° C.; $^1$H NMR: (300 MHz, CDCl$_3$) δ 7.72 (d, 15.8 Hz, 1H), 7.62 (s, 1H), 7.61 (d, J=7.1 Hz), 7.51 (d, J=15.8 Hz, 1H), 7.50 (m, 4H), 7.20 (d, J=9 Hz, 1H), 5.5 (t, J=3 Hz, 1H), 3.95 (s, 3H), 3.91 (m, 1H), 3.62 (m, 1H), 1.99 (m, 3H), 1.69 (m, 3H); $^{13}$C NMR: (75 MHz, CDCl$_3$) δ 188.74, 151.08, 150.45, 142.73, 134.26, 132.38, 129.93, 124.75, 123.02, 122.59, 115.65, 112.01, 97.20, 62.36, 56.45, 30.53, 25.32, 18.79; IR (ATR): 2946, 1658, 1585, 1513, 1419, 1357, 1327, 1256, 1205, 1167, 1150, 1121, 1073, 1033, 1023, 958 cm$^{-1}$; ESI-MS: expected, 416.1; observed, m/z 416.9 [M+H$^+$].

4-(4-bromophenyl)-6-(4-hydroxy-3-methoxyphenyl)-2-methylpyrimidine (9Cf). Acet-amidine hydrogen chloride (2.36, 25 mmol), KOtBu (2.81, 25 mmol), and dimethylacetamide (DMA, 50 mL) were combined in a 100 mL glass bottle and tightly capped with a Teflon lid. The resulting mixture was sonicated for 15 min and then allowed to stand until the KCl solids had settled to the bottom. A 30 mL portion of this solution was decanted away and added to THP-4Cf (250 mg, 0.60 mmol) in a 100 mL round bottom flask with a stir bar. The resulting solution was heated at 110° C. for 20 h under an O$_2$ atmosphere (using a balloon of O$_2$). The DMA was distilled away from the solution under reduced pressure, and a 10 mL aliquot of TFA was added to the reaction flask, followed by 10 mL of H$_2$O. The solution was stirred for 1 h at room temperature and then poured over 50 g of ice in an Erlenmeyer flask. A 100 mL portion of 1.0 N NaOH was added, followed by 150 mL of EtOAc. The organic layer was separated, washed with sat. NaHCO$_3$ (150 mL), and concentrated under reduced pressure to yield a pale brown oil. The oil was further purified by silica gel chromatography using CH$_2$Cl$_2$ as an eluent, followed by hexane/EtOAc (4:1), to afford 146 mg of 9Cf as a white solid (65% yield). TLC: R$_f$=0.17 (hexane/EtOAc 4:1); Melting point: 155-158° C.; $^1$H NMR: (300 MHz, Acetone-d6) δ 8.24, 7.70 (AA'XX' peak, J$_{aa'}$=J$_{xx'}$=2.3, J$_{ax}$=8.2 J$_{ax'}$=0.6 Hz, 2H), 8.22 (s, 1H), 7.95 (d, J=2.0 Hz, 2H), 7.86 (dd, J=2.0, 8.3 Hz, 1H), 6.97 (d, J=8.3 Hz, 1H), 3.96 (s, 3H), 2.72 (s, 3H); $^{13}$C NMR: (75 MHz, DMSO-d6) δ 168.08, 164.71, 162.99, 149.90, 148.03, 136.87, 132.02, 129.27, 128.97, 124.76, 121.29, 115.41, 110.70, 108.42, 55.79, 25.80; IR (ATR): 3484, 1591, 1582, 1570, 1517, 1486, 1448, 1424, 1400, 1361, 1274, 1213, 1193, 1181, 1153, 1130, 1104, 1094, 1070, 1031, 1012, 994; ESI-MS: expected, 370.0; observed, m/z 370.9 [M+H$^+$].

Determination of Regiochemistry of 2-methyl-3-cyanopyridine Products (6).

Condensation of chalcones with 3-aminocrotononitrile can yield, in theory, two different regioisomers of cyanopyridines. We used X-ray crystallography to determine the regioselectivity of cyanopyridine formation in solution and compared this to the macroarray product. Crystals of cyanopyridine 6Ae (synthesized in solution) were grown from acetone. X-ray crystallographic analyses of 6Ae revealed that the regioselectivity of cyanopyridine formation was consistent with the literature precedent (shown in FIG. 3).[ix] The alternate regioisomer of 6Ae was also synthesized using solution-phase procedures analogous to those described herein. HPLC traces of a sample of crystalline 6Ae and a sample of 6Ae obtained from the macroarray were identical (retention time=18.87 min), while the HPLC trace for the alternate regioisomer of 6Ae was different (retention time=19.97 min, FIG. 4). These data suggest that the regioselectivities of cyanopyridine formation on the macroarray and in solution are identical.[x]

Full Bacteriological Assay Protocols and Data.

Kirby-Bauer Disk Diffusion Assay.

Preparation of spots. Compound spots were subjected to the TFA cleavage conditions described above. The spots were next subjected to NH$_3$ vapor to neutralize any remaining TFA. A 100 mL portion of concentrated NH$_4$OH solution was poured into a 2.6 L Pyrex dish. Vials containing the spots (or intact macroarrays) were placed inside a small evaporating dish, and this was placed into the NH$_4$OH solution. The Pyrex dish was covered, and NH$_3$ vapor was allowed to slowly diffuse into the vials. After 1 h, the vials were removed from the NH$_3$ chamber, and the spots were allowed to stand open in a fume hood for at least 15 min to vent prior to analysis in the following assays. This afforded dry, paper disks containing adsorbed compound. Vancomycin susceptibility test disks (30 μg per disk) and methicillin susceptibility disks (10 μg per disk) were used as controls as received.

Representative assay procedure. A 400 μL portion of S. aureus overnight culture was diluted with 100 mL of sterile LB broth to give ca. 1.0×10$^6$ colony forming units (CFUs) per mL. A 200 μL portion of this suspension was added to Petri dishes containing non-selective agar, and spread homogeneously across the agar with a sterile cotton swab.

Up to four compound disks (prepared as described above) were placed gently onto the bed of agar equidistant from each other. (Note: either face of the disk could be placed on top of the agar, as the compound was distributed uniformly throughout the disk.) The Petri dishes were incubated at 37° C. for 18 h. The plates were removed, and the diameters of the zones of inhibition were measured in mm using a ruler (see FIG. 1A).

Macroarray Transfer Protocol.

A 69-member chalcone macroarray (3, 12 cm×18 cm) was subjected to the TFA cleavage and NH$_3$ neutralization conditions described above, except that the spots were not punched out of the array. The intact, cleaved, and dried macroarray was cut into six square sections (12 spots each), and a concentrated fluorescent dye solution[vi] in EtOAc was spotted (ca. 10 nL, using a glass capillary) in-between the compounds for later verification of macroarray transfer.

Untreated Whatman 3MM filter paper was cut into 6 cm×6 cm squares and arranged into a 2 cm high stack (30 squares) (shown schematically in FIG. 5). This stack was placed into a glass Petri dish (diameter=15 cm) containing 50 mL EtOH and allowed to soak up the solvent until saturated. A macroarray section was placed facedown on the stack, followed by four additional dry squares of Whatman 3MM. A flat aluminum block was placed on top of the stack and pressure (3 kg)

was applied for 90 sec. The four sheets were then removed from the stack, separated with tweezers, allowed to dry, and visualized with a UV lamp (Centela Mineralight Lamp UVGL-58 at 366 nm) to confirm compound transfer (FIG. 5). The fluorescent spots were marked with a #2 lead pencil and connected to form a grid. These macroarray copies were subjected to the TTC assay described in detail below. To prevent contamination in subsequent copies, the top two soaked sheets of the filter paper stack were removed after each transfer and replaced with fresh squares of EtOH-soaked filter paper.

This method gave a gradient of compound concentrations, with the last copy containing the most compound. The gradient was consistent across all locations on the array and for all compounds in the same structure class (FIG. 6). Other solvents ($CH_2Cl_2$, MeOH) and longer transfer times were examined; the methods described here were found to be optimal.

Agar Overlay TTC Screening Protocol.

Test tubes were filled with 15 mL of 0.8% (w/v) agar in LB, autoclaved, and stored in a 55° C. water bath until needed. For bacterial overlay, an appropriate volume of overnight culture was added to each test tube. The tube was gently vortexed, and the contents (15 mL) were quickly poured into a sterile, polystyrene Petri dish (diameter=9 cm). The dish was swirled to eliminate lingering air bubbles, and a 12-spot macroarray copy (described above) was gently slid into the solution. The dish was swirled to completely immerse the membrane in agar, and the agar was allowed to cool. The dish was incubated for 18 h at 37° C. Following incubation, the plates were "flooded" by the addition of 8 mL of 0.1% (w/v) TTC solution in LB and allowed to develop for ca. 1 h to visualize the zones of inhibition. Red zones above the macroarray copy indicated healthy cells, while white zones indicated that a compound on the macroarray copy had growth inhibitory activity against the strain of interest.

Initially, we performed our overlays according to the procedures published by Silen et al.[xii] However, we found that all of the compounds "hit" using this method, and we were unable to determine our best hits. To better resolve the relative activities of our compounds, the agar volume was increased from eight to 15 mL (example shown in FIG. 7).

Methicillin susceptibility test. We examined the susceptibility of our two S. aureus strains to methicillin using the agar overlay TTC assay. A susceptibility disk containing 10 µg of methicillin was placed in a Petri dish. Warm agar (0.8% in 15 mL LB) containing $10^6$ CFU/mL of either S. aureus 10390 (SA) or methicillin-resistant S. aureus 33591 (MRSA) was poured over the disk. The dishes were incubated at 37° C. for 18 h and visualized with TTC (shown below in FIG. 8).

Macroarray Overlay Data.

Estimated MIC Determination Protocol for Macroarray Compounds.

Preparation of spot samples and controls. An aliquot of DMSO (ca. 100 µL depending on the loading of the parent hydroxyacetophenone) was added to the dried compound residue obtained after TFA cleavage and elution from a single spot. This afforded a 2.0 mM "spot stock" solution for each spot. A small aliquot of each "spot stock" solution was saved for subsequent LC-MS analysis.

For the linezolid standard, 1.0 mL of acetonitrile was added to a single linezolid susceptibility test disk (30 µg per disk) in a 4 mL vial and vortexed for 15 min. The disk was removed, and the solution was concentrated under reduced pressure. The resulting residue was dissolved in 44 µL of DMSO to afford a 2.0 mM "spot stock" solution of linezolid.

Control "support" spots were punched from planar supports that had undergone all macroarray synthesis steps (tosy- lation, amination, linker attachment, cleavage, etc.) except for the loading of the initial hydroxyacetophenone building blocks (A-C). These samples allowed us to study the effects of the support background composition on bacterial growth. In addition, hydroxyacetophenone (A-C) derived spots that had undergone all macroarray synthesis steps except for the Claisen-Schmidt condensation were used as "parent" controls. These samples allowed us to determine the effects of minor impurities resulting from unreacted acetophenone reacting in subsequent steps. "Spot stock" solutions were generated from each of these spots as described above. In all cases studied, neither the support nor the parent control spots affected S. aureus growth.

For estimated MIC screens, 5.0 µL portions of the "spot stock" solutions were added to the appropriate wells in a sterile, polystyrene 96-well plate to yield ca. 50 µM solutions (dependent on the initial loading of hydroxyacetopheneone and compound purity). To the positive and negative control wells, 5.0 µL of DMSO were added (positive controls contained bacteria but no compound, while negative controls had neither compound nor bacteria). All estimated MIC assays were performed in quadruplicate. Note: the MIC value is defined as the lowest concentration where no bacterial growth occurs.

Representative estimated MIC assay procedure. This assay procedure is based in part on the method reported by Strøm et al.[xiii] A 400 µL portion of overnight S. aureus 10390 culture was diluted with 100 mL of sterile LB broth to give ca. $10^6$ CFUs per mL. Aliquots (195 µL) of this solution were added to all of the wells in a sterile 96-well plate (except for the negative control wells; 195 µL of sterile LB broth were added to these wells). The plates were placed on an orbital shaker table and gently swirled for 1 h to ensure compound dissolution, and then incubated (without shaking) for 12 h at 37° C. The absorbance at 595 nm was recorded using a plate reader. Compounds that demonstrated complete growth inhibition had an absorbance equal to that of the negative control (~0.045). The absorbance values for these compounds fall underneath the dotted line that depicts complete inhibition on the following charts. Compounds exhibiting no growth inhibition had an absorbance equal to that of the positive control (ca. 0.4).

Compounds that showed complete growth inhibition at ca. 50 µM were subjected to further testing. The original "spot stock" solutions of these compounds were diluted with DMSO to give ca. 25 and 13 µM final concentrations and tested for inhibitory activities using the procedure described above.

Estimated MIC Assay Data for Macroarray Compounds.

Error bars indicate average data over four assays.

Estimated MIC Assay Data for Active Macroarray Compounds (25 and 13 µM).

Inhibition Dose Response Curves for Active Compounds.

Dose response growth inhibition curves were determined for each active compound (resynthesized in solution) against S. aureus 10390 (SA) and methicillin-resistant S. aureus 33591 (MRSA). These data were obtained in an analogous manner to the estimated MIC determination procedure except, instead of using "spot stock" solutions, solutions of known concentrations were used, and the plates were placed in a shaker/incubator at 37° C. for the 12 h period. (Note, MIC values determined for lead compounds 4Bo, 4Bv, 6Al and 6Ao over 12 h were within error of those determined over 18 or 24 h.) The MICs of the known antibacterial agents, linezolid and ciprofloxacin, were also determined for comparison. MIC assays were performed in quadruplicate.

Bacterial Killing Curves for Compounds 4Bv, 6Ao, and 9Cf.

Solutions of compounds 4Bv, 6Ao, 9Cf, and linezolid were prepared in DMSO over a range of concentrations. Aliquots (50 μL) of these solutions were added to 2 mL of LB broth in test tubes to yield solutions with final concentrations equal to 0×, 0.5×, 1×, 2×, and 4× the compound's MIC against *S. aureus* 10390 (Note: MIC values for 4Bv, 6Ao, 9Cf, and linezolid were determined to be ca. 3.5, 7.5, 32.5, and 10.0, respectively). These test tubes were inoculated with ca. $10^6$ CFU/mL of *S. aureus* (at time=0 h) and placed in a 37° C. incubator. At 0, 2, 4, and 6 h time points, 20 L samples were withdrawn from the test tubes, diluted into 10 mL of LB broth in a test tube, and swabbed in duplicate on agar plates to determine CFUs. These plates were incubated at 37° C. for 24 h, after which time the colonies were counted visually. In the case of compound 6Ao, no dilutions were performed for the 1×, 2×, and 4× MIC samples at the 2, 4, and 6 h time points due to low cell populations. Instead, 200 μL was removed from the test tube and directly swabbed on the agar plates.

The cell populations of *S. aureus* samples treated with compounds 4Bv, 9Cf, and linezolid did not significantly diminish over a 6 h time period, even at concentrations as high as 4× the MIC. These compounds thus appear to be bacteriostatic at these concentrations. In contrast, compound 6Ao caused a rapid decrease in bacterial level as early as 2 h at concentrations equal to the MIC.[vii] We therefore describe this compound to be bactericidal over the concentration range tested.

Species Selectivity Studies.

Compound overlays. Active compounds from Table 3 were examined against other bacterial strains using agar overlay TTC assays (FIG. 14). Paper sections spotted with 30 nmol aliquots of compounds were overlaid with $10^6$ CFU/mL of various bacterial species in 15 mL of agar (0.8%), and incubated overnight. The plates were flooded with 8 mL of 0.1% TTC in LB to visualize the zones of growth inhibition as white spots.

Inhibition Dose Response Curves in *B. subtilis*, *S. epidermidis*, and *K. pneumoniae*.

Each compound from Table 3 was tested for inhibitory activity at 2.5, 5, 7.5, 10, 15, 20, 25, and 30 μM in the susceptible overlaid strains: *B. subtilis* ATCC 6633, *S. epidermidis* ATCC 12228, and *K. pneumoniae* ATCC 4352. MIC assays were run in quadruplicate as described above (with shaking).

Compound Characterization.

LC-MS Analysis of Representative Library Members Cleaved from Macroarrays.

LC-MS Analysis of Chalcones (4).

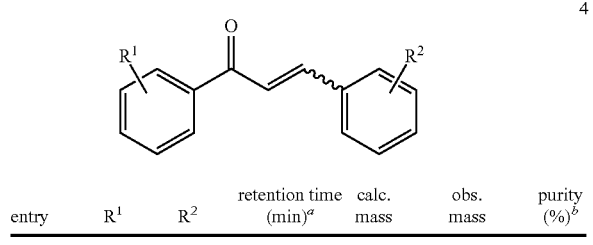

4

| entry | $R^1$ | $R^2$ | retention time (min)[a] | calc. mass | obs. mass | purity (%)[b] |
|---|---|---|---|---|---|---|
| 4Aa | 4-OH | H | 17.24/17.49 | 224.1 | 224.9 [M + H]⁺ | 77/12 |
| 4Ad | 4-OH | 4-F | 17.41/17.61 | 242.1 | 243.0 [M + H]⁺ | 71/17 |
| 4Ae | 4-OH | 3-Br | 18.02/18.41 | 302.0 | 302.8 [M + H]⁺ | 66/15 |
| 4Af | 4-OH | 4-Br | 18.08/18.50 | 302.0 | 302.8 [M + H]⁺ | 74/11 |
| 4Ag | 4-OH | 3-Cl | 17.83/18.25 | 258.0 | 258.9 [M + H]⁺ | 71/15 |
| 4Ah | 4-OH | 4-Cl | 17.94/18.27 | 258.0 | 258.9 [M + H]⁺ | 66/19 |

-continued

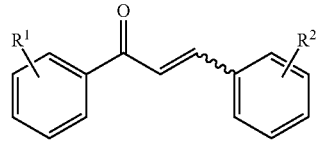

4

| entry | $R^1$ | $R^2$ | retention time (min)[a] | calc. mass | obs. mass | purity (%)[b] |
|---|---|---|---|---|---|---|
| 4Ai | 4-OH | 3-OMe | 17.24/17.46 | 254.1 | 254.9 [M + H]⁺ | 69/15 |
| 4Aj | 4-OH | 4-OMe | 17.24/17.30 | 254.1 | 254.9 [M + H]⁺ | 33/45 |
| 4Ak | 4-OH | 3-OCH₂O-4 | 17.15 | 268.1 | 268.9 [M + H]⁺ | 85 |
| 4Al | 4-OH | 2,3-Cl | 18.45/18.90 | 292.0 | 292.9 [M + H]⁺ | 18/64 |
| 4Am | 4-OH | 2-Br | 18.03/18.27 | 302.0 | 302.9 [M + H]⁺ | 27/72 |
| 4An | 4-OH | 3,4-Cl | 18.53/18.99 | 292.0 | 292.9 [M + H]⁺ | 21/46 |
| 4Ar | 4-OH | 3-Br, 4,5-OMe | 17.93/18.21 | 362.0 | 362.9 [M + H]⁺ | 11/51 |
| 4At | 4-OH | 2,4-Cl | 18.79/19.20 | 292.0 | 292.9 [M + M]⁺ | 75/19 |
| 4Av | 4-OH | 3,5-CF₃ | 18.79/19.12 | 360.1 | 360.9 [M + M]⁺ | 13/69 |

[a]Two retention times are given if the cis and trans isomer peaks were resolved in the HPLC trace.
[b]Determined by integration of HPLC traces (UV detection at 254 nm). Chalcones purity is reported as a mixture of cis and trans isomers. It is assumed that the major peak is the thermodynamically favored trans isomer.

LC-MS Analysis of Chalcones (4) (cont.)

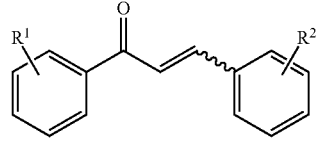

4

| entry | $R^1$ | $R^2$ | retention time (min)[a] | calc. mass | obs. mass | purity (%)[b] |
|---|---|---|---|---|---|---|
| 4Ba | 3-OH | H | 17.38/17.61 | 224.1 | 224.9 [M + H]⁺ | 33/54 |
| 4Bb | 3-OH | 2-F | 17.41/17.74 | 242.1 | 243.0 [M + H]⁺ | 25/66 |
| 4Bc | 3-OH | 3-F | 17.49/17.74 | 242.1 | 243.0 [M + H]⁺ | 29/58 |
| 4Be | 3-OH | 3-Br | 18.25/18.62 | 302.0 | 302.8 [M + H]⁺ | 18/70 |
| 4Bf | 3-OH | 4-Br | 18.30/18.68 | 302.0 | 302.9 [M + H]⁺ | 34/62 |
| 4Bg | 3-OH | 3-Cl | 18.09/18.43 | 258.0 | 258.9 [M + H]⁺ | 20/76 |
| 4Bh | 3-OH | 4-Cl | 18.14/18.48 | 258.0 | 258.9 [M + H]⁺ | 28/63 |
| 4Bj | 3-OH | 4-OMe | 17.52 | 254.1 | 254.9 [M + H]⁺ | 84 |
| 4Bl | 3-OH | 2,3-Cl | 18.62/19.04 | 292.0 | 292.9 [M + H]⁺ | 16/77 |
| 4Bm | 3-OH | 2-Br | 18.21/18.44 | 302.0 | 303.0 [M + H]⁺ | 18/81 |
| 4Bn | 3-OH | 3,4-Cl | 18.75/19.19 | 292.0 | 292.8 [M + H]⁺ | 23/47 |
| 4Bo | 3-OH | 2,3,6-Cl | 19.40 | 326.0 | 326.8 [M + H]⁺ | 91 |
| 4Bp | 3-OH | 2-N, 3-Br | 17.34/17.68 | 303.0 | 303.9 [M + H]⁺ | 11/83 |
| 4Bq | 3-OH | 3-Br, 4-OMe | 18.12 | 332.0 | 332.9 [M + H]⁺ | 96 |
| 4Bs | 3-OH | 2-OMe, 5-Br | 18.18/18.58 | 332.0 | 332.9 [M + H]⁺ | 22/75 |
| 4Bt | 3-OH | 2,4-Cl | 18.85/19.32 | 292.0 | 292.9 [M + H]⁺ | 21/72 |
| 4Bu | 3-OH | 3-CF₃ | 18.22/18.48 | 292.1 | 292.9 [M + H]⁺ | 13/75 |
| 4Bv | 3-OH | 3,5-CF₃ | 18.92/19.23 | 360.1 | 361.0 [M + H]⁺ | 13/75 |

[a]Two retention times are given if the cis and trans isomer peaks were resolved in the HPLC trace.
[b]Determined by integration of HPLC traces (UV detection at 254 nm). Chalcones purity is reported as a mixture of cis and trans isomers. It is assumed that the major peak is the thermodynamically favored trans isomer.

LC-MS Analysis of Chalcones (4) (cont.)

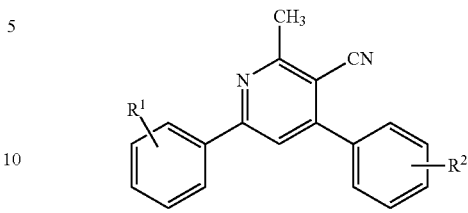

| entry | $R^1$ | $R^2$ | retention time (min)[a] | calc. mass | obs. mass | purity (%)[b] |
|---|---|---|---|---|---|---|
| 4Ca | 3-OMe, 4-OH | H | 17.32/17.66 | 254.1 | 254.9 [M + H]+ | 75/11 |
| 4Ce | 3-OMe, 4-OH | 3-Br | 18.16/18.61 | 332.0 | 332.8 [M + H]+ | 63/20 |
| 4Cf | 3-OMe, 4-OH | 4-Br | 18.22/18.69 | 332.0 | 332.8 [M + H]+ | 67/19 |
| 4Cg | 3-OMe, 4-OH | 3-Cl | 18.02/18.47 | 288.1 | 288.9 [M + H]+ | 68/21 |
| 4Ch | 3-OMe, 4-OH | 4-Cl | 18.05/18.53 | 288.1 | 288.9 [M + H]+ | 67/22 |
| 4Ci | 3-OMe, 4-OH | 3-OMe | 17.28/17.69 | 284.1 | 284.9 [M + H]+ | 77/12 |
| 4Cj | 3-OMe, 4-OH | 4-OMe | 17.32/17.44 | 284.1 | 284.9 [M + H]+ | 30/56 |
| 4Ck | 3-OMe, 4-OH | 3-OCH$_2$O-4 | 17.23/17.33 | 298.1 | 298.9 [M + H]+ | 10/82 |
| 4Cm | 3-OMe, 4-OH | 2-Br | 18.14/18.44 | 332.0 | 333.0 [M + H]+ | 64/11 |
| 4Cn | 3-OMe, 4-OH | 3,4-Cl | 18.70 | 322.0 | 322.9 [M + H]+ | 72 |
| 4Cq | 3-OMe, 4-OH | 3-Br, 4-OMe | 17.92/18.08 | 362.0 | 363.0 [M + H]+ | 46/44 |
| 4Cr | 3-OMe, 4-OH | 3-Br, 4,5-OMe | 18.08/18.42 | 392.0 | 392.9 [M + H]+ | 15/68 |
| 4Ct | 3-OMe, 4-OH | 2,4-Cl | 18.86/19.46 | 322.0 | 322.9 [M + H]+ | 22/67 |
| 4Cu | 3-OMe, 4-OH | 3-CF$_3$ | 18.01/18.14 | 322.1 | 323.0 [M + H]+ | 5/54 |
| 4Cv | 3-OMe, 4-OH | 3,5-CF$_3$ | 19.31 | 390.1 | 390.9 [M + H]+ | 72 |
| 4Cw | 3-OMe, 4-OH | 2-Cl | 18.02/18.33 | 288.0 | 288.9 [M + H]+ | 14/84 |

[a]Two retention times are given if the cis and trans isomer peaks were resolved in the HPLC trace.
[b]Determined by integration of HPLC traces (UV detection at 254 nm). Chalcones purity is reported as a mixture of cis and trans isomers. It is assumed that the major peak is the thermodynamically favored trans isomer.

LC-MS Analysis of 2-methyl-3-cyanopyridines (6).

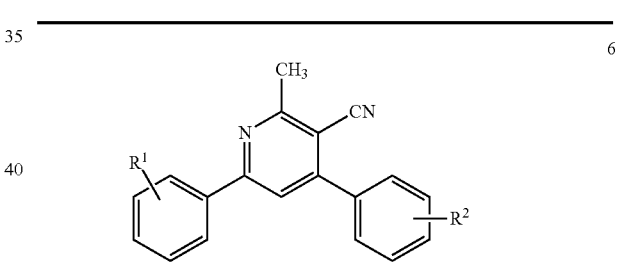

| entry | $R^1$ | $R^2$ | retention time (min) | calc. mass | obs. mass | purity (%)[a] |
|---|---|---|---|---|---|---|
| 6Aa | 4-OH | H | 18.06 | 286.1 | 286.9 [M + H]+ | 95 |
| 6Ab | 4-OH | 2-F | 18.06 | 304.1 | 304.9 [M + H]+ | 91 |
| 6Ac | 4-OH | 3-F | 18.24 | 304.1 | 304.9 [M + H]+ | 73 |
| 6Ad | 4-OH | 4-F | 18.19 | 304.1 | 304.9 [M + H]+ | 86 |
| 6Ae | 4-OH | 3-Br | 18.86 | 364.0 | 364.9 [M + H]+ | 81 |
| 6Af | 4-OH | 4-Br | 18.99 | 364.0 | 364.9 [M + H]+ | 90 |
| 6Ag | 4-OH | 3-Cl | 18.74 | 320.1 | 320.9 [M + H]+ | 90 |
| 6Ah | 4-OH | 4-Cl | 18.81 | 320.1 | 320.9 [M + H]+ | 87 |
| 6Ai | 4-OH | 3-OMe | 18.11 | 316.1 | 316.9 [M + H]+ | 96 |
| 6Aj | 4-OH | 4-OMe | 17.90 | 316.1 | 316.9 [M + H]+ | 91 |
| 6Al | 4-OH | 2,3-Cl | 18.78 | 354.0 | 354.9 [M + H]+ | 99 |
| 6Am | 4-OH | 2-Br | 18.30 | 364.0 | 364.9 [M + H]+ | 79 |
| 6Ao | 4-OH | 2,3,6-Cl | 19.08 | 388.0 | 389.0 [M + H]+ | 99 |
| 6At | 4-OH | 2,4-Cl | 19.05 | 354.0 | 354.9 [M + H]+ | 99 |
| 6Au | 4-OH | 3-CF$_3$ | 18.70 | 354.1 | 355.1 [M + H]+ | 65 |
| 6Av | 4-OH | 3,5-CF$_3$ | 19.33 | 422.1 | 423.0 [M + H]+ | 46 |
| 6Aw | 4-OH | 2-Cl | 18.22 | 320.1 | 320.9 [M + H]+ | 99 |

[a]Determined by integration of HPLC traces (UV detection at 254 nm).

LC-MS Analysis of 2-methyl-3-cyanopyridines (6) (cont.)

| entry | $R^1$ | $R^2$ | retention time (min) | calc. mass | obs. mass | purity (%)[a] |
|---|---|---|---|---|---|---|
| 6Ba | 3-OH | H | 18.21 | 286.1 | 286.9 [M + H]+ | 97 |
| 6Bb | 3-OH | 2-F | 18.14 | 304.1 | 304.9 [M + H]+ | 95 |
| 6Bd | 3-OH | 4-F | 18.33 | 304.1 | 304.9 [M + H]+ | 86 |
| 6Be | 3-OH | 3-Br | 18.96 | 364.0 | 364.9 [M + H]+ | 81 |
| 6Bg | 3-OH | 3-Cl | 18.82 | 320.1 | 320.9 [M + H]+ | 89 |
| 6Bj | 3-OH | 4-OMe | 18.13 | 316.1 | 316.9 [M + H]+ | 97 |
| 6Bk | 3-OH | 3-OCH$_2$O-4 | 18.00 | 330.1 | 331.0 [M + H]+ | 97 |
| 6Bl | 3-OH | 2,3-Cl | 18.86 | 354.0 | 354.9 [M + H]+ | 99 |
| 6Bn | 3-OH | 3,4-Cl | 19.38 | 354.0 | 354.9 [M + H]+ | 65 |
| 6Bo | 3-OH | 2,3,6-Cl | 19.14 | 388.0 | 388.9 [M + H]+ | 99 |
| 6Bp | 3-OH | 2-N, 3-Br | 18.10 | 365.0 | 365.9 [M + H]+ | 64 |
| 6Bq | 3-OH | 3-Br, 4-OMe | 18.65 | 394.0 | 394.9 [M + H]+ | 91 |
| 6Br | 3-OH | 3-Br, 4,5-OMe | 18.89 | 424.0 | 425.0 [M + H]+ | 67 |
| 6Bs | 3-OH | 2-OMe, 5-Br | 18.76 | 394.0 | 394.9 [M + H]+ | 92 |
| 6Bt | 3-OH | 2,4-Cl | 19.13 | 354.0 | 354.9 [M + H]+ | 99 |
| 6Bu | 3-OH | 3-CF$_3$ | 18.76 | 354.1 | 355.0 [M + H]+ | 78 |
| 6Bw | 3-OH | 2-Cl | 18.45 | 320.1 | 320.9 [M + H]+ | 97 |

[a]Determined by integration of HPLC traces (UV detection at 254 nm).

LC-MS Analysis of 2-methyl-3-cyanopyridines (6) (cont.)

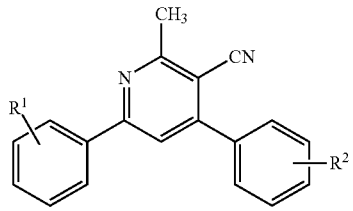

| entry | R¹ | R² | retention time (min) | calc. mass | obs. mass | purity (%)[b] |
|---|---|---|---|---|---|---|
| 6Ca | 3-OMe, 4-OH | H | 18.22 | 316.1 | 316.9 [M + H]⁺ | 89 |
| 6Cb | 3-OMe, 4-OH | 2-F | 18.18 | 334.1 | 334.9 [M + H]⁺ | 94 |
| 6Cc | 3-OMe, 4-OH | 3-F | 18.39 | 334.1 | 334.9 [M + H]⁺ | 75 |
| 6Cd | 3-OMe, 4-OH | 4-F | 18.35 | 334.1 | 334.9 [M + H]⁺ | 85 |
| 6Ce | 3-OMe, 4-OH | 3-Br | 19.11 | 394.1 | 394.9 [M + H]⁺ | 93 |
| 6Cf | 3-OMe, 4-OH | 4-Br | 19.02 | 394.1 | 394.9 [M + H]⁺ | 78 |
| 6Ch | 3-OMe, 4-OH | 4-Cl | 18.98 | 350.1 | 350.9 [M + H]⁺ | 72 |
| 6Ci | 3-OMe, 4-OH | 3-OMe | 18.26 | 346.1 | 346.9 [M + H]⁺ | 92 |
| 6Cl | 3-OMe, 4-OH | 2,3-Cl | 19.02 | 384.0 | 385.0 [M + H]⁺ | 91 |
| 6Cm | 3-OMe, 4-OH | 2-Br | 18.53 | 394.0 | 395.0 [M + H]⁺ | 91 |
| 6Cn | 3-OMe, 4-OH | 3,4-Cl | 19.62 | 384.0 | 384.9 [M + H]⁺ | 62 |
| 6Ct | 3-OMe, 4-OH | 2,4-Cl | 19.26 | 384.0 | 385.0 [M + H]⁺ | 89 |
| 6Cu | 3-OMe, 4-OH | 3-CF₃ | 18.92 | 384.1 | 385.1 [M + H]⁺ | 64 |
| 6Cv | 3-OMe, 4-OH | 3,5-CF₃ | 19.57 | 452.1 | 453.1 [M + H]⁺ | 47 |
| 6Cw | 3-OMe, 4-OH | 2-Cl | 18.48 | 350.1 | 351.0 [M + H]⁺ | 98 |

[a]Determined by integration of HPLC traces (UV detection at 254 nm).

LC-MS Analysis of methylpyrimidines (9).

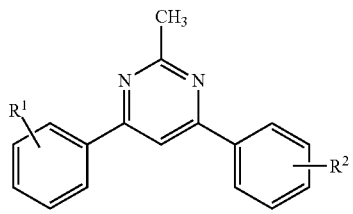

| entry | R¹ | R² | retention time (min) | calc. mass | obs. mass | purity (%)[a] |
|---|---|---|---|---|---|---|
| 9Aa | 4-OH | H | 16.48 | 262.1 | 262.9 [M + H]⁺ | 77 |
| 9Ab | 4-OH | 2-F | 16.88 | 280.1 | 280.9 [M + H]⁺ | 75 |
| 9Ac | 4-OH | 3-F | 17.39 | 280.1 | 281.0 [M + H]⁺ | 89 |
| 9Ae | 4-OH | 3-Br | 18.30 | 340.0 | 340.9 [M + H]⁺ | 87 |
| 9Ag | 4-OH | 3-Cl | 18.15 | 296.1 | 296.8 [M + H]⁺ | 64 |
| 9Ai | 4-OH | 3-OMe | 16.51 | 292.1 | 292.9 [M + H]⁺ | 91 |
| 9Aj | 4-OH | 4-OMe | 16.07 | 292.1 | 292.9 [M + H]⁺ | 75 |
| 9Bb | 3-OH | 2-F | 17.78 | 280.1 | 280.9 [M + H]⁺ | 80 |
| 9Bd | 3-OH | 4-F | 17.71 | 280.1 | 280.9 [M + H]⁺ | 72 |
| 9Be | 3-OH | 3-Br | 19.11 | 340.0 | 340.8 [M + H]⁺ | 84 |
| 9Bf | 3-OH | 4-Br | 19.00 | 340.0 | 340.8 [M + H]⁺ | 86 |
| 9Bg | 3-OH | 3-Cl | 18.92 | 296.1 | 296.9 [M + H]⁺ | 82 |
| 9Bh | 3-OH | 4-Cl | 18.75 | 296.1 | 296.9 [M + H]⁺ | 80 |
| 9Bi | 3-OH | 3-OMe | 17.35 | 292.1 | 292.9 [M + H]⁺ | 80 |
| 9Ca | 3-OMe, 4-OH | H | 16.34 | 292.1 | 293.0 [M + H]⁺ | 85 |
| 9Cc | 3-OMe, 4-OH | 3-F | 17.58 | 310.1 | 311.0 [M + H]⁺ | 61 |
| 9Cd | 3-OMe, 4-OH | 4-F | 17.00 | 310.1 | 310.9 [M + H]⁺ | 85 |
| 9Cf | 3-OMe, 4-OH | 4-Br | 18.29 | 370.0 | 370.8 [M + H]⁺ | 86 |
| 9Cg | 3-OMe, 4-OH | 3-Cl | 18.36 | 326.1 | 326.9 [M + H]⁺ | 91 |
| 9Ch | 3-OMe, 4-OH | 4-Cl | 18.04 | 326.1 | 326.9 [M + H]⁺ | 82 |
| 9Cj | 3-OMe, 4-OH | 4-OMe | 16.16 | 322.1 | 323.0 [M + H]⁺ | 84 |

[a]Determined by integration of HPLC traces (UV detection at 254 nm).

LC-MS Analysis of aminopyrimidines (10).

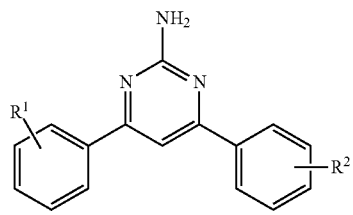

| entry | R¹ | R² | retention time (min) | calc. mass | obs. mass | purity (%)[a] |
|---|---|---|---|---|---|---|
| 10Aa | 4-OH | H | 15.43 | 263.1 | 263.9 [M + H]⁺ | 81 |
| 10Ac | 4-OH | 3-F | 15.67 | 281.1 | 281.9 [M + H]⁺ | 85 |
| 10Ad | 4-OH | 4-F | 15.73 | 281.1 | 282.0 [M + H]⁺ | 90 |
| 10Ae | 4-OH | 3-Br | 16.21 | 341.0 | 341.8 [M + H]⁺ | 70 |
| 10Af | 4-OH | 4-Br | 16.26 | 341.0 | 341.8 [M + H]⁺ | 27 |
| 10Ag | 4-OH | 3-Cl | 16.12 | 297.1 | 297.9 [M + H]⁺ | 85 |
| 10Ah | 4-OH | 4-Cl | 18.02 | 297.1 | 297.9 [M + H]⁺ | 69 |
| 10Ba | 3-OH | H | 15.54 | 263.1 | 263.9 [M + H]⁺ | 70 |
| 10Bb | 3-OH | 2-F | 15.74 | 281.1 | 282.0 [M + H]⁺ | 55 |
| 10Bc | 3-OH | 3-F | 15.98 | 281.1 | 282.0 [M + H]⁺ | 64 |
| 10Bd | 3-OH | 4-F | 15.85 | 281.1 | 282.0 [M + H]⁺ | 73 |
| 10Be | 3-OH | 3-Br | 16.51 | 341.0 | 341.8 [M + H]⁺ | 82 |
| 10Bg | 3-OH | 3-Cl | 16.37 | 297.1 | 297.9 [M + H]⁺ | 94 |
| 10Bh | 3-OH | 4-Cl | 16.35 | 297.1 | 297.8 [M + H]⁺ | 94 |
| 10Ca | 3-OMe, 4-OH | H | 15.50 | 293.1 | 293.9 [M + H]⁺ | 83 |
| 10Cb | 3-OMe, 4-OH | 2-F | 15.54 | 311.1 | 312.0 [M + H]⁺ | 74 |
| 10Ce | 3-OMe, 4-OH | 3-Br | 16.32 | 371.0 | 371.5 [M + H]⁺ | 85 |
| 10Cf | 3-OMe, 4-OH | 4-Br | 16.32 | 371.0 | 371.8 [M + H]⁺ | 32 |
| 10Cg | 3-OMe, 4-OH | 3-Cl | 16.21 | 327.1 | 327.9 [M + H]⁺ | 89 |
| 10Ch | 3-OMe, 4-OH | 4-Cl | 16.18 | 327.1 | 327.9 [M + H]⁺ | 88 |

[a]Determined by integration of HPLC traces (UV detection at 254 nm).

HPLC Traces of Active Compounds Cleaved from Macroarrays.

UV detection at 254 nm. The main peaks were identified as the desired products (by ESI-MS). An asterisk denotes the minor stereoisomer for chalcones 4At, 4Be, 4Bl, 4Bo, 4Bv, and 4Cf.

1.f. References

1. Walsh, C. T. (2003). Where will new antibiotics come from? Nat. Rev. Microbiol. 1, 65-70.
2. US Center for Disease Control (CDC). See: www.cdc.gov/drugresistance.
3. Grundmann, H., Aires-de-Sousa, M., Boyce, J., and Tiemersma, E. (2006). Emergence and resurgence of methicillin-resistant *Staphylococcus aureus* as a public-health threat. Lancet 368, 874-885.
4. Walsh, C. T. (2003). Antibiotics: Actions, Origins, Resistance (Washington, DC: ASM Press).
5. Hilpert, K., Elliott, M. R., Volkmer-Engert, R., Henklein, P., Donini, O., Zhou, Q., Winkler, D. F. H., and Hancock, R. E. W. (2006). Sequence requirements and an optimization strategy for short antimicrobial peptides. Chem. Biol. 13, 1101-1107.
6. Wyatt, E. E., Fergus, S., Galloway, W. R. J. D., Bender, A., Fox, D. J., Plowright, A. T., Jessiman, A. S., Welch, M., and Spring, D. R. (2006). Skeletal diversity construction via a branching synthetic strategy. Chem. Commun., 3296-3298.
7. Nicolaou, K. C., Roecker, A. J., Barluenga, S., Pfefferkorn, J. A., and Cao, G.-Q. (2001). Discovery of novel antibacterial agents active against methicillin-resistant *Staphylococcus aureus* from combinatorial benzopyran libraries. ChemBioChem 2, 460-465.

8. Blackwell, H. E. (2006). Hitting the SPOT: Small molecule macroarrays advance combinatorial synthesis. Curr. Opin. Chem. Biol. 10, 203-212.
9. Lin, Q., and Blackwell, H. E. (2006). Rapid synthesis of diketopiperazine macroarrays via Ugi four-component reactions on planar solid supports. Chem. Commun., 2884-2886.
10. Bowman, M. D., Jacobson, M. M., and Blackwell, H. E. (2006). Discovery of fluorescent cyanopyridine and deazalumazine dyes using small molecule macroarrays. Org. Lett. 8, 1645-1648.
11. Bowman, M. D., Jacobson, M. M., Pujanauski, B. G., and Blackwell, H. E. (2006). Efficient synthesis of small molecule macroarrays: optimization of the macroarray synthesis platform and examination of microwave and conventional heating methods. Tetrahedron 62, 4715-4727.
12. Lin, Q., O'Neill, J. C., and Blackwell, H. E. (2005). Small molecule macroarray construction via Ugi four-component reactions. Org. Lett. 7, 4455-4458.
13. Nielsen, S. F., Larsen, M., Boesen, T., Schonning, K., and Kromann, H. (2005). Cationic chalcone antibiotics. design, synthesis, and mechanism of action. J. Med. Chem. 48, 2667-2677.
14. Nielsen, S. F., Boesen, T., Larsen, M., Schonning, K., and Kromann, H. (2004). Antibacterial chalcones—bioisosteric replacement of the 4'-hydroxy group. Bioorg. Med. Chem. 12, 3047-3054.
15. Abdel-Aziz, A. A., El-Subbagh, H. I., and Kunieda, T. (2005). Lewis acid-promoted transformation of 2-alkoxypyridines into 2-aminopyridines and their antibacterial activity. Part 2: Remarkably facile C-N bond formation. Bioorg. Med. Chem. 13, 4929-4935.
16. Rajvaidya, S., Vasavada, J., and Parekh, H. H. (2004). Synthesis and microbiological activities of some pyrazolines and cyanopyridines. Indian J. Chem. 438, 906-908.
17. Powers, D. G., Casebier, D. S., Fokas, D., Ryan, W. J., Troth, J. R., and Coffen, D. L. (1998). Automated parallel synthesis of chalcone-based screening libraries. Tetrahedron 54, 4085-4096.
18. Marron, B. E., and Jayawickreme, C. K. (2003). Going to the well no more: lawn format assays for ultra-high-throughput screening. Curr. Opin. Chem. Biol. 7, 395-401, and references therein.
19. Ni, L., Meng, C. Q., and Sikorski, J. A. (2004). Recent advances in therapeutic chalcones. Expert Opin. Ther. Patents 14, 1669-1691.
(i) For further information about this commercial MW reactor system, see: http://www.milestonesci.com/index2.php
(ii) Bowman, M. D.; Jacobson, M. M.; Pujanauski, B. G.; Blackwell, H. E. Tetrahedron 2006, 62, 4715-4727.
(iii) Ast, T.; Heine, N.; Germeroth, L.; Schneider-Mergener, J.; Wenschuh, H. Tetrahedron Lett. 1999, 40, 4317-4318.
(iv) Carpino, L. A.; Han, G. Y. J. Org. Chem. 1972, 37, 3404-3409.
(v) Chalcones derived from benzaldehyde building blocks k-w gave substantial quantities of dehalogenated by-products in methylpyrimidine (7) and aminopyrimidine (8) syntheses, and thus were not utilized for final macroarray construction.
(vi) Submersion of the chalcone macroarray in the acetamidine or guanidine solutions under air gave full conversion to the pyrimidine products, as opposed to dihydropyrimidines. We previously showed that applying the reagent solution in a spotting format to chalcone arrays gave the latter products. See: Bowman, M. D., Jeske, R. C., and Blackwell, H. E. Org. Lett. 2004, 6, 2019-2022.
(vii) Nielsen, S. F.; Boesen, T.; Larsen, M.; Schønning, K.; Kromann, H. Bioorg. Med. Chem. 2004, 12, 3047-3054.
(viii) Bruce, J. M.; Creed, D.; Dawes, K. J. Chem. Soc. (C) 1971, 12, 2244-2252.
(ix) Matsui, M.; Oji, A.; Hiramatsu, K. Shibata, K.; Muramatsu, H. J. Chem. Soc., Perkin Trans. 2 1992, 201-206.
(x) Full X-ray crystallographic data for cyanopyridine 6Ae have been deposited at the
Cambridge Crystallographic Data Centre (CCDC #297730). These data can be obtained free of charge from the CCDC via: http://www.ccdc.cam.ac.uk/products/csd/request/(xi)
(xi) The fluorescent dye used was 4,6-bis(4-methoxyphenyl)-2-methyl-3-cyanopyridine ($\phi_{rel}$=0.77, $\lambda_{ex}$=335, $\lambda_{em}$=409). A supersaturated solution of the dye was prepared in EtOAc (0.05 M) and kept warm to minimize precipitation. A microcapillary tube was used to create a fluorescent spot (1 mm diameter) between macroarray members. For details of the synthesis and spectral characterization of this compound, see: Bowman, M. D., Jacobson, M. M.; Blackwell, H. E. Org. Lett. 2006, 8, 1645-1648.
(xii) Silen, J. L.; Lu, A. T.; Solas, D. W.; Gore, M. A.; Maclean, D.; Shah, N. H.; Coffin, J. M.; Bhinderwala, N. S.; Wang, Y.; Tsutsui, K. T.; Look, G. C.; Campbell D. A.; Hale, R. L.; Navre, M.; DeLuca-Flaherty, C. R. Antimicrob. Agents Chem. 1998, 42, 1447-1453.
(xiii) Strøm, M. B.; Haug, E. B.; Skar, M. L; Stensen, W.; Stiberg, T.; Svendsen, J. S. J. Med. Chem. 2003, 46, 1567-1570.

EXAMPLE 2

Chalcones, Cyanopyridines, Methylpyrimidines and Aminopyrimidines Useful as Antibacterial Agents The present invention generally provides antibacterial compounds and methods related to use of these antibacterial compounds. The compounds of the invention include chalcones, cyanopyridines, methylpyrimidines and aminopyrimidines, which are useful as antibacterial agents. These compounds may be synthesized and screened using macroarrays. In one exemplary embodiment, the present invention provides compounds having the Formula, I, II and III, as shown below:

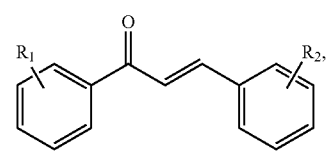

I

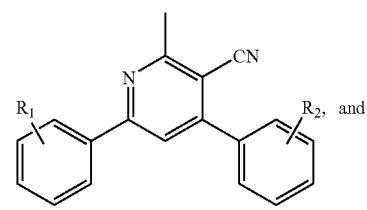

II

-continued
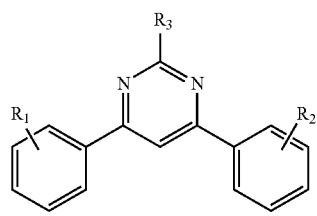
wherein
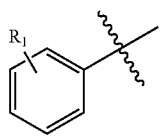
is selected from the group consisting of
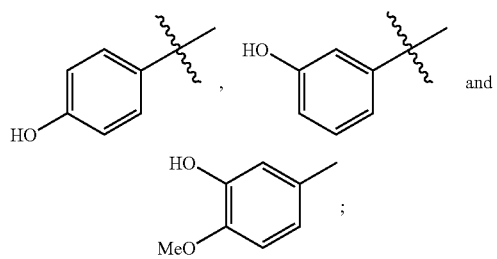
wherein
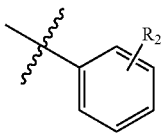
is selected from the group consisting of:
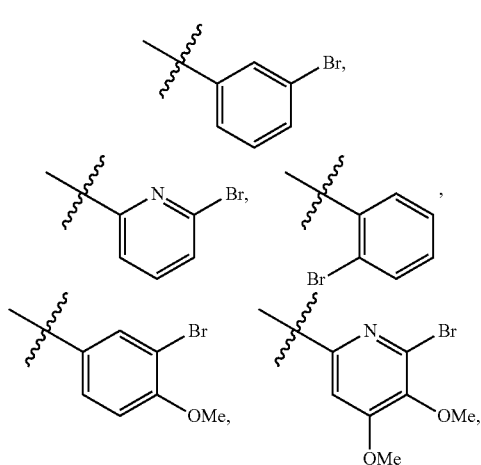
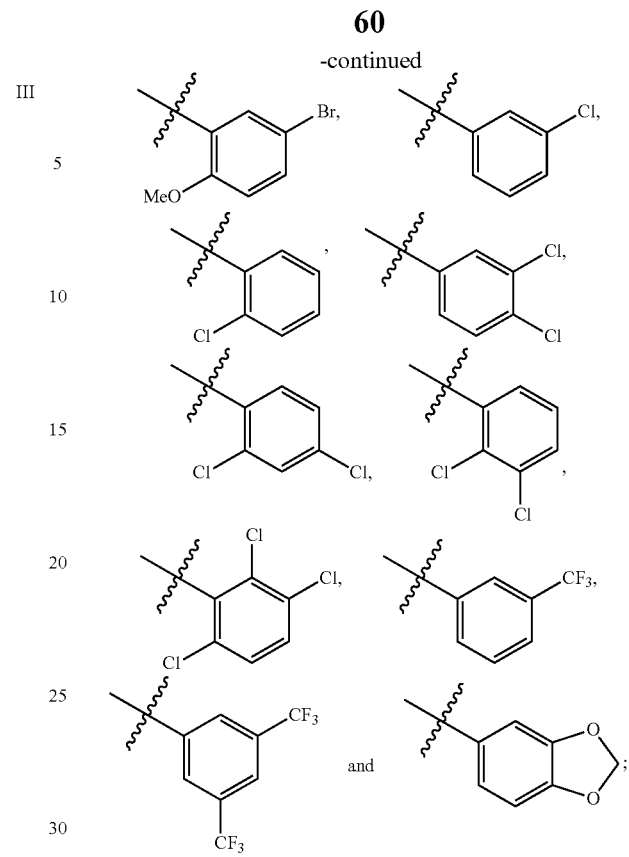
and wherein $R_3$ is $CH_3$ or $NH_2$.
In an preferred embodiment, the invention provides the following compounds, having the formula:
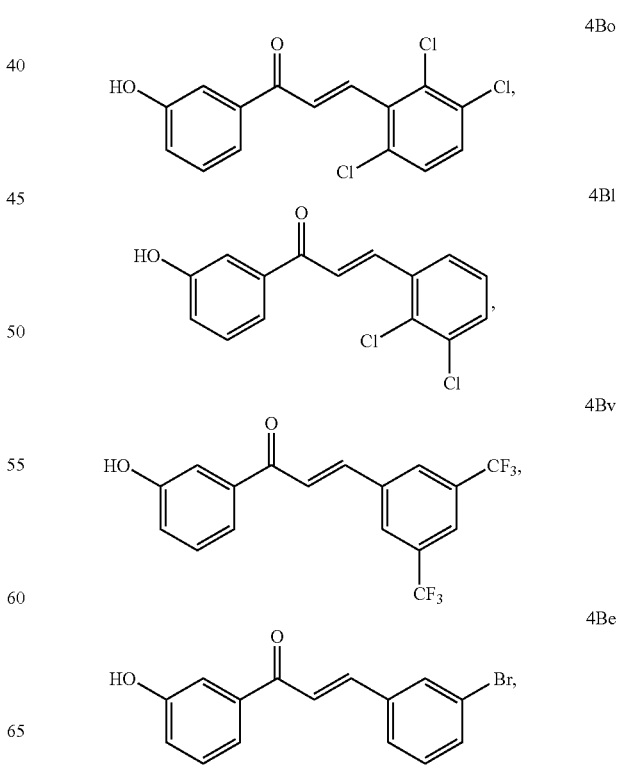

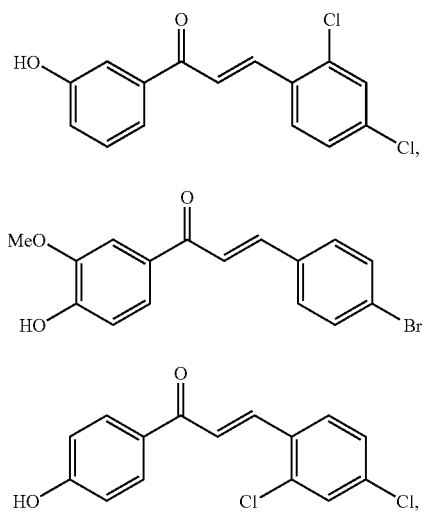
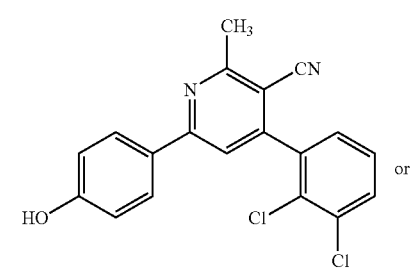
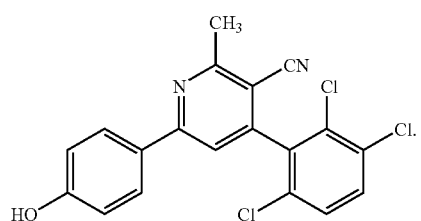
The invention also provides a method of use of a compound as an antibacterial agent, wherein the compound has a formula selected from the group consisting of:
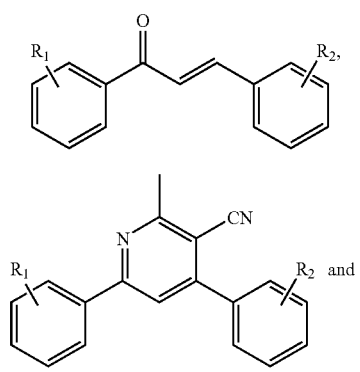
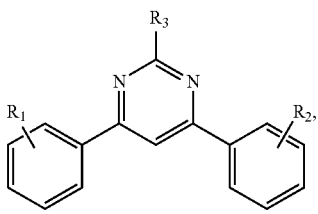
wherein
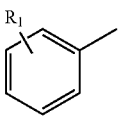
is independently selected from the group consisting of
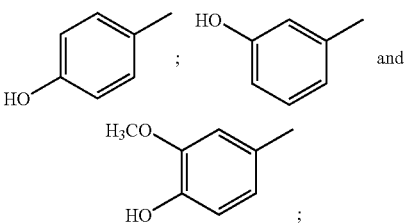
wherein
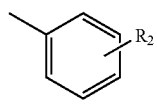
is independently selected from the group consisting of:
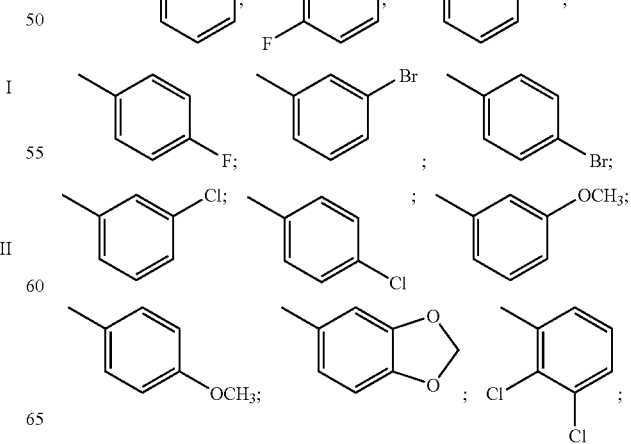

-continued

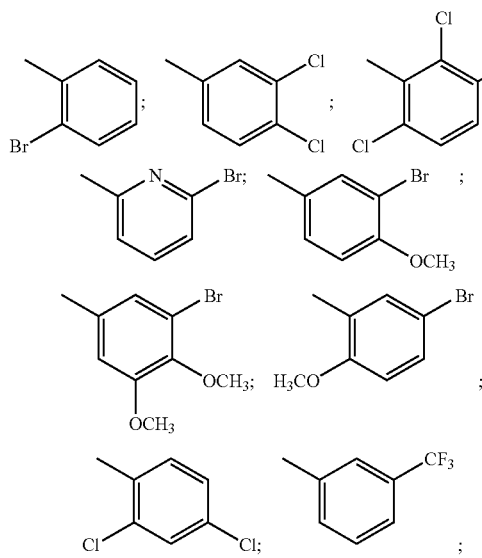

and wherein R₃ is independently selected from the group consisting of CH₃ and NH₂.

EXAMPLE 3

Methods of Screening Compounds for Antibacterial Activity

The invention also provides a method of screening a compound for antibacterial activity. This method comprises the steps: (a) constructing a macroarray of the compound, wherein the macroarray comprises a first platform, a linker coupled to the first platform and the compound coupled to the linker; and (b) incubating the macroarray with a bacterial culture, whereby compounds having antibacterial activity exhibit a zone of inhibition.

In this method, the first platform is independently selected from the group consisting of cellulose, Teflon, glass and silicone. Other substrate known to one of ordinary skill in the art may be used for use as a platform in using similar methodology described here. Also as described above, in this method, the wherein the compound has a formula selected from the group consisting of:

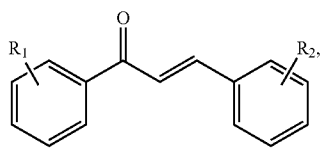

-continued

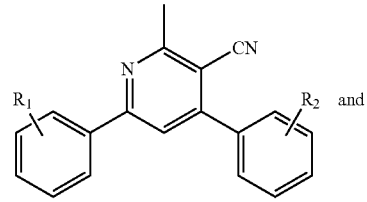

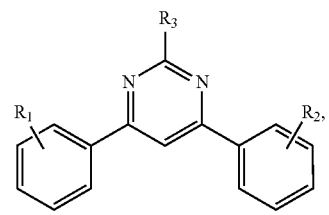

wherein

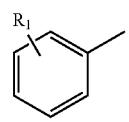

is independently selected from the group consisting of

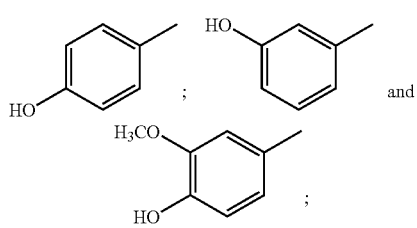

wherein

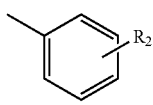

is independently selected from the group consisting of:

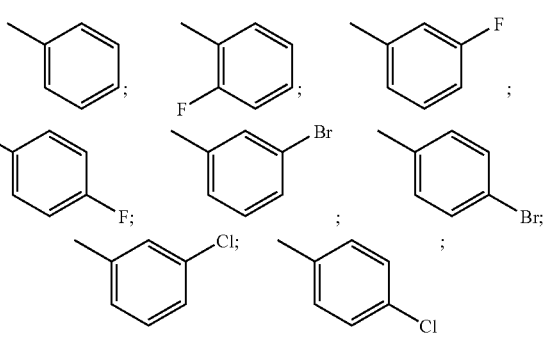

-continued

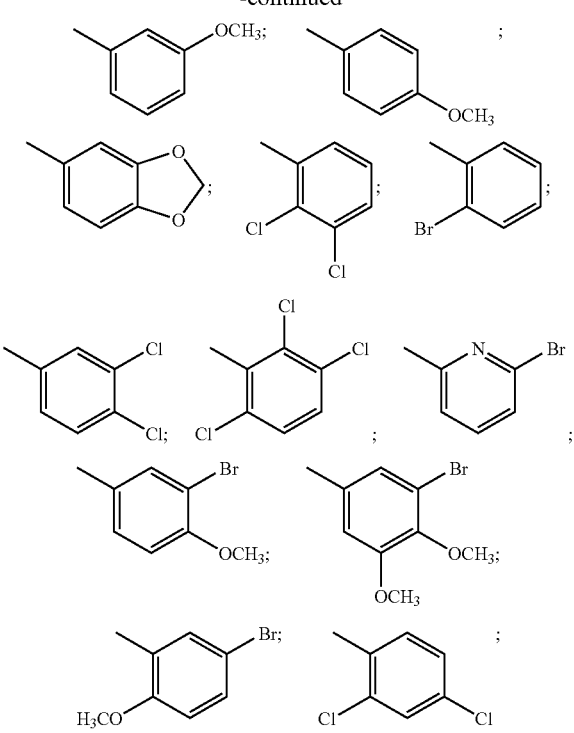

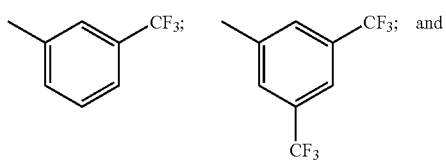

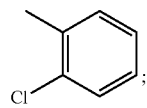

and wherein R₃ is independently selected from the group consisting of CH₃ and NH₂. Preferably in this method, the linker is acid cleavable or photo cleavable, such as a Wang-type linker. In yet another preferable exemplary embodiment, the bacterial culture is *S. aureus*.

The present invention also provides a method of screening a compound for antibacterial activity. This method comprises the steps: (a) constructing a macroarray of the compound, wherein the macroarray comprises a first platform, a linker coupled to the first platform and the compound coupled to the linker; (b) copying the macroarray to a second platform; (c) incubating the macroarray or the copy of the macroarray with a bacterial culture; and (d) contacting the macroarray or the copy of the macroarray having the bacterial culture with a visualization agent, whereby the visualization agent is capable of differentiating between a zone of inhibition caused by the bacterial culture and zone of no activity. Also, as described above, the first or the second platform is independently selected from the group consisting of cellulose, Teflon, glass and silicone. Of course, other platforms may also be used to achieve similar results.

Further, as described above, the wherein the compound has a formula selected from the group consisting of:

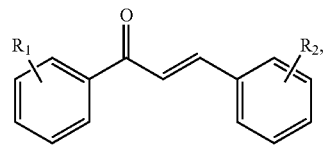
I

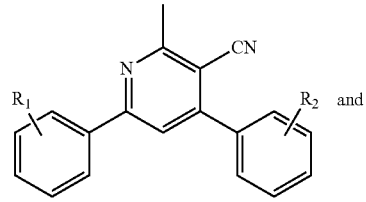
II

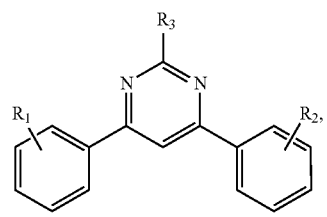
III wherein

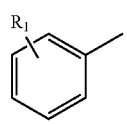

is independently selected from the group consisting of

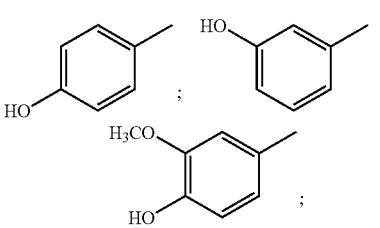

wherein

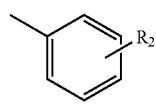

is independently selected from the group consisting of:

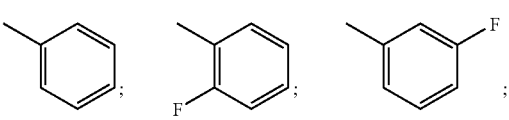

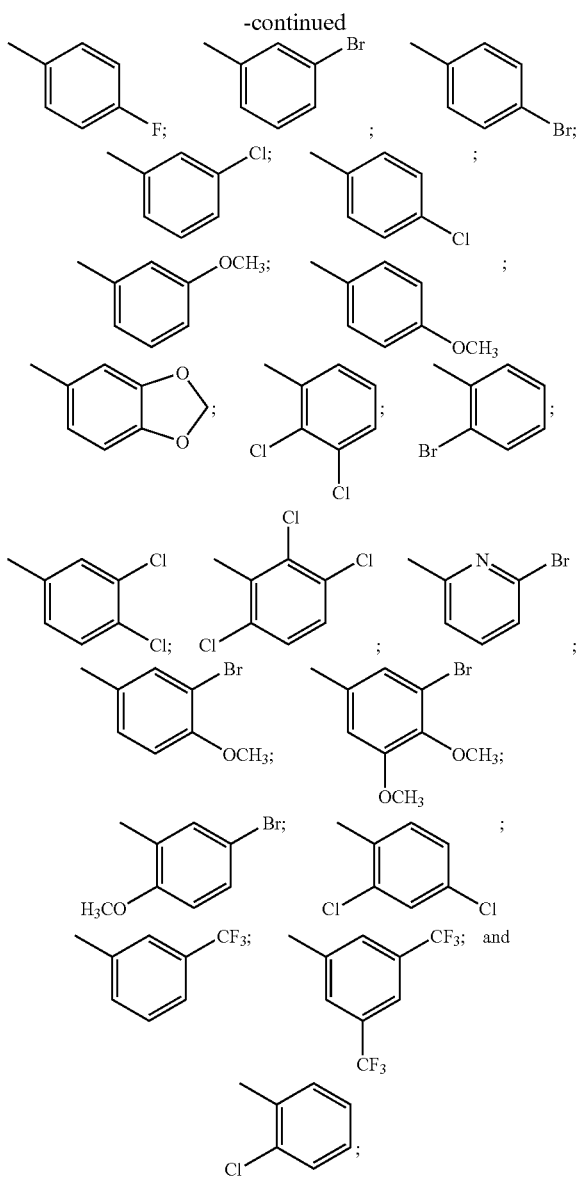

and wherein R$_3$ is independently selected from the group consisting of CH$_3$ and NH$_2$.

Further, in this method, the linker is acid cleavable or photo cleavable, such as a Wang-type linker. Also, most preferably, in this method, the bacterial culture includes *S. aureus*. In a preferable embodiment, the visualization agent is triphenyl tetrazolium chloride (TTC), although other visualization agents known to one of ordinary skill in the art be used in lieu of TTC to achieve similar results.

Statements Regarding Incorporation by Reference and Variations

U.S. Provisional Application No. 60/747,628 entitled "Antibacterial Agents Using Small Molecule Macroarrays" filed on May 18, 2007 is hereby incorporated by reference in its entirety to the extent not inconsistent with the present description.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Many of the molecules disclosed herein contain one or more ionizable groups [groups from which a proton can be removed (e.g., —COON) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Methods of this invention comprise the step of administering a "therapeutically effective amount" of the present therapeutic formulations containing the present compounds, to treat, reduce or regulate a disease state in a patient, including a disease state involving one or more infectious agents such as bacteria. The term "therapeutically effective amount," as used herein, refers to the amount of the therapeutic formulation, that, when administered to the individual is effective to treat, reduce or regulate a disease state in a patient, including a disease state involving one or more infectious agents such as bacteria. As is understood in the art, the therapeutically effective amount of a given compound or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound can be determined as is understood in the art.

Any suitable form of administration can be employed in connection with the therapeutic formulations of the present invention. The therapeutic formulations of this invention can be administered intravenously, in oral dosage forms, intraperitoneally, subcutaneously, or intramuscularly, all using dosage forms well known to those of ordinary skill in the pharmaceutical arts.

The therapeutic formulations of this invention can be administered alone, but may be administered with a pharmaceutical carrier selected upon the basis of the chosen route of administration and standard pharmaceutical practice.

The therapeutic formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

We claim:
1. A compound having the formula:

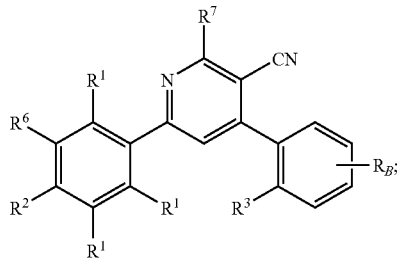

(FX35)

wherein

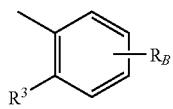

is selected from the group consisting of:

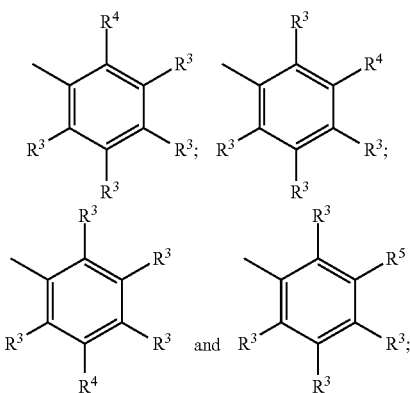

or a pharmaceutically acceptable salt thereof;
wherein each $R^1$ is independently selected from the group consisting of a hydrogen, and an unsubstituted $C_1$-$C_6$ alkyl group;
wherein $R^2$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$;
wherein $R^6$ is selected from the group consisting of —H, —$CH_3$, —$CH_2CH_3$, —$CH_2CH_2CH_3$, —$CH_2CH_2CH_2CH_3$, —$CH_2CH_2CH_2CH_2CH_3$, —OH, —$OCH_3$, —$OCH_2CH_3$, —$OCH_2CH_2CH_3$, —$OCH_2CH_2CH_2CH_3$ and —$OCH_2CH_2CH_2CH_2CH_3$;
and wherein at least one of $R^2$ and $R^6$ is —OH, —$OCH_3$, —$OCH_2CH_3$, —$OCH_2CH_2CH_3$, —$OCH_2CH_2CH_2CH_3$ or —$OCH_2CH_2CH_2CH_2CH_3$;
wherein each $R^3$ is independently selected from the group consisting of a hydrogen, a halogen, an unsubstituted amine group, an unsubstituted $C_1$-$C_8$ alkyl group, an unsubstituted $C_1$-$C_8$ alkoxyl group, a $C_1$-$C_3$ haloalkyl group, a hydroxyl group, a —CN group, an azide group, and a —$NO_2$ group;
wherein $R^4$ is selected from the group consisting of —F, —Cl, —Br, and —I;
wherein $R^5$ is selected from the group consisting of —$CF_3$, —$CF_2CF_3$, —$CF_2CF_2CF_3$, —$CF_2CF_2CF_2CF_3$, and —$CF_2CF_2CF_2CF_2CF_2CF_3$;
wherein $R^7$ is an unsubstituted $C_1$-$C_8$ alkyl group.

2. A compound of claim 1 having a formula selected from the group consisting of:

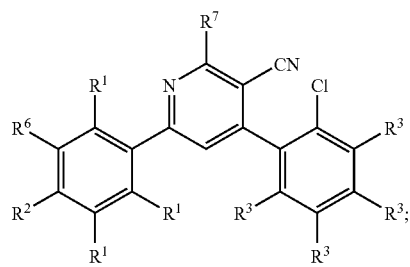

(FX36)

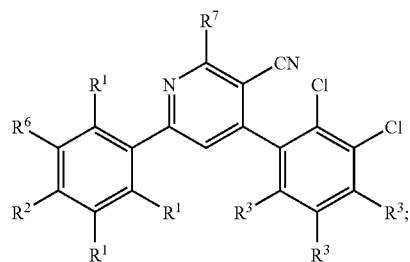

(FX37)

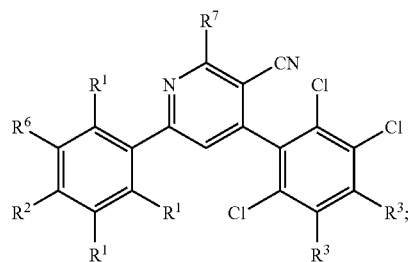

(FX38)

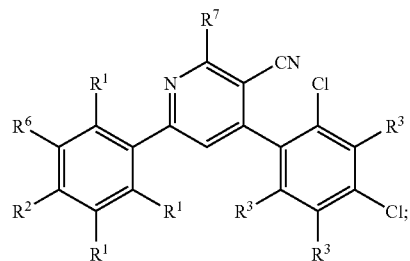

(FX39)

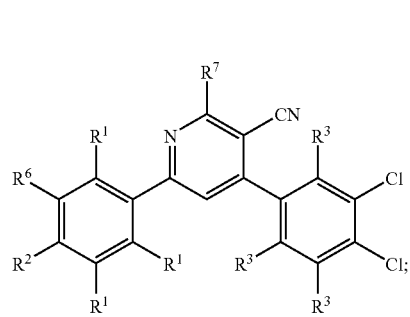

(FX40)

-continued (FX41)
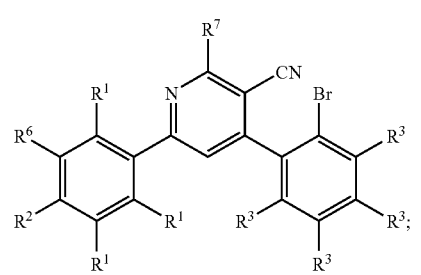

(FX42)
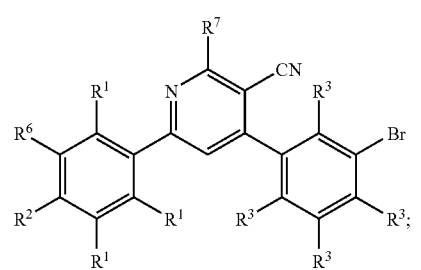

(FX43)
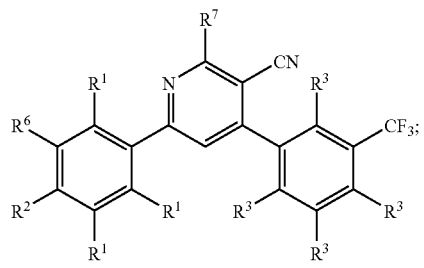

(FX44)
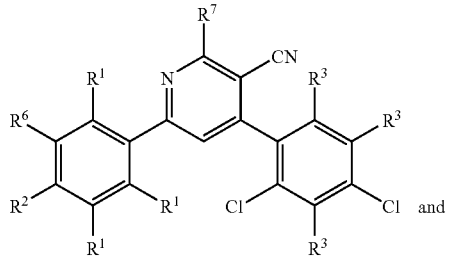
and (FX45)
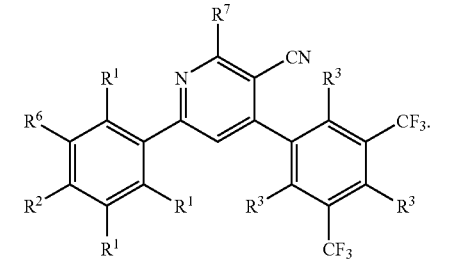

3. A compound of claim 2:
wherein each $R^1$ is independently selected from the group consisting of —H, —CH$_3$, —CH$_2$CH$_3$, —CH$_2$CH$_2$CH$_3$ and —CH$_2$CH$_2$CH$_2$CH$_3$;
wherein each $R^3$ is independently selected from the group consisting of —H, —F, —Cl, —Br, —I, —CF$_3$, —CF$_2$CF$_3$, —CF$_2$CF$_2$CF$_3$, —CH$_3$, —CH$_2$CH$_3$, —CH$_2$CH$_2$CH$_3$, —CH$_2$CH$_2$CH$_2$CH$_3$, —OH, —OCH$_3$, —OCH$_2$CH$_3$ and —OCH$_2$CH$_2$CH$_2$CH$_3$; and
wherein $R^7$ is selected from the group consisting of —CH$_3$, —CH$_2$CH$_3$, —CH$_2$CH$_2$CH$_3$, and —CH$_2$CH$_2$CH$_2$CH$_3$.

4. A compound of claim 1 having a formula selected from the group consisting of:

(FX46)
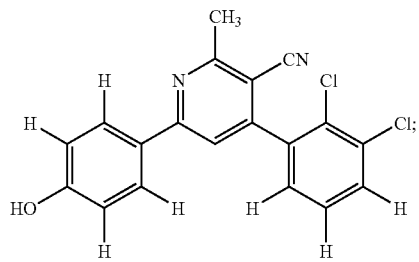

(FX47)
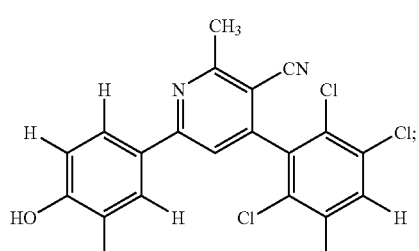

(FX48)
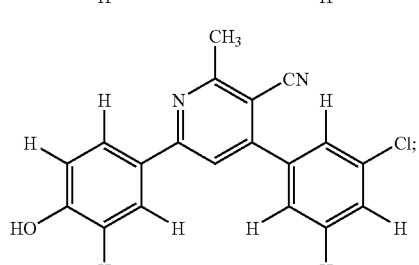

(FX49)
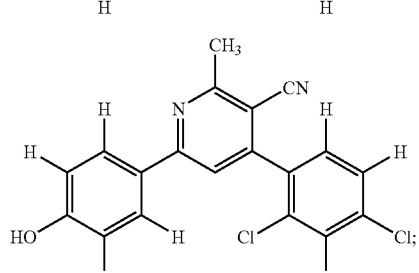

(FX50)
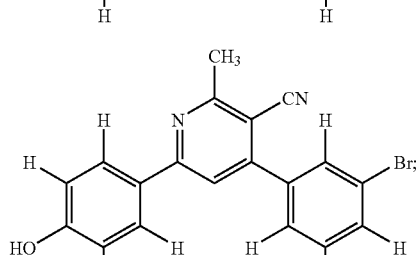

(FX51)
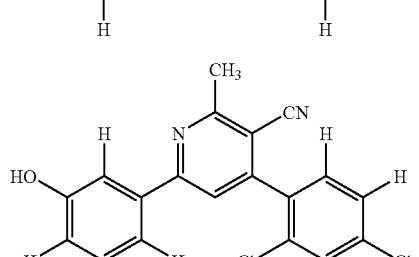

(FX52)
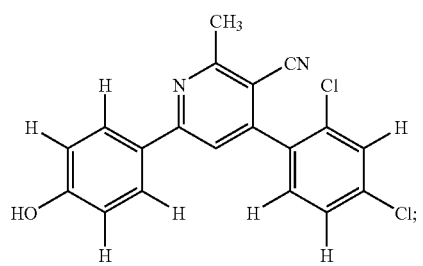
(FX53)
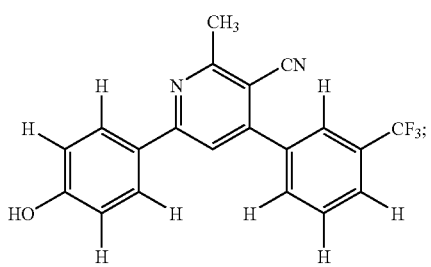
(FX54)
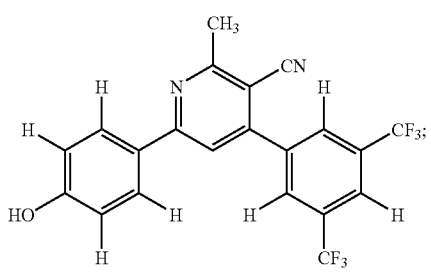
(FX55)
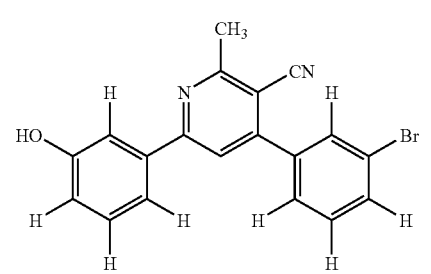
(FX56)
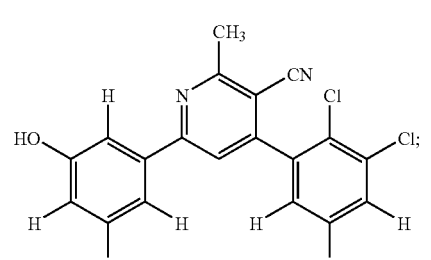
(FX57)
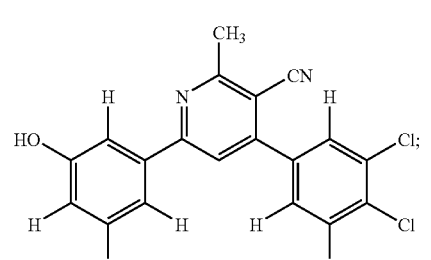
(FX58)
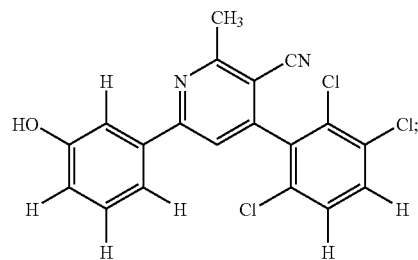
(FX59)
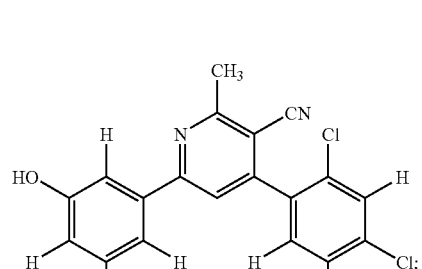
(FX60)
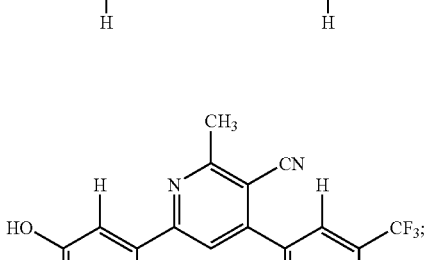
(FX61)
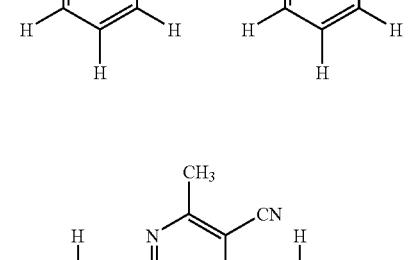 and
(FX62)
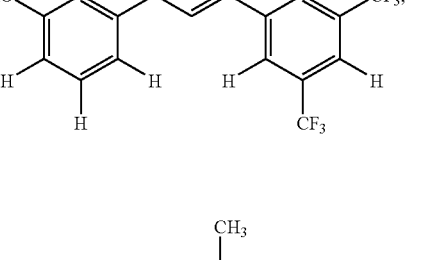
5. A pharmaceutical composition comprising a therapeutically effective amount of one or more compounds of claim 1 and a pharmaceutically acceptable carrier.

6. A compound of claim 1 having a formula selected from the group consisting of:

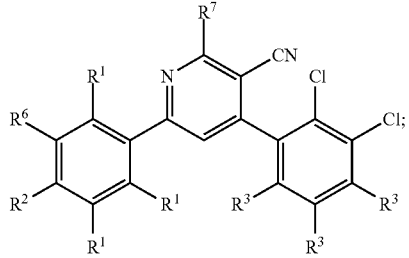
(FX37)

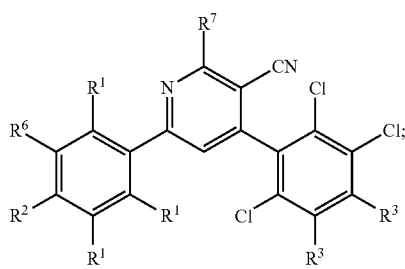
(FX38)

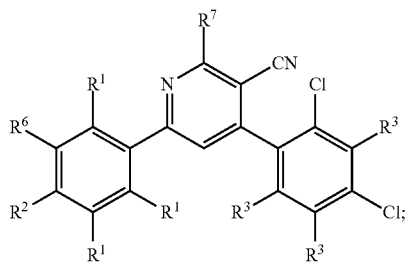
(FX39)

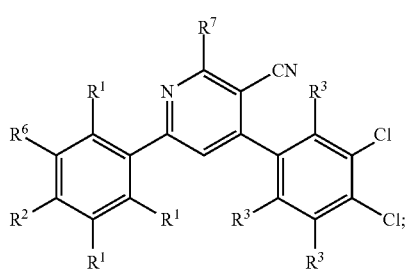
(FX40)

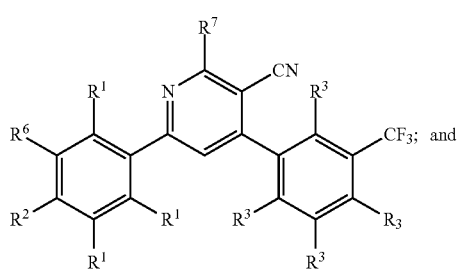
(FX43); and

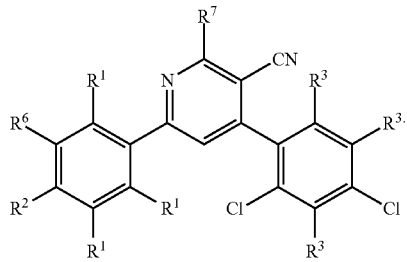
(FX45)

7. A compound of claim 6 wherein one of $R^2$ and $R^6$ is —OH, —OCH$_3$, —OCH$_2$CH$_3$, —OCH$_2$CH$_2$CH$_3$, —OCH$_2$CH$_2$CH$_2$CH$_3$ or —OCH$_2$CH$_2$CH$_2$CH$_2$CH$_3$ and the other of $R^2$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

8. A compound of claim 6 wherein $R^2$ is —OH, —OCH$_3$, —OCH$_2$CH$_3$, —OCH$_2$CH$_2$CH$_3$, —OCH$_2$CH$_2$CH$_2$CH$_3$ or —OCH$_2$CH$_2$CH$_2$CH$_2$CH$_3$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

9. A compound of claim 1 having a formula selected from the group consisting of:

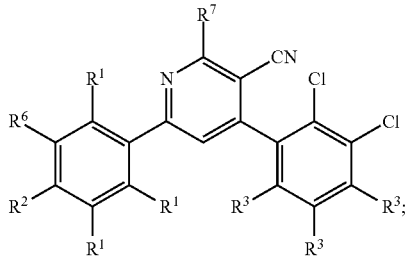
(FX37)

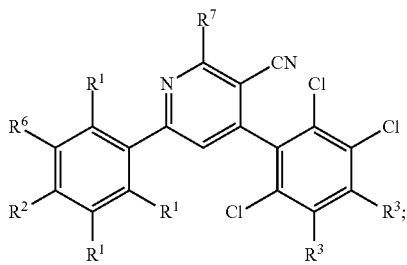
(FX38)

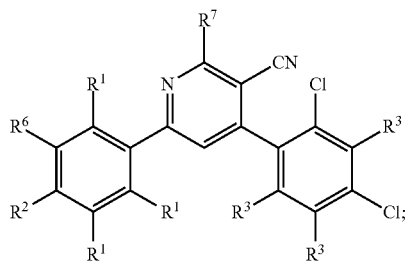
(FX39)

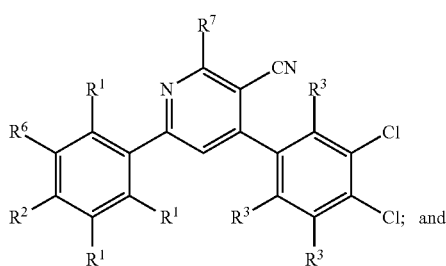

(FX40)

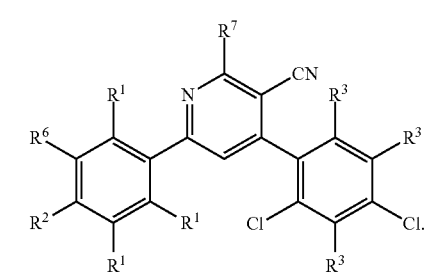

(FX45)

10. A compound of claim 9 wherein one of $R^2$ and $R^6$ is —OH, —OCH$_3$, —OCH$_2$CH$_3$, —OCH$_2$CH$_2$CH$_3$, —OCH$_2$CH$_2$CH$_2$CH$_3$ or —OCH$_2$CH$_2$CH$_2$CH$_2$CH$_3$ and the other of $R^2$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

11. A compound of claim 9 wherein $R^2$ is —OH, —OCH$_3$, —OCH$_2$CH$_3$, —OCH$_2$CH$_2$CH$_3$, —OCH$_2$CH$_2$CH$_2$CH$_3$ or —OCH$_2$CH$_2$CH$_2$CH$_2$CH$_3$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

12. A compound of claim 11 having a formula selected from the group consisting of

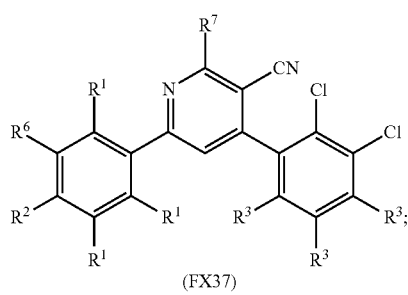

(FX37)

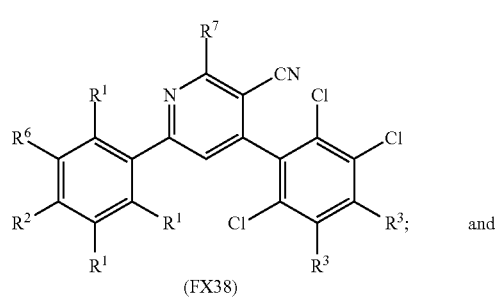

(FX38)

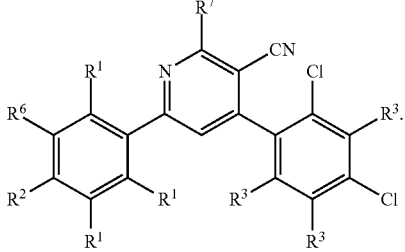

13. A compound of claim 1 wherein:

each $R^1$ is independently selected from the group consisting of —H, —CH$_3$, —CH$_2$CH$_3$, —CH$_2$CH$_2$CH$_3$ and —CH$_2$CH$_2$CH$_2$CH$_3$;

$R^2$ is selected from the group consisting of —H, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —OH, —OCH$_3$, —OCH$_2$CH$_3$, —OCH$_2$CH$_2$CH$_3$, —OCH$_2$CH$_2$CH$_2$CH$_3$ and —OCH$_2$CH$_2$CH$_2$CH$_2$CH$_3$;

each $R^3$ is independently selected from the group consisting of a hydrogen, a halogen, and an unsubstituted $C_1$-$C_8$ alkyl group;

$R^6$ is selected from the group consisting of —H, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —OH, —OCH$_3$, —OCH$_2$CH$_3$, —OCH$_2$CH$_2$CH$_3$, —OCH$_2$CH$_2$CH$_2$CH$_3$ and —OCH$_2$CH$_2$CH$_2$CH$_2$CH$_3$; and $R^7$ is selected from the group consisting of —CH$_3$, —CH$_2$CH$_3$, —CH$_2$CH$_2$CH$_3$ and —CH$_2$CH$_2$CH$_2$CH$_3$;

wherein one of $R^2$ and $R^6$ is —OH, —OCH$_3$, —OCH$_2$CH$_3$, —OCH$_2$CH$_2$CH$_3$, —OCH$_2$CH$_2$CH$_2$CH$_3$ and —OCH$_2$CH$_2$CH$_2$CH$_2$CH$_3$; and the other of $R^2$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

14. The compound of claim 13 wherein each $R^3$ is independently selected from the group consisting of a hydrogen, a methyl group and a chlorine;

$R^4$ is chlorine; and $R^5$ is —CF$_3$.

15. The compound of claim 14 wherein each $R^1$ is —H;

$R^2$ is —H, or —OH;

$R^6$ is —H, or —OH, and $R^7$ is —CH$_3$.

16. The compound of claim 13 having a formula selected from the group consisting of:

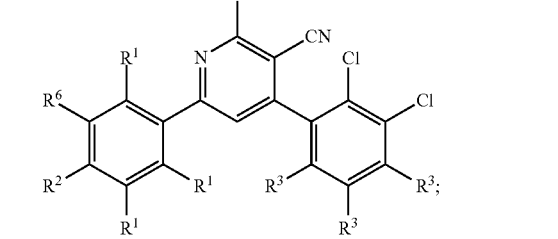

(FX37)

-continued

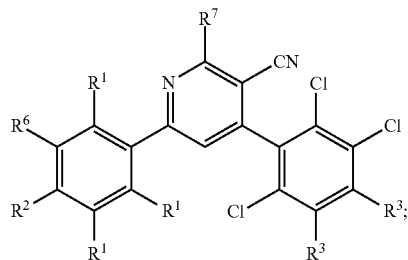
(FX38)

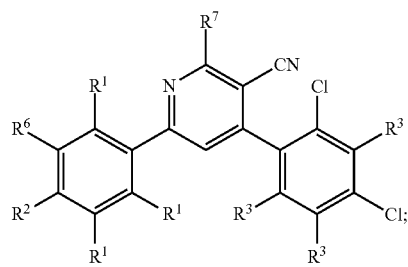
(FX39)

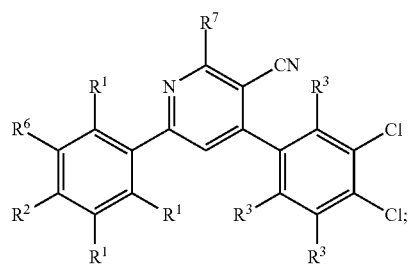
(FX40)

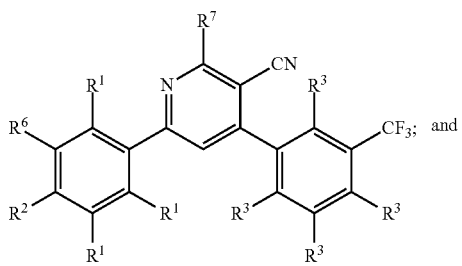
(FX43)

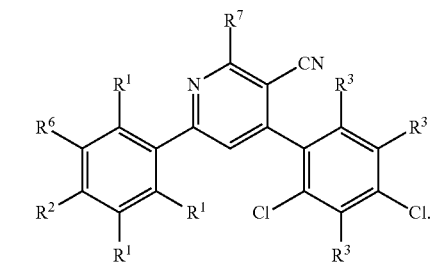
(FX45)

17. A compound of claim 16 wherein:

each $R^1$ is independently selected from the group consisting of —H, —CH$_3$, —CH$_2$CH$_3$, —CH$_2$CH$_2$CH$_3$ and —CH$_2$CH$_2$CH$_2$CH$_3$;

$R^2$ is selected from the group consisting of —H, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —OH, —OCH$_3$, —OCH$_2$CH$_3$, —OCH$_2$CH$_2$CH$_3$, —OCH$_2$CH$_2$CH$_2$CH$_3$ and —OCH$_2$CH$_2$CH$_2$CH$_2$CH$_3$;

each $R^3$ is independently selected from the group consisting of a hydrogen and an unsubstituted C$_1$-C$_3$ alkyl group;

$R^6$ is selected from the group consisting of —H, —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —OH, —OCH$_3$, —OCH$_2$CH$_3$, —OCH$_2$CH$_2$CH$_3$, —OCH$_2$CH$_2$CH$_2$CH$_3$ and —OCH$_2$CH$_2$CH$_2$CH$_2$CH$_3$; and $R^7$ is —CH$_3$;

wherein one of $R^2$ and $R^6$ is —OH, —OCH$_3$, —OCH$_2$CH$_3$, —OCH$_2$CH$_2$CH$_3$, —OCH$_2$CH$_2$CH$_2$CH$_3$ or —OCH$_2$CH$_2$CH$_2$CH$_2$CH$_3$ and the other of $R^2$ and $R^6$ is —H, —CH$_3$, —CH$_2$CH$_3$, —CH$_2$CH$_2$CH$_3$, —CH$_2$CH$_2$CH$_2$CH$_3$, or —CH$_2$CH$_2$CH$_2$CH$_2$CH$_3$.

18. The compound of claim 16 wherein each $R^1$ is —H;

$R^2$ is —H, or —OH;

$R^6$ is —H, or —OH, and $R^7$ is —CH$_3$.

19. A compound of claim 1 having a formula selected from the group consisting of:

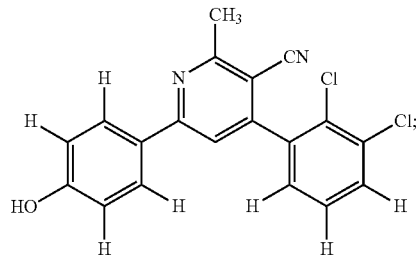
(FX46)

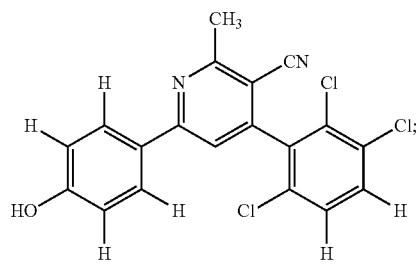
(FX47)

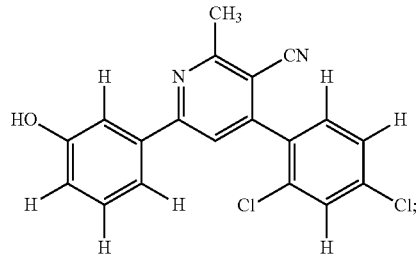
(FX51)

(FX52)
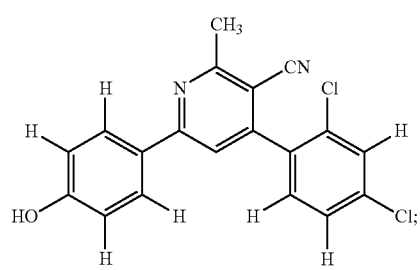
(FX58)
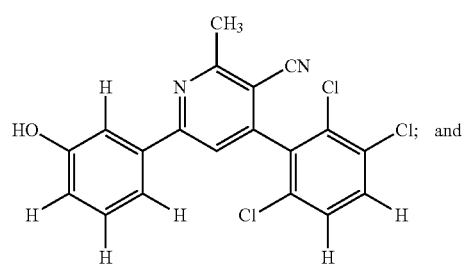
and
(FX56)
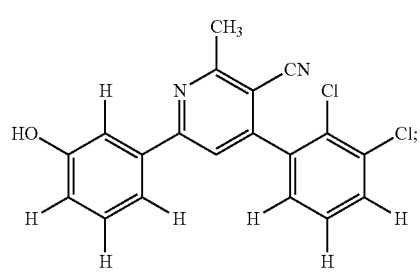
(FX60)
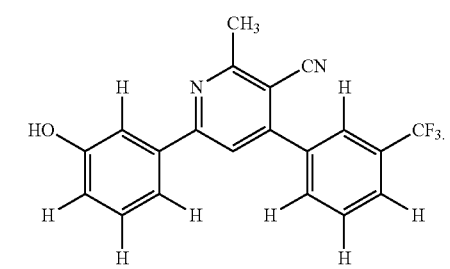
20. A pharmaceutical composition comprising a therapeutically effective amount of one or more compounds of claim 19 and a pharmaceutically acceptable carrier.
* * * * *